(12) United States Patent
Stasko et al.

(10) Patent No.: US 10,525,275 B2
(45) Date of Patent: Jan. 7, 2020

(54) SYSTEMS AND METHODS FOR PHOTOTHERAPEUTIC MODULATION OF NITRIC OXIDE

(71) Applicant: PhotonMD, Inc., Morrisville, NC (US)

(72) Inventors: Nathan Stasko, Chapel Hill, NC (US); Nicholas William Medendorp, Jr., Raleigh, NC (US); Gerald H. Negley, Chapel Hill, NC (US); Katelyn P. Reighard, Chapel Hill, NC (US)

(73) Assignee: PhotonMD, Inc., Morrisville, NC (US)

( * ) Notice: Subject to any disclaimer, the term of this patent is extended or adjusted under 35 U.S.C. 154(b) by 443 days.

(21) Appl. No.: 15/222,199

(22) Filed: Jul. 28, 2016

(65) Prior Publication Data
US 2017/0028214 A1    Feb. 2, 2017

Related U.S. Application Data

(60) Provisional application No. 62/197,746, filed on Jul. 28, 2015.

(51) Int. Cl.
*A61N 5/06* (2006.01)
*H01L 27/15* (2006.01)

(52) U.S. Cl.
CPC ......... *A61N 5/0613* (2013.01); *A61N 5/0601* (2013.01); *A61N 5/0603* (2013.01);
(Continued)

(58) Field of Classification Search
USPC .................................................... 607/86–94
See application file for complete search history.

(56) References Cited

U.S. PATENT DOCUMENTS

| | | |
|---|---|---|
| 5,549,639 A | 8/1996 | Ross |
| 6,096,066 A | 8/2000 | Chen et al. |

(Continued)

FOREIGN PATENT DOCUMENTS

| | | |
|---|---|---|
| AU | 2016100390 A4 | 7/2016 |
| EP | 2508229 A1 | 10/2012 |

(Continued)

OTHER PUBLICATIONS

Author Unknown, "Theradome Laser Helmet Review—A 120 Day Continuous Journal," Prevent Hair Loss Products, Jan. 14, 2014, retrieved Jun. 27, 2017, https://web.archive.org/web/20140610024017/http://preventhairlossproducts.com:80/theradome-laser-helmet-review-120-day-continuous-journal/, pp. 1-4.

(Continued)

*Primary Examiner* — Carl H Layno
*Assistant Examiner* — Dacheng Xie
(74) *Attorney, Agent, or Firm* — Nexsen Pruet, PLLC; David S. Bradin; E. Eric Mills

(57) ABSTRACT

Systems and methods for phototherapeutic modulation of nitric oxide in mammalian tissue include use of a first wavelength and first radiant flux of light to stimulate enzymatic generation of nitric oxide, and use of a second wavelength and second radiant flux of light to stimulate release of nitric oxide from endogenous stores of nitric oxide. Pulsed light and/or partially non-overlapping light impingement windows may be used. Non-coherent light impinged on tissue may include a peak wavelength in a range of from 410 nm to 440 nm in the absence of light emissions having a peak wavelength of from 600 nm to 900 nm.

17 Claims, 49 Drawing Sheets

(52) U.S. Cl.
CPC ...... *H01L 27/15* (2013.01); *A61N 2005/0626* (2013.01); *A61N 2005/0647* (2013.01); *A61N 2005/0652* (2013.01); *A61N 2005/0662* (2013.01); *A61N 2005/0663* (2013.01)

(56) References Cited

U.S. PATENT DOCUMENTS

| | | |
|---|---|---|
| 6,171,332 B1 | 1/2001 | Whitehurst |
| 6,290,713 B1 | 9/2001 | Russell |
| 6,497,719 B2 | 12/2002 | Pearl et al. |
| 6,645,230 B2 | 11/2003 | Whitehurst |
| 7,201,764 B2 | 4/2007 | Pearl et al. |
| 7,304,201 B2 | 12/2007 | Holloway et al. |
| D599,954 S | 9/2009 | Michaels et al. |
| D631,604 S | 1/2011 | Michaels et al. |
| D635,686 S | 4/2011 | Tucker et al. |
| D639,751 S | 6/2011 | Tucker et al. |
| D640,793 S | 6/2011 | Britt |
| 8,192,473 B2 | 6/2012 | Tucker et al. |
| 8,771,327 B2 | 7/2014 | Pearl et al. |
| 8,845,704 B2 | 9/2014 | Dunning et al. |
| D716,493 S | 10/2014 | Michaels et al. |
| 8,900,283 B2 | 12/2014 | Johnson et al. |
| 9,017,391 B2 | 4/2015 | McDaniel |
| D754,897 S | 4/2016 | Michaels et al. |
| 9,561,386 B2 | 2/2017 | Pearl et al. |
| 2003/0130709 A1 | 7/2003 | D.C. et al. |
| 2003/0167080 A1 | 9/2003 | Hart et al. |
| 2003/0236487 A1 | 12/2003 | Knowlton |
| 2004/0044384 A1 | 3/2004 | Leber et al. |
| 2004/0073079 A1 | 4/2004 | Altshuler et al. |
| 2004/0162596 A1 | 8/2004 | Altshuler et al. |
| 2005/0045189 A1 | 3/2005 | Jay |
| 2006/0258896 A1 | 11/2006 | Haber et al. |
| 2007/0060819 A1 | 3/2007 | Altshuler et al. |
| 2007/0106856 A1 | 5/2007 | Nomura et al. |
| 2007/0208396 A1 | 9/2007 | Whatcott et al. |
| 2007/0213792 A1 | 9/2007 | Yaroslavsky et al. |
| 2007/0233208 A1 | 10/2007 | Kurtz et al. |
| 2008/0033516 A1 | 2/2008 | Altshuler et al. |
| 2008/0319430 A1 | 12/2008 | Zenzie et al. |
| 2009/0254156 A1 | 10/2009 | Powell et al. |
| 2009/0318802 A1* | 12/2009 | Boyden ............. A61B 5/02007 600/437 |
| 2010/0004645 A1 | 1/2010 | Jeong et al. |
| 2010/0049180 A1 | 2/2010 | Wells et al. |
| 2010/0242155 A1 | 9/2010 | Carullo, Jr. |
| 2011/0015707 A1 | 1/2011 | Tucker et al. |
| 2011/0054573 A1 | 3/2011 | Mitchell |
| 2011/0144410 A1* | 6/2011 | Kennedy ............. A61B 18/203 600/2 |
| 2011/0144727 A1 | 6/2011 | Benedict |
| 2011/0160814 A2 | 6/2011 | Tucker et al. |
| 2012/0059440 A1 | 3/2012 | Hamid |
| 2012/0065709 A1 | 3/2012 | Dunning et al. |
| 2013/0041432 A1 | 2/2013 | Tucker et al. |
| 2013/0131762 A1 | 5/2013 | Oversluizen et al. |
| 2013/0144364 A1 | 6/2013 | Wagenaar Cacciola et al. |
| 2014/0128941 A1 | 5/2014 | Williams |
| 2014/0128942 A1 | 5/2014 | Bembridge et al. |
| 2014/0276248 A1 | 9/2014 | Hall et al. |
| 2014/0303693 A1 | 10/2014 | Haarlander et al. |
| 2014/0350643 A1 | 11/2014 | Pepitone et al. |
| 2015/0005854 A1 | 1/2015 | Said |
| 2015/0112411 A1* | 4/2015 | Beckman ............. A61N 5/0616 607/90 |
| 2015/0297914 A1 | 10/2015 | Hamid et al. |
| 2016/0106999 A1 | 4/2016 | Michaels et al. |
| 2016/0271420 A1 | 9/2016 | Pina |

FOREIGN PATENT DOCUMENTS

| | | |
|---|---|---|
| EP | 3069762 A1 | 9/2016 |
| WO | 2004033040 A1 | 4/2004 |
| WO | 2008144157 A1 | 11/2008 |
| WO | 2014146029 A1 | 9/2014 |

OTHER PUBLICATIONS

International Preliminary Report on Patentability for PCT/US2016/044400, dated Feb. 8, 2018, 7 pages.

Non-Final Office Action for U.S. Appl. No. 15/222,243, dated Jan. 11, 2019, 10 pages.

Abeyakirthi, Sharnika, "Nitric oxide," DermNet NZ, 2009, 4 pages, http://www.dermnetnz.org/topics/nitric-oxide/.

Andrew, Penelope J. et al., "Enzymatic function of nitric oxide synthases," Cardiovascular Research, vol. 43, No. 3, Aug. 15, 1999, pp. 521-531.

Author Unknown, "Brilliant Light Therapy," In Light Wellness Systems, eBrochure, Date Unknown, 5 pages.

Author Unknown, "Healed by Light," Digi-Key Electronics, Jul. 1, 2014, 4 pages, http://www.digikey.com/es/articles/techzone/2014/jul/healed-by-light.

Author Unknown, "illuMask," La Lumière, Date Unknown, 2 pages, http://www.illumask.com/dimming/.

Author Unknown, "Near-IR Photoluminescent Dyes for Molecular Labeling," NanoQuantum, Technology, 2013, 7 pages, http://www.nanoquantum.com/Technology.html.

Author Unknown, "Philips Blue Touch," Koninklijke Philips N.V., Version 1.0.1, Sep. 1, 2013, 2 pages.

Author Unknown, "Ultraviolet Light Therapy," Wound Care Centers, Date Unknown, 3 pages, http://www.woundcarecenters.org/article/wound-therapies/ultraviolet-light-therapy.

Author Unknown, "What is Light Therapy used for?" Rio, The Dezac Group, Ltd, Date Unknown, 4 pages, http://www.lightmask.com/uses_for_lt.htm#top.

Avci, Pinar et al., "Low-Level Laser (Light) Therapy (LLLT) for Treatment of Hair Loss," Lasers in Surgery and Medicine, vol. 46, 2014, pp. 144-151.

Avci, Pinar et al., "Low-Level Laser (Light) Therapy (LLLT) in Skin: Stimulating, Healing, Restoring," Seminars in Cutaneous Medicine and Surgery, vol. 32, No. 1, 2013, pp. 41-52.

Ball, Kerri A. et al., "Low intensity light stimulates nitrite-dependent nitric oxide synthesis but not oxygen consumption by cytochrome c oxidase: Implications for phototherapy," Journal of Photochemistry and Photobiology B, vol. 102, No. 3, 2011, pp. 182-191.

Barolet, Daniel, "Light-Emitting Diodes (LEDs) in Dermatology," Seminars in Cutaneous Medicine and Surgery, vol. 27, No. 4, Dec. 1, 2008, pp. 227-238.

Cals-Grierson, M.-M. et al., "Nitric oxide function in the skin," Nitric Oxide, vol. 10, No. 4, Jun. 2004, pp. 179-193.

Chaves, Maria Emília De Abreu et al., "Effects of low-power light therapy on wound healing: Laser x LED," Anais Brasileiros de Dermatologia, vol. 89, No. 4, Jul./Aug. 2014, pp. 616-623.

Farivar, Shirin et al., "Biological Effects of Low Level Laser Therapy," Journal of Lasers in Medical Sciences, vol. 5, No. 2, Spring 2014, pp. 58-62.

Feelisch, Martin et al., "Concomitant S-, N-, and heme-nitros(yl)ation in biological tissues and fluids: implications for the fate of NO in vivo," FASEB, vol. 16, No. 13, Nov. 2002, pp. 1775-1785.

Gupta, Asheesh et al., "History and Fundamentals of Low-Level Laser (Light) Therapy," Handbook of Photomedicine, Chapter 5, CRC Press, 2014, pp. 43-52.

Hamblin, Michael R. et al., "Mechanisms of Low Level Light Therapy," Proceedings of the SPIE, vol. 6140, Feb. 10, 2006, pp. 614001-1 to 641001-12.

Hamblin, Michael R., "Mechanisms of Low Level Light Therapy," Aug. 14, 2008, 22 pages, http://photobiology.info/Hamblin.html.

(56) References Cited

OTHER PUBLICATIONS

Hamblin, Michael R., "The Role of Nitric Oxide in Low Level Light Therapy," Proceedings of SPIE, vol. 6846, 2008, pp. 684602-1 to 684602-14.

Karu, Tiina I., "Low-Power Laser Therapy," Biomedical Photonics Handbook, Chapter 48, CRC Press, 2003, pp. 48-1 to 48-25.

Kirima, Kazuyoshi et al., "Evaluation of systemic blood NO dynamics by EPR spectroscopy: HbNO as an endogenous index of NO," American Journal of Physiology Heart and Circulatory Physiology, vol. 285, No. 2, Aug. 2003, pp. H589-H596.

Kovacs, Izabella et al., "Nitric oxide-based protein modification: formation and site-specificity of protein S-nitrosylation," Frontiers in Plant Science, vol. 4, Article 137, May 14, 2013, 10 pages.

Leong, Mimi, "Effects of Light-Emitting Diode Photostimulation on Burn Wound Healing," Thesis, The University of Texas Graduate School of Biomedical Sciences at Galveston, May 2006, 92 pages.

Mandel, Arkady, et al., "A renaissance in low-level laser (light) therapy—LLLT," Photonics and Lasers in Medicine, vol. 1, No. 4, Nov. 2012, pp. 231-234.

Martin, Richard, "Laser-Accelerated Inflammation/Pain Reduction and Healing," Practical Pain Management, vol. 3, No. 6, Nov./Dec. 2003, pp. 20-25.

Phurrough, Steve et al., "Decision Memo for Infrared Therapy Devices (CAG-00291N)," Centers for Medicare & Medicaid Services, Oct. 24, 2006, 37 pages.

Poyton, Robert O. et al., "Therapeutic Photobiomodulation: Nitric Oxide and a Novel Function of Mitochondrial Cytochrome C Oxidase," Discovery Medicine, Feb. 20, 2011, 11 pages.

Sarti, Paolo et al., "The Chemical Interplay between Nitric Oxide and Mitochondrial Cytochrome c Oxidase: Reactions, Effectors and Pathophysiology," International Journal of Cell Biology, vol. 2012, Article 571067, 2012, 11 pages.

Adamskaya, Natalia et al., "Light therapy by blue LED improves wound healing in an excision model in rats," Injury, 2010, 5 pages.

International Search Report and Written Opinion for PCT/US2016/044400, dated Oct. 4, 2016, 8 pages.

Author Unknown, "IPL Hair Removal," Spectrum Science & Beauty, Spectrum Blog, Sep. 16, 2014, 3 pages, http://www.spectrumsciencebeauty.com.au/ipl-hair-removal/#prettyPhoto.

* cited by examiner

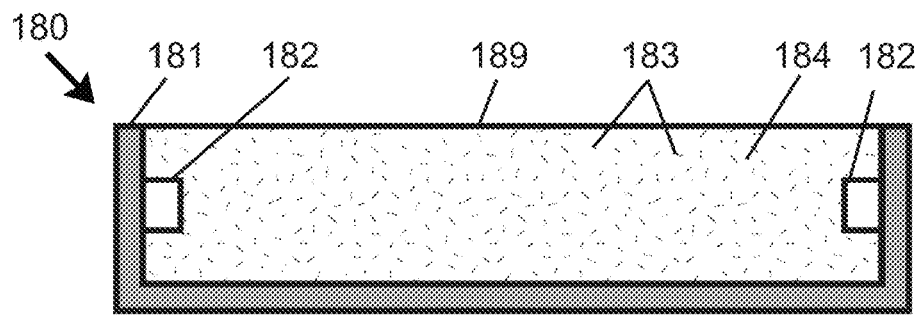
*Figure 26*
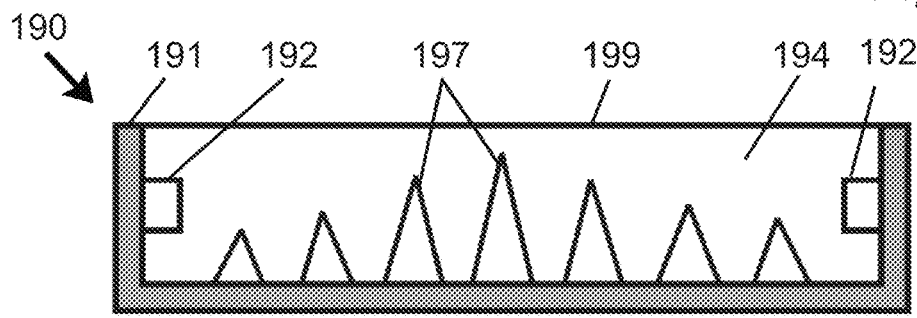
*Figure 27*
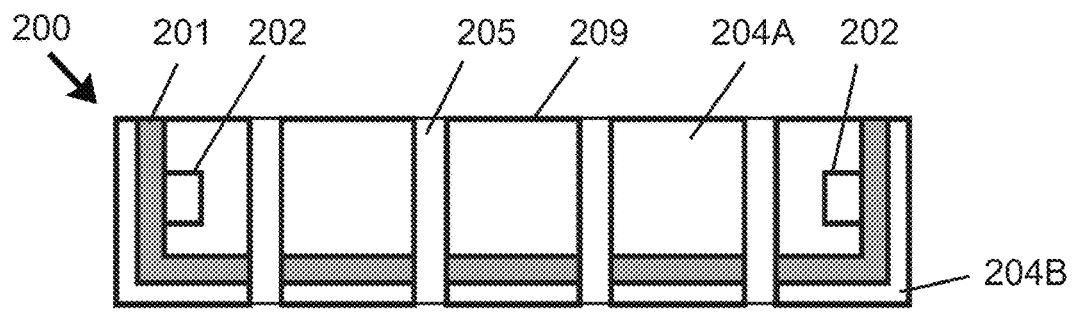
*Figure 28*
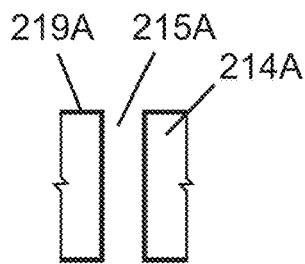 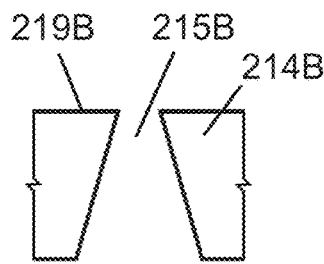 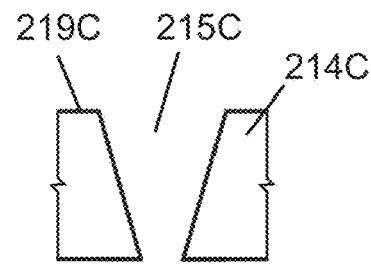
*Figure 29A*    *Figure 29B*    *Figure 29C*

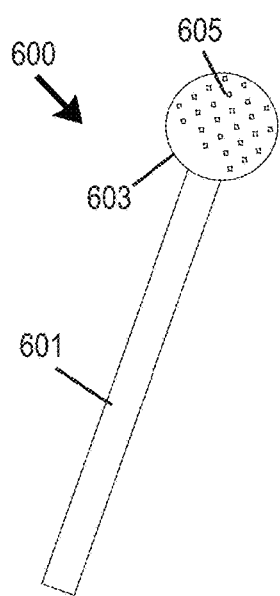
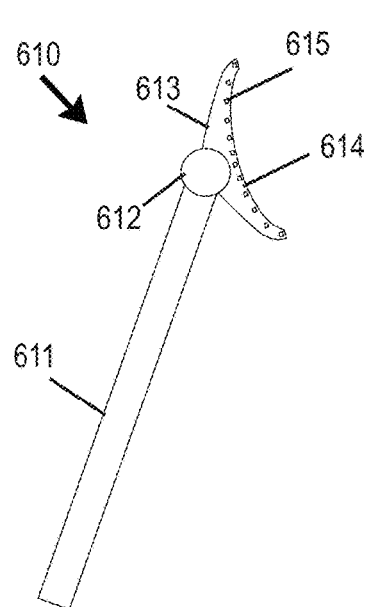
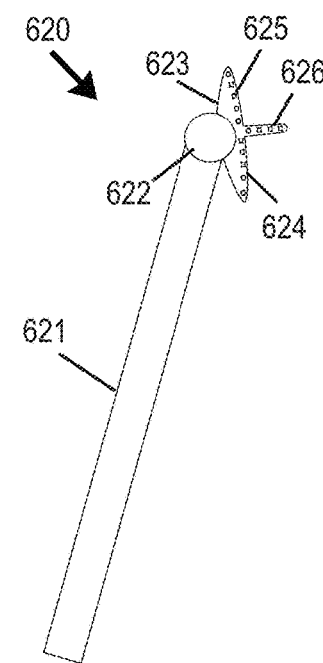
Figure 42   Figure 43A   Figure 44A
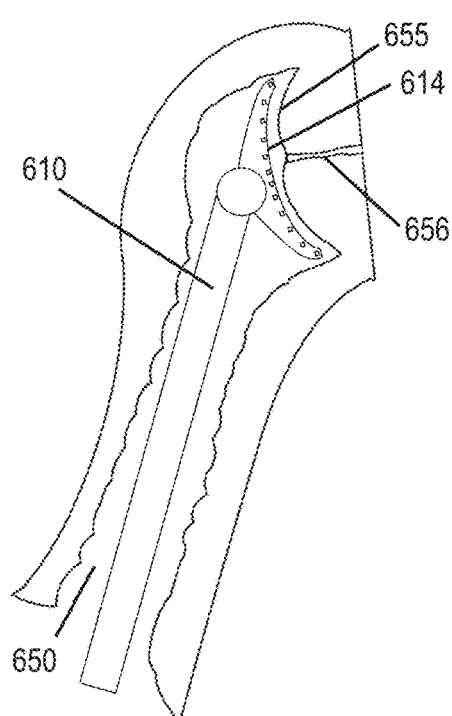
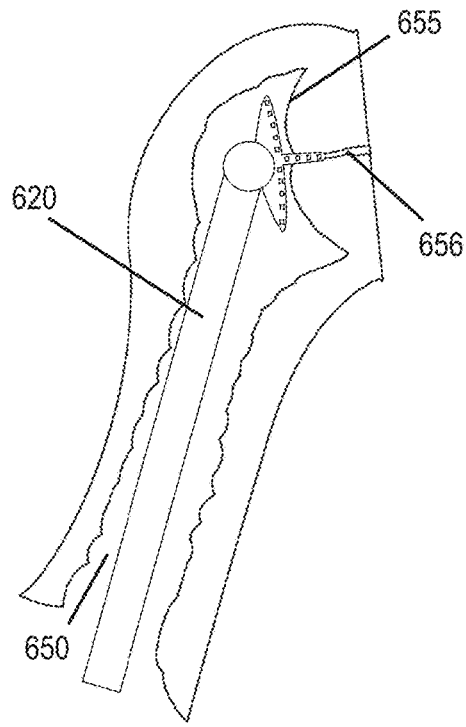
Figure 43B   Figure 44B

SYSTEMS AND METHODS FOR PHOTOTHERAPEUTIC MODULATION OF NITRIC OXIDE

STATEMENT OF RELATED APPLICATIONS

This application claims the benefit of provisional patent application Ser. No. 62/197,746, filed Jul. 28, 2015, the disclosure of which is hereby incorporated herein by reference in its entirety.

TECHNICAL FIELD

This disclosure relates to systems and methods for phototherapeutic stimulation of nitric oxide production and/or release in tissues of mammalian subjects.

BACKGROUND

The term "phototherapy" relates to the therapeutic use of light. Various light therapies (e.g., including low level light therapy (LLLT) and photodynamic therapy (PDT)) have been publicly reported or claimed to provide various health related medical benefits—including, but not limited to: promoting hair growth; treatment of skin or tissue inflammation; promoting tissue or skin healing or rejuvenation; enhancing wound healing; pain management; reduction of wrinkles, scars, stretch marks, varicose veins, and spider veins; treating cardiovascular disease; treating erectile dysfunction; treating microbial infections; treating hyperbilirubinemia; and treating various oncological and non-oncological diseases or disorders.

Various mechanisms by which phototherapy has been suggested to provide therapeutic benefits include: increasing circulation (e.g., by increasing formation of new capillaries); stimulating the production of collagen; stimulating the release of adenosine triphosphate (ATP); enhancing porphyrin production; reducing excitability of nervous system tissues; modulating fibroblast activity; increasing phagocytosis; inducing thermal effects; stimulating tissue granulation and connective tissue projections; reducing inflammation; and stimulating acetylcholine release.

Phototherapy has also been suggested to stimulate cells to generate nitric oxide. Various biological functions attributed to nitric oxide include roles as signaling messenger, cytotoxin, antiapoptotic agent, antioxidant, and regulator of microcirculation. Nitric oxide is recognized to relax vascular smooth muscles, dilate blood vessels, inhibit aggregation of platelets, and modulate T cell-mediate immune response.

Nitric oxide is produced by multiple cell types in tissue, and is formed by the conversion of the amino acid L-arginine to L-citrulline and nitric oxide, mediated by the enzymatic action of nitric oxide synthases (NOSs). NOS is a NADPH-dependent enzyme that catalyzes the following reaction:

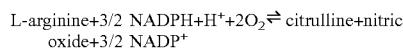

L-arginine+3/2 NADPH+H$^+$+2O$_2$⇌ citrulline+nitric oxide+3/2 NADP$^+$

In mammals, three distinct genes encode NOS isozymes: neuronal (nNOS or NOS-I), cytokine-inducible (iNOS or NOS-II), and endothelial (eNOS or NOS-III). iNOS and nNOS are soluble and found predominantly in the cytosol, while eNOS is membrane associated. Many cells in mammals synthesize iNOS in response to inflammatory conditions.

Skin has been documented to upregulate inducible nitric oxide synthase expression and subsequent production of nitric oxide in response to irradiation stress. Nitric oxide serves a predominantly anti-oxidant role in the high levels generated in response to radiation.

Nitric oxide is a free radical capable of diffusing across membranes and into various tissues; however, it is very reactive, with a half-life of only a few seconds. Due to its unstable nature, nitric oxide rapidly reacts with other molecules to form more stable products. For example, in the blood, nitric oxide rapidly oxidizes to nitrite, and is then further oxidized with oxyhaemoglobin to produce nitrate. Nitric oxide also reacts directly with oxyhaemoglobin to produce methaemoglobin and nitrate. Nitric oxide is also endogenously stored on a variety of nitrosated biochemical structures including nitrosoglutathione (GSNO), nitrosoalbumin, nitrosohemoglobin, and a large number of nitrosocysteine residues on other critical blood/tissue proteins. The term "nitroso" is defined as a nitrosated compound (nitrosothiols (RSNO) or nitrosamines (RNNO)), via either S- or N-nitrosation. Examples of nitrosated compounds include GSNO, nitrosoalbumin, nitrosohemoglobin, and proteins with nitrosated cysteine residue. Metal nitrosyl (M-NO) complexes are another endogenous store of circulating nitric oxide, most commonly found as ferrous nitrosyl complexes in the body; however, metal nitrosyl complexes are not restricted to complexes with iron-containing metal centers, since nitrosation also occurs at heme groups and copper centers. Examples of metal nitrosyl complexes include cytochrome c oxidase (CCO-NO) (exhibiting 2 heme and 2 copper binding sites), cytochrome c (exhibiting heme center binding), and nitrosylhemoglobin (exhibiting heme center binding for hemoglobin and methemoglobin), embodying endogenous stores of nitric oxide.

FIG. 1 is a reaction sequence showing photoactivated production of nitric oxide catalyzed by iNOS, followed by binding of nitric oxide to CCO.

When nitric oxide is auto-oxidized into nitrosative intermediates, the nitric oxide is bound covalently in the body (in a "bound" state). Thus, conventional efforts to produce nitric oxide in tissue may have a limited therapeutic effect, since nitric oxide in its "gaseous" state is short-lived, and cells being stimulated to produce nitric oxide may become depleted of NADPH or L-Arginine to sustain nitric oxide production.

SUMMARY

Certain aspects of the disclosure relate to phototherapeutic modulation of nitric oxide in living mammalian tissue, including use of light having a first peak wavelength and a first radiant flux to release nitric oxide from endogenous stores of nitric oxide, and use of light having a second peak wavelength and a second radiant flux to stimulate enzymatic generation of nitric oxide to increase endogenous stores of nitric oxide, wherein the second peak wavelength differs from the first peak wavelength.

In a first aspect, the disclosure relates to a method of modulating nitric oxide in living mammalian tissue. The method includes impinging light having a first peak wavelength on the tissue at a first radiant flux, wherein the first peak wavelength and the first radiant flux are selected to stimulate enzymatic generation of nitric oxide to increase endogenous stores of nitric oxide. The method further includes impinging light having a second peak wavelength on the tissue at a second radiant flux, wherein the second peak wavelength and the second radiant flux are selected to release nitric oxide from the endogenous stores, wherein the second peak wavelength is greater than the first peak wavelength by at least 25 nm, by at least 50 nm, or another threshold specified herein. In certain embodiments, each of the first radiant flux and the second radiant flux is in a range of from 5 mW/cm$^2$ to 60 mW/cm$^2$.

In certain embodiments, the enzymatic generation of nitric oxide is mediated by iNOS, nNOS, and/or eNOS in or proximate to the tissue. In certain embodiments, the endogenous stores of nitric oxide comprise nitrosoglutathione, nitrosoalbumin, nitrosohemoglobin, nitrosothiols, nitrosamines, and/or metal nitrosyl complexes in or proximate to the tissue.

In certain embodiments, the method further includes sensing a temperature condition on or proximate to (a) a therapeutic device arranged to emit at least one of the light having the first peak wavelength or the light having the second peak wavelength, or (b) the tissue; generating at least one signal indicative of the temperature condition; and controlling at least one of the following items (i) or (ii) responsive to the at least one signal: (i) impingement of light having the first peak wavelength on the tissue, or (ii) impingement of light having the second peak wavelength on the tissue.

In another aspect, the disclosure relates to a device for modulating nitric oxide in living mammalian tissue. The device includes means for impinging light having a first peak wavelength on the tissue at a first radiant flux, wherein the first peak wavelength and the first radiant flux are selected to stimulate enzymatic generation of nitric oxide to increase endogenous stores of nitric oxide. The device further includes means for impinging light having a second peak wavelength on the tissue at a second radiant flux, wherein the second peak wavelength and the second radiant flux are selected to release nitric oxide from the endogenous stores, wherein the second peak wavelength is greater than the first peak wavelength by at least 25 nm.

In certain embodiments, the device further includes means for sensing a temperature condition on or proximate to (a) the device or (b) the tissue; means for generating at least one signal indicative of the temperature condition; and means for controlling at least one of the following items (i) or (ii) responsive to the at least one signal: (i) impingement of light having the first peak wavelength on the tissue, or (ii) impingement of light having the second peak wavelength on the tissue.

In another aspect, the disclosure relates to another device for modulating nitric oxide in living mammalian tissue. The device includes at least one first light emitting device configured to impinge light having a first peak wavelength on the tissue at a first radiant flux, wherein the first peak wavelength and the first radiant flux are selected to release nitric oxide from endogenous stores of nitric oxide. The device further includes at least one second light emitting device configured to impinge light having a second peak wavelength on the tissue at a second radiant flux, wherein the second peak wavelength and the second radiant flux are selected to stimulate enzymatic generation of nitric oxide to increase endogenous stores of nitric oxide, wherein the second peak wavelength exceeds the first peak wavelength by at least 25 nm, at least 50 nm, or another threshold specified herein. In certain embodiments, the device further includes driver circuitry configured to drive the at least one first light emitting device and the at least one second light emitting device. In certain embodiments, each of the first radiant flux and the second radiant flux is in a range of from 5 mW/cm$^2$ to 60 mW/cm$^2$.

In certain embodiments, the device further includes at least one third light emitting device configured to impinge light having a third peak wavelength on the tissue, wherein the third peak wavelength differs from each of the first peak wavelength and the second peak wavelength by at least 10 nm.

In certain embodiments, the device further includes a temperature sensor arranged to sense a temperature condition on or proximate to at least one of (a) a portion of the device or (b) the tissue, wherein at least one of initiation of operation, deviation of operation, or termination of operation of any of (i) the at least one first light emitting device or (ii) the at least one second light emitting device is responsive to an output signal of the temperature sensor.

In certain embodiments, the device further includes a flexible substrate supporting the at least one first light emitting device and the at least one second light emitting device.

In certain embodiments, the device further includes a light-transmissive (e.g., encapsulant) material layer covering the at least one first light emitting device, the at least one second light emitting device, and at least a portion of the flexible substrate.

In certain embodiments, the device further includes a plurality of holes defined in the flexible substrate and the light-transmissive material layer, wherein the plurality of holes are arranged to permit transit therethrough of at least one of air, vapor, or exudate.

In certain embodiments, the device is configured to contact, be connected to, or conform to a skin or other tissue of a patient with at least a portion of the light-transmissive material layer arranged in contact with the skin or other tissue of the patient. In other embodiments, the device is configured to be spatially separated from a targeted irradiation area, such as being arranged not to contact tissue of the patient.

In certain embodiments, the device further includes a substantially rigid substrate supporting the at least one first light emitting device and the at least one second light emitting device, wherein at least a portion of the device is configured for insertion into a body cavity of a patient.

In certain embodiments, the device further includes at least one waveguide arranged between (i) the tissue and (ii) at least one of the at least one first light emitting device or the at least one second light emitting device.

In certain embodiments, the device further includes a light scattering material, a textured light scattering surface, or a patterned light scattering surface arranged between (i) the tissue and (ii) at least one of the at least one first light emitting device or the at least one second light emitting device.

In certain embodiments, the device further includes an energy storage element arranged to supply power to the driver circuitry.

In another aspect, the disclosure relates to a device for delivering light energy to tissue of a patient. The device includes at least one first solid state light emitting device configured to impinge light having a first peak wavelength on the tissue. The device further includes at least one second solid state light emitting device configured to impinge light having a second peak wavelength on the tissue. The device additionally includes driver circuitry configured to drive the at least one first solid state light emitting device and the at least one second solid state light emitting device. The first peak wavelength and the second peak wavelength are selected from one of the following combinations (a) to (g): (a) the first peak wavelength is in a range of from 410 nm to 490 nm and the second peak wavelength is in a range of from 500 nm to 600 nm; (b) the first peak wavelength is in a range of from 620 nm to 640 nm and the second peak wavelength is in a range of from 650 nm to 670 nm; (c) the first peak wavelength is in a range of from 520 nm to 540 nm and the second peak wavelength is in a range of from 650 nm to 670 nm; (d) the first peak wavelength is in a range of from 400 nm to 420 nm and the second peak wavelength is in a range of from 620 nm to 640 nm; (e) the first peak wavelength is in a range of from 400 nm to 420 nm and the second peak wavelength is in a range of from 650 nm to 670 nm; (f) the first peak wavelength is in a range of from 400 nm to 420 nm and the second peak wavelength is in a range of from 495 nm to 515 nm; or (g) the first peak wavelength is in a range of from 400 nm to 420 nm and the second peak wavelength is in a range of from 516 nm to 545 nm. In certain embodiments, the first peak wavelength is in a range of from 400 nm to 420 nm and the second peak wavelength is in a range of from 525 nm to 535 nm.

In certain embodiments, the device further includes a temperature sensor arranged to sense a temperature condition on or proximate to at least one of (a) a portion of the device or (b) the tissue, wherein at least one of initiation of operation, deviation of operation, or termination of operation of at least one of (i) the at least one first solid state light emitting device or (ii) the at least one second solid state light emitting device is responsive to an output signal of the temperature sensor.

In another aspect, the disclosure relates to a method of modulating nitric oxide in living mammalian tissue, the method comprising: impinging light on the tissue, wherein the light impinged on the tissue comprises incoherent light emissions including a first peak wavelength in a range of from 410 nm to 440 nm and a first radiant flux, and wherein the first peak wavelength and the first radiant flux are selected to stimulate at least one of (i) enzymatic generation of nitric oxide to increase endogenous stores of nitric oxide or (ii) release of nitric oxide from endogenous stores of nitric oxide; wherein the light impinged on the tissue is substantially devoid of light emissions having a peak wavelength in a range of from 600 nm to 900 nm.

In certain embodiments, the light impinged on the tissue is devoid of emissions of any wavelength conversion material stimulated by incoherent light emissions including a first peak wavelength in a range of from 410 nm to 440 nm. In certain embodiments, the tissue is devoid of an applied or received photosensitive therapeutic compound or agent. In certain embodiments, at least 65% (or at least 80%, or at least 90%) of a fluence of light impinged on the tissue consists of the incoherent light emissions including a first peak wavelength in a range of from 410 to 440 nm. In certain embodiments, the light impinged on the tissue is substantially devoid of light emissions having a peak wavelength in a range of from 441 nm to 490 nm. In certain embodiments, the incoherent light emissions including a first peak wavelength in a range of from 410 nm to 440 nm are provided as a plurality of discrete pulses. In certain embodiments, the light impinged on the tissue further comprises incoherent light emissions including a second peak wavelength in a range of from 500 nm to 540 nm. In certain embodiments, the incoherent light emissions including a first peak wavelength in a range of from 410 nm to 440 nm are impinged on the tissue during a first time window, the incoherent light emissions including a second peak wavelength in a range of from 500 nm to 540 nm are impinged on the tissue during a second time window, and at least a portion of the second time window is non-overlapping with the first time window. In certain embodiments, the first peak wavelength and the first radiant flux are selected to release endogenous stores of nitric oxide. In certain embodiments, the second peak wavelength and the second radiant flux are selected to stimulate enzymatic generation of nitric oxide to increase endogenous stores of nitric oxide. In certain embodiments, the tissue comprises at least one of epithelial tissue, mucosal tissue, bone, connective tissue, muscle tissue, or cervical tissue. In certain embodiments, the tissue comprises dermal tissue. In certain embodiments, a method further comprises sensing a temperature condition on or proximate to (a) a therapeutic device arranged to impinge light on the tissue, or (b) the tissue; generating at least one signal indicative of the temperature condition; and controlling impingement of light on the tissue responsive to the at least one signal. In certain embodiments, the light impinged on the tissue comprises a fluence of from about 0.5 J/cm$^2$ to about 100 J/cm$^2$, or from about 5 J/cm$^2$ to about 50 J/cm$^2$.

In another aspect, the disclosure relates to a device for modulating nitric oxide in living mammalian tissue, the device comprising: an ambient light blocking element; and at least one first light emitting element positioned between the ambient light blocking element and the tissue, wherein the at least one first light emitting element is configured to impinge incoherent light on the tissue, said incoherent light having a first peak wavelength and a first radiant flux, wherein the first peak wavelength and the first radiant flux are selected to stimulate at least one of (i) enzymatic generation of nitric oxide to increase endogenous stores of nitric oxide or (ii) release of nitric oxide from endogenous stores of nitric oxide; wherein the device is substantially devoid of any light emitting element configured to impinge light on the tissue, said light having a peak wavelength in a range of from 600 nm to 900 nm.

In certain embodiments, the device is substantially devoid of any light emitting element configured to impinge light having a peak wavelength in a range of from 441 nm to 490 nm on the tissue. In certain embodiments, the device is devoid of any wavelength conversion material configured to be stimulated by the at least one first light emitting element. In certain embodiments, the device further comprises a flexible substrate supporting the at least one first light emitting element. In certain embodiments, the device is configured to contact, be connected to, or conform to the tissue with a light-transmissive material. In certain embodiments, light impinged on the tissue is substantially devoid of light emissions having a peak wavelength in a range of from 441 nm to 490 nm. In certain embodiments, the device further comprises driver circuitry configured to generate incoherent light emissions including the first peak wavelength, wherein the first peak wavelength is in a range of from 410 nm to 440 nm, and said incoherent light emissions comprise a plurality of discrete pulses.

In certain embodiments, the device further comprises at least one second light emitting element configured to impinge incoherent light on the tissue, said incoherent light having a second peak wavelength and a second radiant flux, wherein the second peak wavelength is in a range of from 500 nm to 540 nm. In certain embodiments, the device is configured to impinge incoherent light emissions including the first peak wavelength during a first time window, wherein the first peak wavelength is in a range of from 410 nm to 440 nm, and being configured to impinge incoherent light emissions including the second peak wavelength in a range of from 500 nm to 540 nm during a second time window, wherein at least a portion of the second time window is non-overlapping with the first time window. In certain embodiments, the device further comprises a probe configured for insertion into a mammalian body cavity or opening defined in a mammalian body, wherein the at least one first light emitting element is supported by the probe.

In another aspects, devices and/or methods disclosed herein may be used to modulate nitric oxide for managing or eliminating pathogens (such as bacteria, viruses, fungi, protists, or the like) in or on mammalian tissue. In additional aspects, devices and/or methods disclosed herein may be used to modulate nitric oxide for inhibiting 5α-reductase in mammalian tissue. In additional aspects, devices and/or methods disclosed herein may be used to modulate nitric oxide to promote collagen synthesis. In additional aspects, devices and/or methods disclosed herein may be used to increase NO to levels suitable to induce cell death. In further aspects, devices and/or methods disclosed herein may be used for generation of, or promoting reaction with, reactive oxygen species and free radicals. In additional aspects, devices and/or methods disclosed herein may be used to increase vasodilation and decrease inflammation.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Other aspects, features and embodiments of the invention will be more fully apparent from the ensuing disclosure and the appended claims.

BRIEF DESCRIPTION OF DRAWINGS

FIG. 26 is a side cross-sectional schematic view of a portion of a device for delivering light energy to living mammalian tissue, wherein the device is edge lit along multiple edges with multiple light emitting sources supported by a flexible PCB having a reflective surface, other non-light-transmitting surfaces of the device are further bounded by the flexible PCB, the flexible PCB and light emitting sources are covered with an encapsulant material, and a wavelength conversion material is distributed in the encapsulant material.

FIG. 27 is a side cross-sectional schematic view of a portion of a device for delivering light energy to living mammalian tissue, wherein the device is edge lit along multiple edges with multiple light emitting sources supported by a flexible PCB having a reflective surface, other non-light-transmitting surfaces of the device are further bounded by the flexible PCB with raised light extraction features being supported by the flexible PCB, and encapsulant material is provided over the flexible PCB, the light emitting sources, and the light extraction features.

FIG. 28 is a side cross-sectional schematic view of a portion of a device for delivering light energy to living mammalian tissue, wherein the device is edge lit along multiple edges with multiple light emitting sources supported by a flexible PCB having a reflective surface, other non-light-transmitting surfaces of the device are further bounded by the flexible PCB, an encapsulant material is arranged above and below the PCB and over the light emitting sources, and holes or perforations are defined through both the substrate and the encapsulant material.

FIG. 29A is a cross-sectional view of a first exemplary hole definable through a device for delivering light energy to living mammalian tissue, the hole having a diameter that is substantially constant with depth.

FIG. 29B is a cross-sectional view of a second exemplary hole definable through a device for delivering light energy to living mammalian tissue, the hole having a diameter that increases with increasing depth.

FIG. 29C is a cross-sectional view of a third exemplary hole definable through a device for delivering light energy to living mammalian tissue, the hole having a diameter that decreases with increasing depth.

FIG. 42 is a schematic elevation view of at least a portion of a light emitting device for delivering light energy to tissue in an internal cavity of a patient according to one embodiment.

FIG. 43A is a schematic elevation view of at least a portion of a light emitting device including a concave light emitting surface for delivering light energy to cervical tissue of a patient according to one embodiment.

FIG. 43B illustrates the device of FIG. 43A inserted into a vaginal cavity to deliver light energy to cervical tissue of a patient.

FIG. 44A is a schematic elevation view of at least a portion of a light emitting device including a probe-defining light emitting surface for delivering light energy to cervical tissue of a patient according to another embodiment.

FIG. 44B illustrates the device of FIG. 44A inserted into a vaginal cavity, with a probe portion of the light-emitting surface inserted into a cervical opening, to deliver light energy to cervical tissue of a patient.

DETAILED DESCRIPTION

Figure 1:
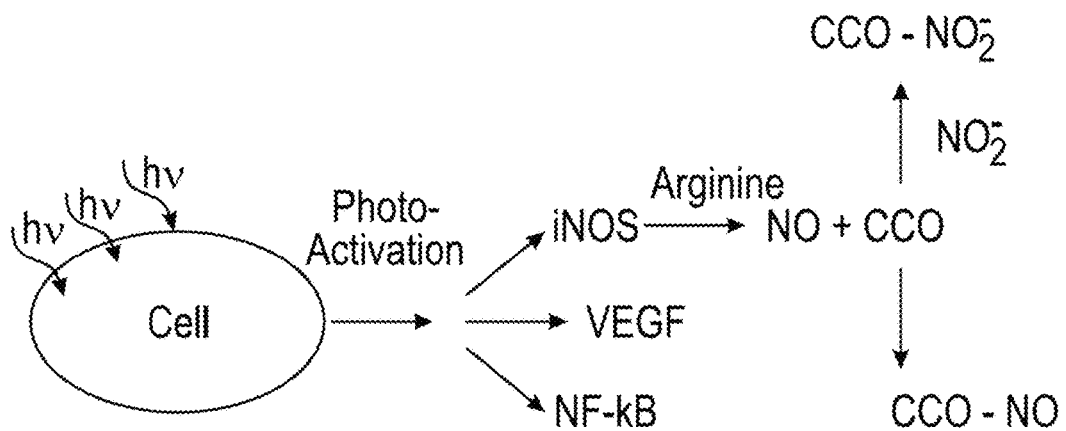
FIG. 1 is a reaction sequence showing photoactivated production of nitric oxide (NO) catalyzed by iNOS, followed by binding of NO to CCO.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

Certain aspects of the disclosure relate to phototherapeutic modulation of nitric oxide in living mammalian tissue, including use of light having a first peak wavelength and a first radiant flux to release nitric oxide from endogenous stores of nitric oxide, and use of light having a second peak wavelength and a second radiant flux to increase endogenous stores of nitric oxide (e.g., to increase expression of nitric oxide synthase enzymes), wherein the second peak wavelength differs from the first peak wavelength. The photoinitiated release of endogenous stores of nitric oxide effectively regenerates "gaseous" (or unbound) nitric oxide that was autooxidized into nitrosative intermediates and bound covalently in the body in a "bound" state. By stimulating release of nitric oxide from endogenous stores, nitric oxide may be maintained in a gaseous state for an extended duration and/or a spatial zone of nitric oxide release may be expanded.

Certain aspects of the disclosure relate to phototherapeutic modulation of nitric oxide in living mammalian tissue, including use of light having a first peak wavelength and a first radiant flux to stimulate enzymatic generation of nitric oxide to increase endogenous stores of nitric oxide (e.g., to increase expression of nitric oxide synthase enzymes), and release nitric oxide from the endogenous stores. The photoinitiated release of endogenous stores of nitric oxide effectively regenerates "gaseous" (or unbound) nitric oxide that was autooxidized into nitrosative intermediates and bound covalently in the body in a "bound" state. By stimulating release of nitric oxide from endogenous stores, nitric oxide may be maintained in a gaseous state for an extended duration and/or a spatial zone of nitric oxide release may be expanded.

Figure 2A:
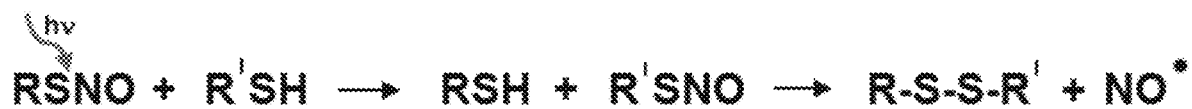
FIG. 2A is a reaction sequence showing photomodulated release of NO from nitrosothiols (RSNO).
Figure 2B:
FIG. 2B is a reaction sequence showing photomodulated release of NO from metal nitrosyls (M-NO).
Figure 2C:
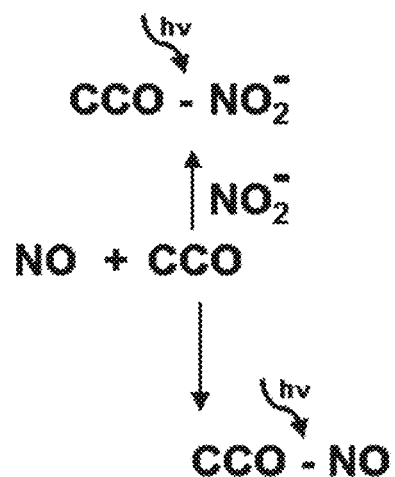
FIG. 2C is a reaction sequence showing loading of cytochrome c oxidase (CCO) with NO (yielding CCO-NO and $CCO-NO_2$) followed by photomodulated release of nitric oxide from the CCO-NO and $CCO-NO_2$.

As noted previously, nitric oxide is endogenously stored on a variety of nitrosated biochemical structures. Upon receiving the required excitation energy, both nitroso and nitrosyl compounds undergo hemolytic cleavage of S—N, N—N, or M-N bonds to yield free radical nitric oxide. Nitrosothiols and nitrosamines are photoactive and can be phototriggered to release nitric oxide by wavelength specific excitation. FIG. 2A is a reaction sequence showing photomodulated release of NO from nitrosothiols (RSNO). Similar results may be obtained with metal nitrosyls and NO-loaded chromophores (such as, but not limited to, CCO-NO). FIG. 2B is a reaction sequence showing photomodulated release of NO from metal nitrosyls (M-NO). FIG. 2C is a reaction sequence showing loading of cytochrome c oxidase (CCO) with NO (yielding CCO-NO and CCO-NO$_2^-$), followed by photomodulated release of nitric oxide from the CCO-NO and CCO-NO$_2^-$. In each case, providing light energy of a specified peak wavelength and radiant flux to tissue may stimulate release of endogenous stores of NO to permit NO to be maintained in a gaseous state in living tissue for a longer duration than would be encountered in the absence of the provision of such light energy.

Figure 3:
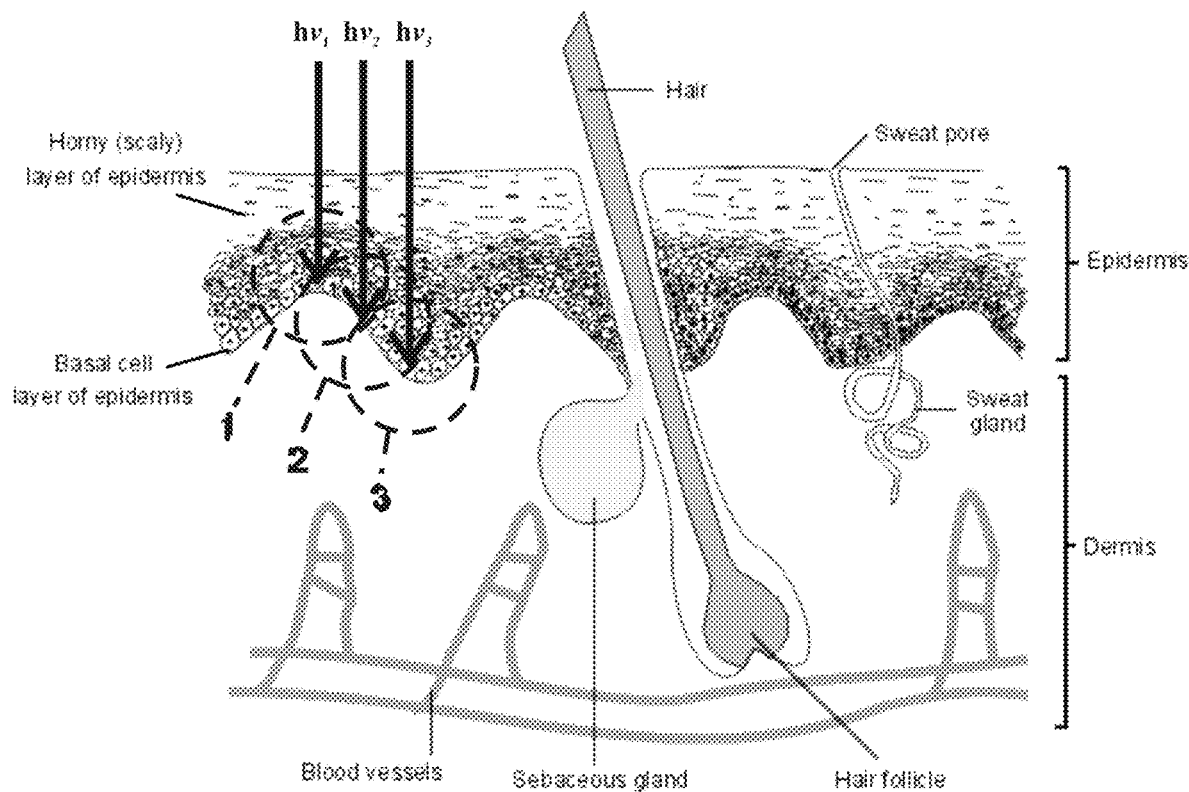
FIG. 3 is a cross-sectional view of epidermis and dermis layers of human skin with schematic illustration of overlapping zones in which NO is released from endogenous stores of NO by photomodulation.

FIG. 3 is a cross-sectional view of epidermis and dermis layers of human skin with schematic illustration of overlapping zones 1-3 in which endogenous stores of NO are generated and/or NO is released from endogenous stores by photomodulation. (The zones 1-3 are not necessarily illustrated to scale.) It has been reported that NO may diffuse in mammalian tissue by a distance of up to about 500 microns. In certain embodiments, photons of a first energy $h\nu_1$ may be supplied to the tissue to stimulate enzymatic generation of NO to increase endogenous stores of NO in a first diffusion zone 1. Photons of a second energy $h\nu_2$ may be supplied to the tissue in a region within or overlapping the first diffusion zone 1 to trigger release of NO from endogenous stores, thereby creating a second diffusion zone 2. Alternatively, or additionally, photons of a second energy $h\nu_2$ may be supplied to stimulate enzymatic generation of NO to increase endogenous stores of NO in the second diffusion zone 2. Photons of a third energy $h\nu_3$ may be supplied to the tissue in a region within or overlapping the second diffusion zone 2 to trigger release of endogenous stores, thereby creating a third diffusion zone 3. Alternatively, or additionally, photons of a third energy $h\nu_3$ may be supplied to stimulate enzymatic generation of NO to increase endogenous stores of NO in the third diffusion zone 3. In certain embodiments, the first, second, and third diffusion zones 1-3 may have different average depths relative to an outer epidermal surface. In certain embodiments, the first photon energy $h\nu_1$, the second photon energy $h\nu_2$, and the third photon energy $h\nu_3$ may be supplied at different peak wavelengths, wherein different peak wavelengths may penetrate mammalian tissue to different depths—since longer wavelengths typically provide greater penetration depth. In certain embodiments, sequential or simultaneous impingement of increasing wavelengths of light may serve to "push" a nitric oxide diffusion zone deeper within mammalian tissue than might otherwise be obtained by using a single (e.g., long) wavelength of light.

Light having a first peak wavelength and a first radiant flux to release nitric oxide from endogenous stores of nitric oxide may be referred to herein as "endogenous store releasing light" or "ES releasing light;" and light having a second peak wavelength and a second radiant flux to stimulate enzymatic generation of nitric oxide to increase endogenous stores of nitric oxide may be referred to herein as "endogenous store increasing light" or "ES increasing light."

In certain embodiments, the second peak wavelength (of the ES increasing light) is greater than the first peak wavelength (of the ES releasing light) by at least 25 nm, at least 40 nm, at least 50 nm, at least 60 nm, at least 75 nm, at least 85 nm, at least 100 nm, or another threshold specified herein.

In certain embodiments, each of the ES increasing light and the ES releasing light has a radiant flux in a range of at least 5 mW/cm$^2$, or at least 10 mW/cm$^2$, or at least 15 mW/cm$^2$, or at least 20 mW/cm$^2$, or at least 30 mW/cm$^2$, or at least 40 mW/cm$^2$, or at least 50 mW/cm$^2$, or in a range of from 5 mW/cm$^2$ to 60 mW/cm$^2$, or in a range of from 5 mW/cm$^2$ to 30 mW/cm$^2$, or in a range of from 5 mW/cm$^2$ to 20 mW/cm$^2$, or in a range of from 5 mW/cm$^2$ to 10 mW/cm$^2$, or in a range of from 10 mW/cm$^2$ to 60 mW/cm$^2$, or in a range of from 20 mW/cm$^2$ to 60 mW/cm$^2$, or in a range of from 30 mW/cm$^2$ to 60 mW/cm$^2$, or in a range of from 40 mW/cm$^2$ to 60 mW/cm$^2$, or in another range specified herein.

In certain embodiments, the ES increasing light has a greater radiant flux than the ES releasing light. In certain embodiments, the ES releasing light has a greater radiant flux than the ES increasing light.

In certain embodiments, one or both of the ES increasing light and the ES releasing light has a radiant flux profile that is substantially constant during a treatment window. In certain embodiments, at least one of the ES increasing light and the ES releasing light has a radiant flux profile that increases with time during a treatment window. In certain embodiments, at least one of the ES increasing light and the ES releasing light has a radiant flux profile that decreases with time during a treatment window. In certain embodiments, one of the ES increasing light or the ES releasing light has a radiant flux profile that decreases with time during a treatment window, while the other of the ES increasing light or the ES releasing light has a radiant flux profile that increases with time during a treatment window.

In certain embodiments, ES releasing light is applied to tissue during a first time window, ES increasing light is applied to the tissue during a second time window, and the second time window overlaps with the first time window. In other embodiments, ES releasing light is applied to tissue during a first time window, ES increasing light is applied to the tissue during a second time window, and the second time is non-overlapping or is only partially overlapping with the first time window. In certain embodiments, the second time window is initiated more than one minute, more than 5 minutes, more than 10 minutes, more than 30 minutes, or more than one hour after conclusion of the first time window. In certain embodiments, ES releasing light is applied to tissue during a first time window, ES increasing light is applied to the tissue during a second time window, and the first time window and the second time window are substantially the same. In other embodiments, the second time window is longer than the first time window.

In certain embodiments, one or both of ES increasing light and ES releasing light may be provided by a steady state source providing a radiant flux that is substantially constant over a prolonged period without being pulsed.

In certain embodiments, one or both of ES increasing light and ES releasing light may include more than one discrete pulse (e.g., a plurality of pulses) of light. In certain embodiments, more than one discrete pulse of ES releasing light is impinged on tissue during a first time window, and/or more than one discrete pulse of ES increasing light is impinged on tissue during a second time window. In certain embodiments, the first time window and the second time window may be coextensive, may be overlapping but not coextensive, or may be non-overlapping.

In certain embodiments, at least one of radiant flux and pulse duration of ES releasing light may be reduced from a maximum value to a non-zero reduced value during a portion of a first time window. In certain embodiments, at least one of radiant flux and pulse duration of ES releasing light may be increased from a non-zero value to a higher value during a portion of a first time window. In certain embodiments, at least one of radiant flux and pulse duration of ES increasing light may be reduced from a maximum value to a non-zero reduced value during a portion of a second time window. In certain embodiments, at least one of radiant flux and pulse duration of ES increasing light may be increased from a non-zero value to a higher value during a portion of a second time window.

In certain embodiments, each of ES increasing light and ES releasing light consists of non-coherent light. In certain embodiments, each of ES increasing light and ES releasing light consists of coherent light. In certain embodiments, one of the ES increasing light or the ES releasing light consists of non-coherent light, and the other of the ES increasing light or the ES releasing light consists of coherent light.

In certain embodiments, the ES releasing light is provided by at least one first light emitting device and the ES increasing light is provided by at least one second light emitting device. In certain embodiments, the ES releasing light is provided by a first array of light emitting devices and the ES increasing light is provided by a second array of light emitting devices.

In certain embodiments, at least one of the ES increasing light or the ES releasing light is provided by at least one solid state light emitting device. Examples of solid state light emitting devices include (but are not limited to) light emitting diodes, lasers, thin film electroluminescent devices, powdered electroluminescent devices, field induced polymer electroluminescent devices, and polymer light-emitting electrochemical cells. In certain embodiments, the ES releasing light is provided by at least one first solid state light emitting device and the ES increasing light is provided by at least one second solid state light emitting device. In certain embodiments, ES increasing light and ES releasing light may be generated by different emitters contained in a single solid state emitter package, wherein close spacing between adjacent emitters may provide integral color mixing. In certain embodiments, the ES releasing light may be provided by a first array of solid state light emitting devices and the ES increasing light may be provided by a second array of solid state light emitting devices. In certain embodiments, an array of solid state emitter packages each including at least one first emitter and at least one second emitter may be provided, wherein the array of solid state emitter packages embodies a first array of solid state emitters arranged to generate ES releasing light and embodies a second array of solid state emitters arranged to generate ES increasing light. In certain embodiments, an array of solid state emitter packages may embody packages further including third, fourth, and/or fifth solid state emitters, such that a single array of solid state emitter packages may embody three, four, or five arrays of solid state emitters, wherein each array is arranged to generate emissions with a different peak wavelength.

In certain embodiments, at least one of the ES increasing light or the ES releasing light is provided by at least one light emitting device devoid of a wavelength conversion material. In other embodiments, at least one of the ES increasing light or the ES releasing light is provided by at least one light emitting device arranged to stimulate a wavelength conversion material, such as a phosphor material, a fluorescent dye material, a quantum dot material, and a fluorophore material.

In certain embodiments, the ES increasing light and the ES releasing light consist of substantially monochromatic light. In certain embodiments, the ES releasing light includes a first spectral output having a first full width at half maximum value of less than 25 nm (or less than 20 nm, or less than 15 nm, or in a range of from 5 nm to 25 nm, or in a range of from 10 nm to 25 nm, or in a range of from 15 nm to 25 nm), and/or the ES increasing light includes a second spectral output having a second full width at half maximum value of less than 25 nm (or less than 20 nm, or less than 15 nm, or in a range of from 5 nm to 25 nm, or in a range of from 10 nm to 25 nm, or in a range of from 15 nm to 25 nm). In certain embodiments, less than 5% of the first spectral output is in a wavelength range of less than 400 nm, and less than 1% of the second spectral output is in a wavelength range of less than 400 nm.

In certain embodiments, the ES releasing light is produced by one or more first light emitters having a single first peak wavelength, and the ES increasing light is produced by one or more second light emitters having a single second peak wavelength. In other embodiments, the ES increasing light may be produced by at least two light emitters having different peak wavelengths (e.g., differing by at least 5 nm, at least 10 nm, at least 15 nm, at least 20 nm, or at least 25 nm), and/or the ES releasing light may be produced by at least two light emitters having different peak wavelengths (e.g., differing by at least 5 nm, at least 10 nm, at least 15 nm, at least 20 nm, or at least 25 nm).

Ultraviolet light (e.g., UV-A light having a peak wavelength in a range of from 350 nm to 395 nm, and UV-B light having a peak wavelength in a range of from 320 nm to 350 nm) may be effective as ES increasing or ES releasing light; however, overexposure to ultraviolet light may lead to detrimental health effects including premature skin aging and potentially elevated risk for certain types of cancer. In certain embodiments, UV light (e.g., having peak wavelengths in a range of from 320 nm to 399 nm) may be used as ES increasing or ES releasing light; however, in other embodiments, UV light may be avoided.

In certain embodiments, ES increasing light and ES releasing light are substantially free of UV light. In certain embodiments, less than 5% of the ES increasing light is in a wavelength range of less than 400 nm, and less than 1% of the ES releasing light output is in a wavelength range of less than 400 nm. In certain embodiments, ES increasing light includes a peak wavelength in a range of from 400 nm to 490 nm, or from 400 nm to 450 nm, or from 400 nm to 435 nm, or from 400 nm to 420 nm, or from 410 nm to 440 nm, or from 420 nm to 440 nm.

In certain embodiments, ES increasing light may include a wavelength range and flux that may alter the presence, concentration, or growth of pathogens (e.g., bacteria, viruses, fungi, protists, and/or other microbes) in or on living mammalian tissue receiving the light. UV light and near-UV light (e.g., having peak wavelengths from 400 nm to 435 nm, or more preferably from 400 nm to 420 nm) in particular may affect microbial growth. Effects on microbial growth may depend on the wavelength range and dose. In certain embodiments, ES increasing or ES releasing light may include near-UV light having a peak wavelength in a range of from 400 nm to 420 nm to provide a bacteriostatic effect (e.g., with pulsed light having a radiant flux of <9 mW/cm$^2$), provide a bactericidal effect (e.g., with substantially steady state light having a radiant flux in a range of from 9 mW/cm$^2$ to 17 mW/cm$^2$), or provide an antimicrobial effect (e.g., with substantially steady state light having a radiant flux in a range of greater than 17 mW/cm$^2$, such as in a range of from 18 mW/cm$^2$ to 60 mW/cm$^2$). In certain embodiments, ES increasing or ES releasing light in a near-UV range (e.g., from 400 nm to 420 nm) may also affect microbial growth (whether in a bacteriostatic range, bactericidal range, or an antimicrobial range) for uses such as wound healing, reduction of acne blemishes, or treatment of atopic dermatitis. Such function(s) may be in addition to the function of the ES increasing light to increase endogenous stores of nitric oxide in living tissue.

In certain embodiments, ES increasing light may include a peak wavelength in a range of from 500 nm to 900 nm, or in a range of from 490 nm to 570 nm, or in a range of from 510 nm to 550 nm, or in a range of from 520 nm to 540 nm, or in a range of from 525 nm to 535 nm, or in a range of from 528 nm to 532 nm, or in a range of about 530 nm.

Applicant has found that the ability to generate and release nitric oxide is dependent on the wavelength and fluence of light used. To investigate whether certain wavelengths of light may be more effective than others at releasing endogenous stores of NO (i.e., to serve as ES releasing light), Applicant performed various experiments. One series of experiments included generating nitric oxide-loaded hemoglobin (Hb-NO), irradiating the Hb-NO with different wavelengths of light produced by substantially monochromatic LEDs, and comparing absorbance spectra for Hb, for the Hb-NO prior to the LED irradiation, and for the Hb-NO after the LED irradiation. The Hb-NO was generated by mixing 10 μM Hb with 1 μM Prolino (a NO source). The mixture was then stirred and incubated one hour, and then was allowed to rest for 5 minutes. Irradiation with LED light was performed under vacuum to facilitate removal of NO liberated from the Hb-NO.

Figure 4A:
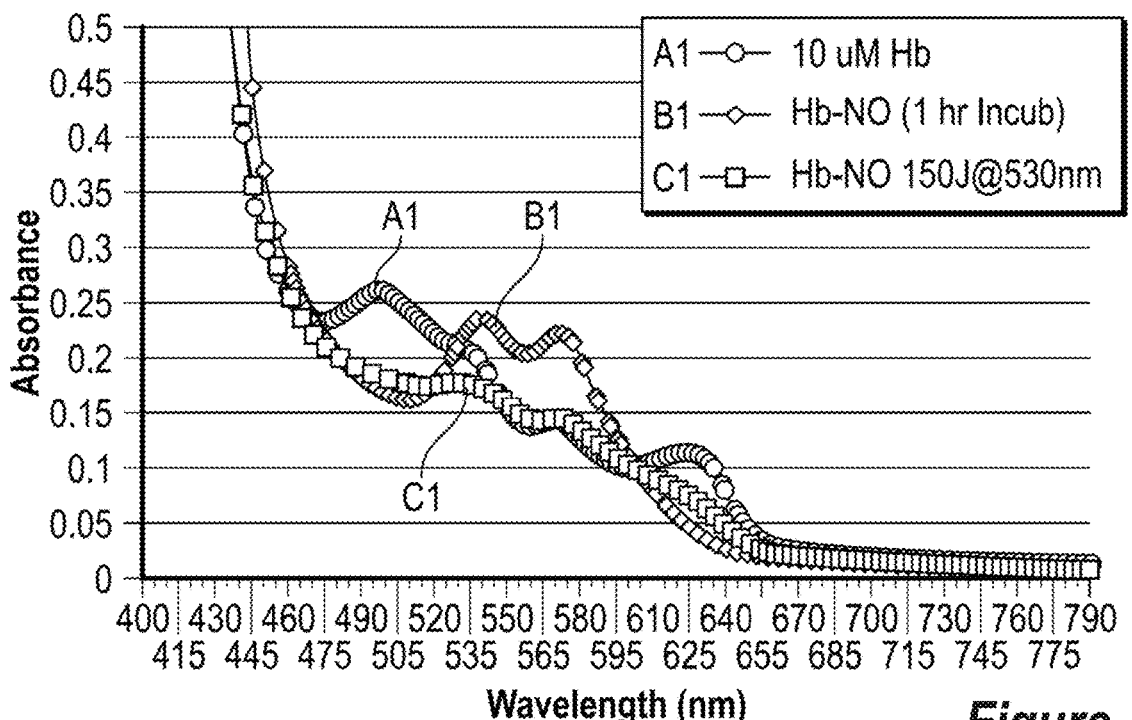
FIG. 4A includes superimposed plots of absorbance versus wavelength for hemoglobin (Hb), nitric oxide-loaded hemoglobin (Hb-NO) prior to irradiation, and Hb-NO following absorption of 150 J of light emissions of a green LED having a peak wavelength of 530 nm.

FIG. 4A includes superimposed plots of absorbance versus wavelength for hemoglobin (Hb) (line "A1"), for nitric oxide-loaded hemoglobin (Hb-NO) prior to irradiation (line "B1"), and for Hb-NO following absorption of 150 J of light emissions of a green LED having a peak wavelength of 530 nm (line "C1"). A comparison of line A1 and line B1 shows the presence of two peaks at about 540 nm and about 577 nm, representing the presence of NO in the Hb-NO. A comparison of line C1 and line B1 shows that the two peaks at about 540 nm and about 577 nm present in the Hb-NO were eliminated, thereby evidencing release of NO from the Hb-NO attributable to irradiation of Hb-NO with 530 nm peak wavelength green light.

Figure 4B:
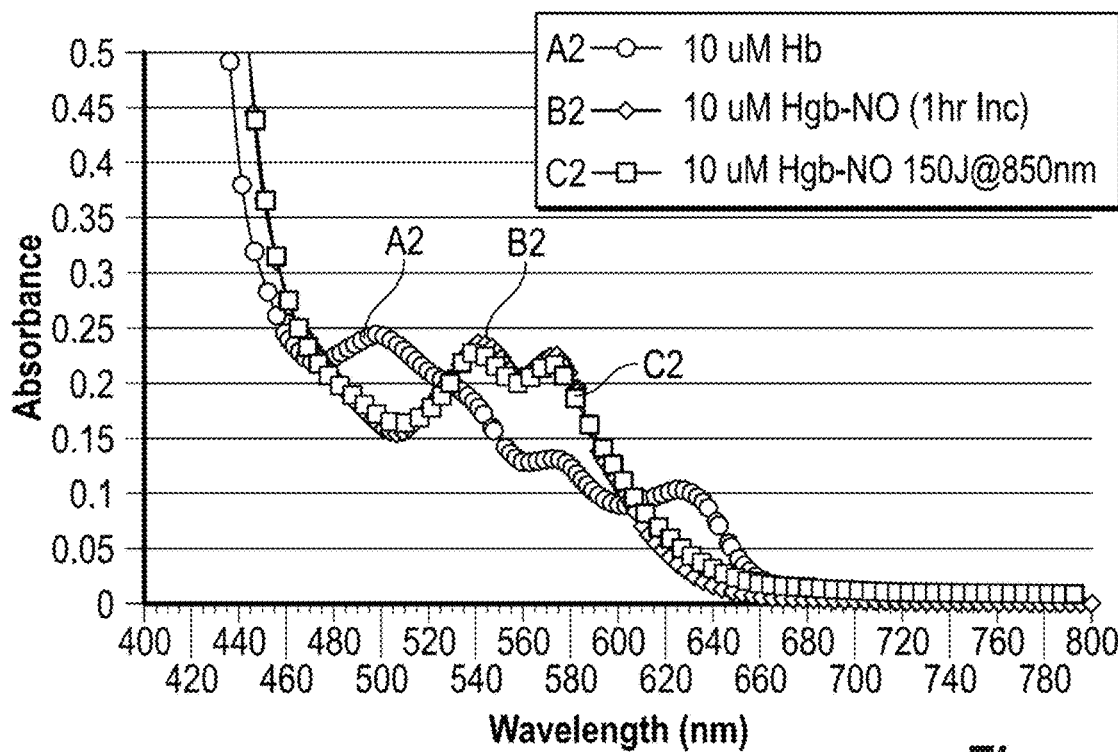
FIG. 4B includes superimposed plots of absorbance versus wavelength for Hb, Hb-NO prior to irradiation, and Hb-NO following absorption of 150 J of light emissions of an IR LED source having a peak wavelength of 850 nm.

FIG. 4B includes superimposed plots of absorbance versus wavelength for Hb (line "A2"), for Hb-NO prior to irradiation (line "B2"), and for Hb-NO following absorption of 150 J of light emissions of an IR LED source having a peak wavelength of 850 nm (line "C2"). A comparison of line A2 and line B2 shows the presence of two peaks at about 540 nm and about 577 nm, representing the presence of NO in the Hb-NO. A comparison of lines C1 and B1, however, reveals that such lines substantially coincide with one another. This evidences that impingement of 850 nm peak wavelength light on Hb-NO was ineffective in releasing NO.

Figure 5:
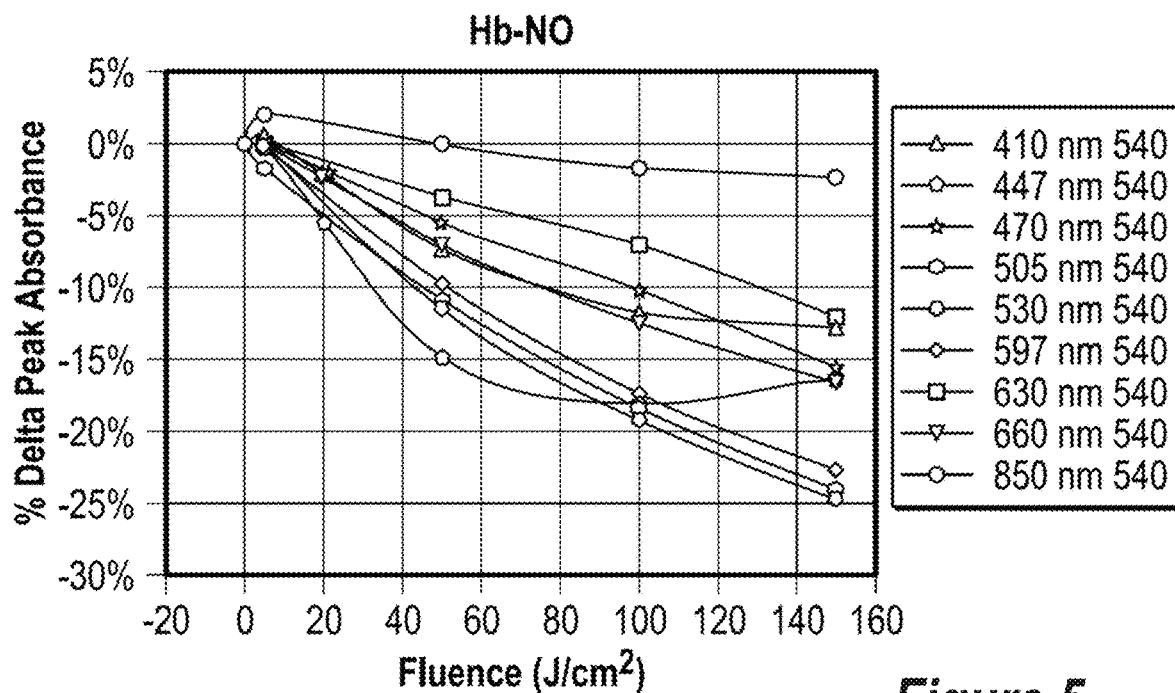
FIG. 5 is a plot of percentage change in peak absorbance for the 540 nm peak of Hb-NO versus fluence (Joules per square centimeter) for nine different wavelengths of light (from 410 nm to 850 nm).

Nine LED light sources providing nine different peak wavelengths (i.e., 410 nm, 447 nm, 470 nm, 505 nm, 530 nm, 597 nm, 630 nm, 660 nm, and 850 nm) were tested to determine their relative effectiveness in releasing NO from Hb-NO. FIG. 5 is a plot of percentage change in peak absorbance for the 540 nm peak of Hb-NO versus fluence (Joules per square centimeter) for the nine different wavelengths of light from 410 nm to 850 nm. As shown in FIG. 5, the wavelengths identified to be most effective in releasing NO from Hb-NO were determined to be the following, from best to worst: 530 nm, 505 nm, 597 nm, 447 nm, 660 nm, 470 nm, 410 nm, 630 nm, and 850 nm.

Figure 6:
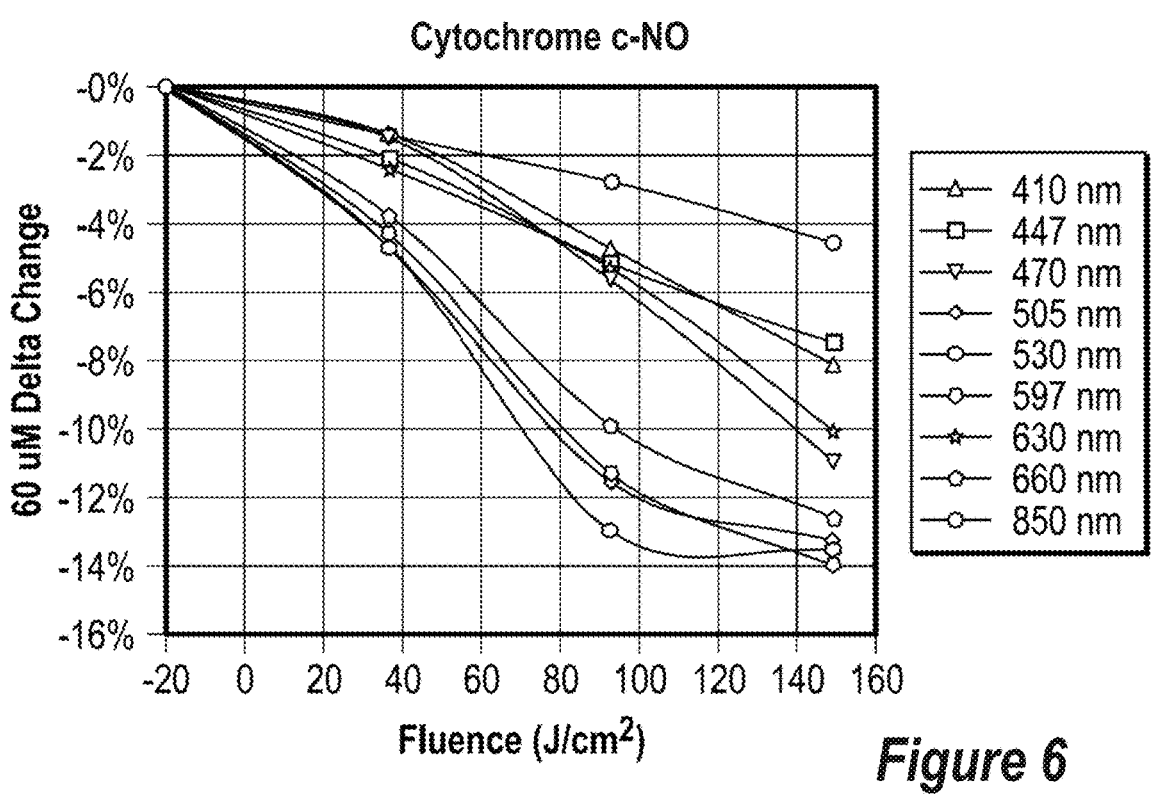
FIG. 6 is a plot of percentage change in peak absorbance for Cytochrome c-NO versus fluence (Joules per square centimeter) for nine different wavelengths of light (from 410 nm to 850 nm).

Another series of experiments included generating nitric oxide-loaded cytochrome c (Cytochrome c-NO), irradiating the Cytochrome c-NO with different wavelengths of light produced by substantially monochromatic LEDs, and comparing absorbance spectra for Cytochrome c, for the Cytochrome c-NO prior to the LED irradiation, and for the Cytochrome c-NO after the LED irradiation. 60 µM Cytochrome c was used according to a procedure otherwise similar to that described above in connection with Hb. FIG. 6 is a plot of percentage change in peak absorbance for Cytochrome c-NO versus fluence (Joules per square centimeter) for nine different wavelengths of light (from 410 nm to 850 nm). As shown in FIG. 6, the wavelengths identified to be most effective in releasing NO from Cytochrome c-NO were determined to be the following, from best to worst: 530 nm, 597 nm, 505 nm, 660 nm, 470 nm, 630 nm, 410 nm, 447 nm, and 850 nm. Notably, 530 nm was determined to be the most effective peak wavelength of light for releasing NO from both Hb-NO and Cytochrome c-NO.

Figure 7:
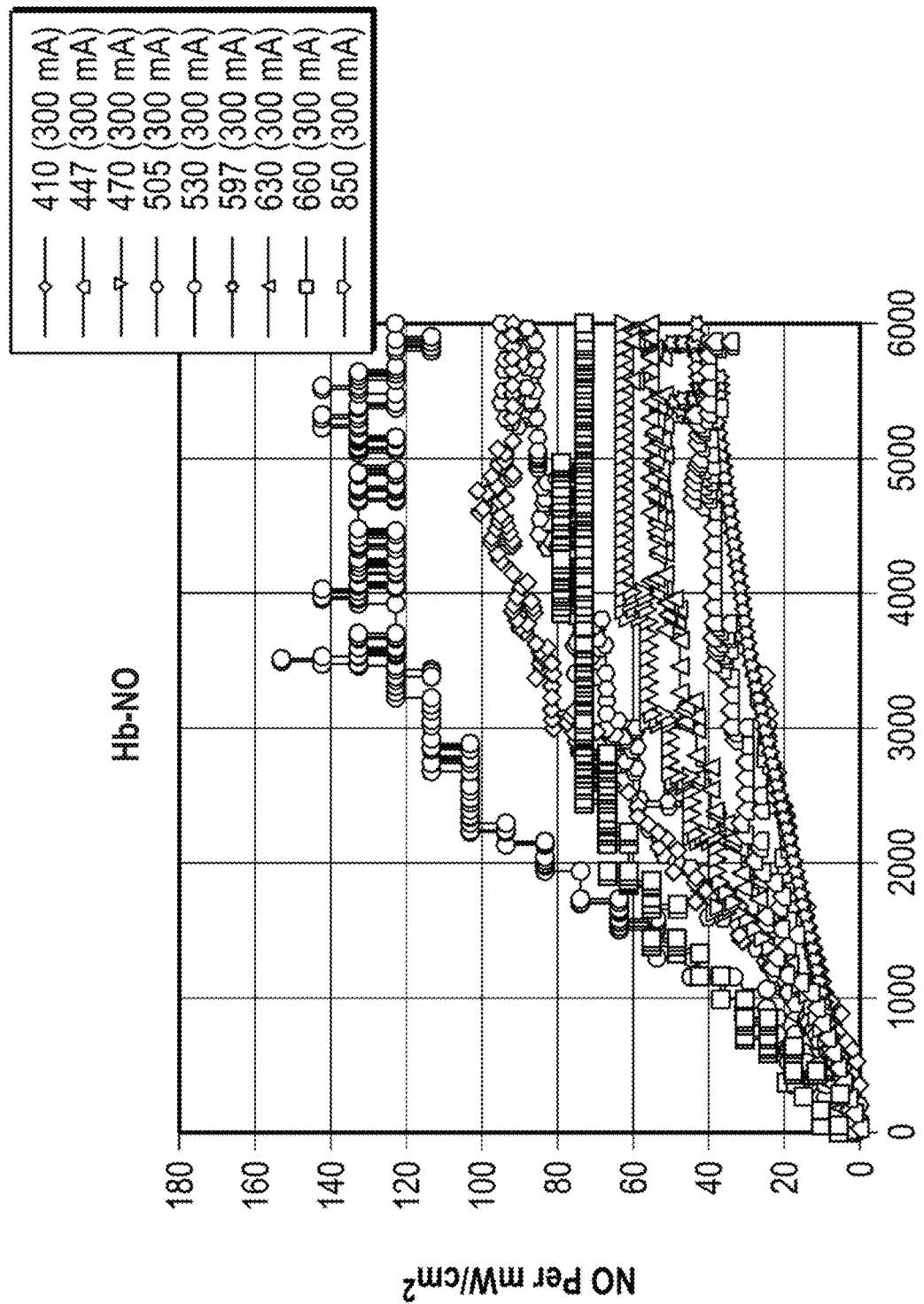
FIG. 7 is a plot of released NO (ppb) per milliwatt per square centimeter versus time for the photomodulated release of NO from Hb-NO for nine different wavelengths of light (from 410 nm to 850 nm).

The results shown in FIG. 5 for Hb-NO were not normalized to radiant flux, and it is recognized that different LEDs have different efficiencies. To address this issue, the results for Hb-NO were normalized to a 300 mA value. FIG. 7 is a plot of released NO per milliwatt per square centimeter versus time for the photomodulated release of NO from Hb-NO for nine different wavelengths of light (from 410 nm to 850 nm). As shown in FIG. 7, 530 nm was determined to be the single most efficient single peak wavelength (per milliwatt of power) for releasing NO from Hb-NO.

To determine whether various combinations of two peak wavelengths might be more or less effective than single peak wavelengths in releasing NO from Hb-NO, additional experiments were performed using Hb-NO. Hb-NO was generated by mixing 10 µM Hb with 1 µM Prolino (a NO source), then the mixture was stirred and incubated one hour, and the mixture was allowed to rest for 5 minutes. Irradiation with two peak wavelengths of LED light was performed under vacuum to facilitate removal of NO liberated from the Hb-NO. Results for three different combinations of two peak wavelengths are shown in FIGS. 8A to 8C, together with results obtained for individual constituents of the combinations.

Figure 8A:
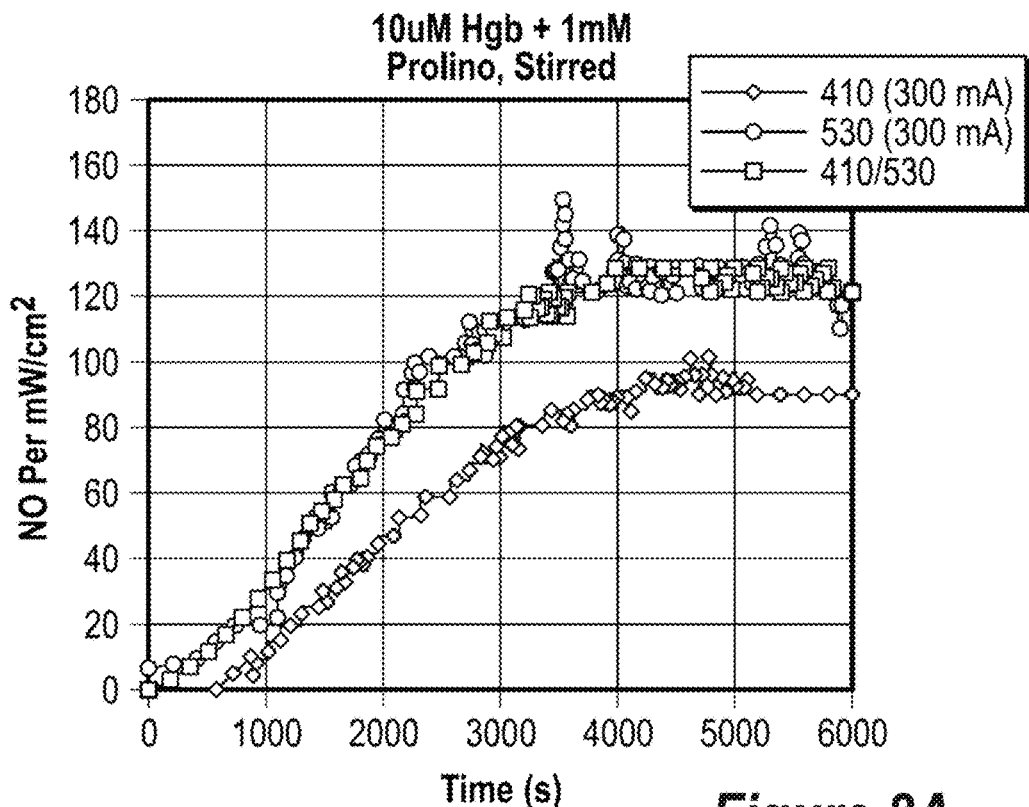
FIG. 8A includes superimposed plots of released NO (ppb) per milliwatt per square centimeter versus time for irradiation of Hb-NO with (i) a 410 nm peak wavelength blue LED device, (ii) a 530 nm peak wavelength green LED device, and (iii) the 410 nm peak wavelength blue LED device in combination with the 530 nm peak wavelength green LED device.

FIG. 8A includes superimposed plots of released NO per milliwatt per square centimeter versus time for irradiation of Hb-NO with (i) a 410 nm peak wavelength blue LED device, (ii) a 530 nm peak wavelength green LED device, and (iii) the 410 nm peak wavelength blue LED device in combination with the 530 nm peak wavelength green LED device. As expected from the prior experiments, the 410 nm light was significantly less effective than the 530 nm light at releasing NO from Hb-NO. Surprisingly, however, the combination of equal parts of 410 nm light and 530 nm light appeared to be equally as effective as 530 nm light alone. Such a combination may be beneficial since a 410 nm blue LED is significantly more efficient than a 530 nm green LED, such that a combination of equal parts of 410 nm LED emissions and 530 nm LED emissions may use 26% less electric power than emissions of a 530 nm LED alone, when operated to provide the same radiant flux.

Figure 8B:
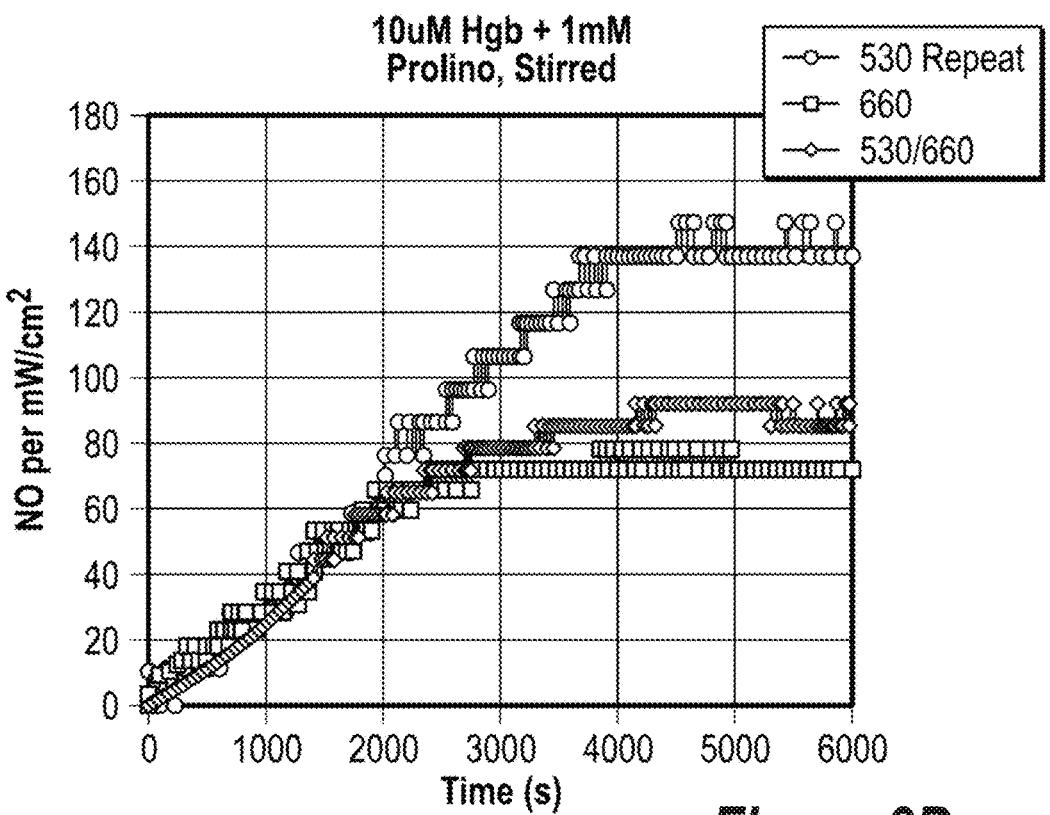
FIG. 8B includes superimposed plots of released NO (ppb) per milliwatt per square centimeter versus time for irradiation of Hb-NO with (i) a 530 nm peak wavelength green LED device, (ii) a 660 nm peak wavelength red LED device, and (iii) the 530 nm peak wavelength green LED device in combination with the 660 nm peak wavelength red LED device.
Figure 8C:
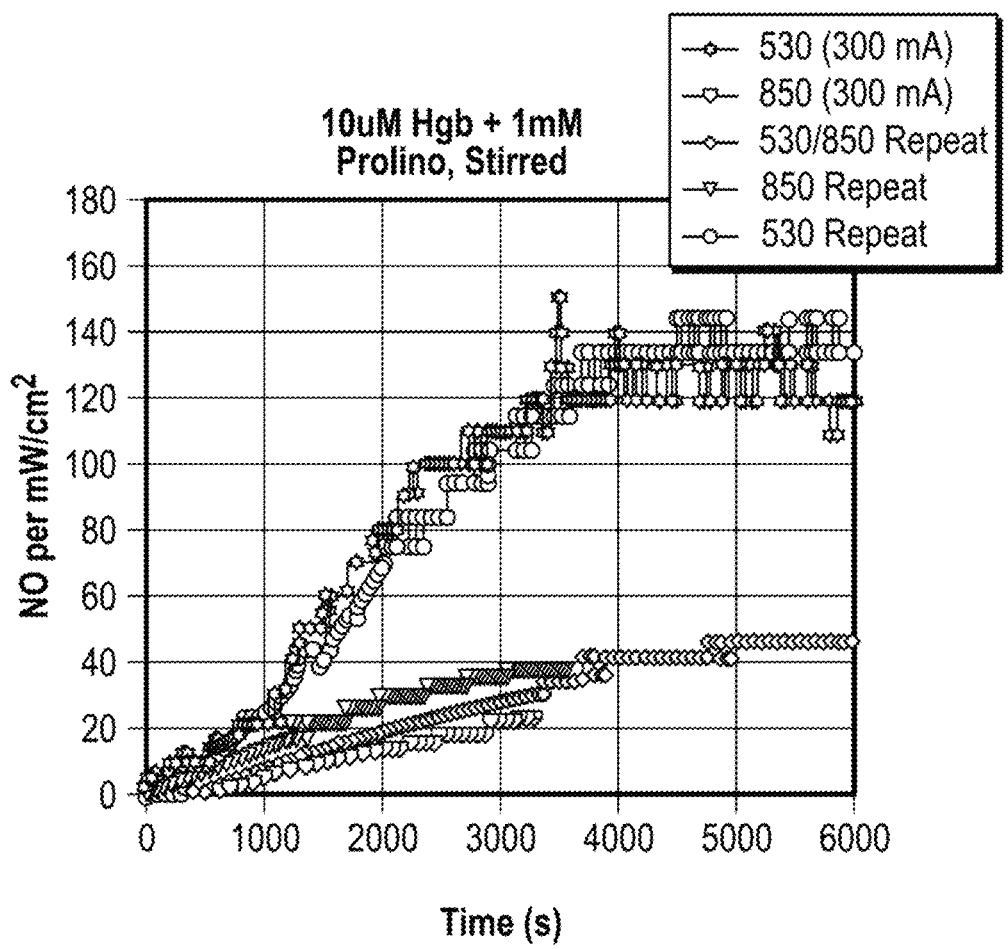
FIG. 8C includes superimposed plots of released NO (ppb) per milliwatt per square centimeter versus time for irradiation of Hb-NO with (i) a 530 nm peak wavelength green LED device (including one repeat run), (ii) a 850 nm peak wavelength infrared LED device (including one repeat run), and (iii) the 530 nm peak wavelength green LED device in combination with the 850 nm peak wavelength infrared LED device.

FIG. 8B includes superimposed plots of released NO per milliwatt per square centimeter versus time for irradiation of Hb-NO with (i) a 530 nm peak wavelength green LED device, (ii) a 660 nm peak wavelength red LED device, and (iii) the 530 nm peak wavelength green LED device in combination with the 660 nm peak wavelength red LED device. As expected from the prior experiments, the 660 nm red light was significantly less effective than the 530 nm green light at releasing NO from Hb-NO. The combination of equal parts of 530 nm green light and 660 nm red light was only slightly better than 660 nm red light alone at releasing NO from Hb-NO.

Notably, as shown in FIG. 8B, the release of NO from Hb-NO appears to be the same for 530 nm green light, 660 nm red light, and a combination of 530 nm green and 660 nm light for the time window of from 0 seconds to about 2000 seconds, but the effectiveness of the different sources diverges thereafter. Without intending to be bound by any particular theory or explanation of this phenomenon, it is suggested that NO binds to Hb-NO at multiple sites, and that removal of a second or subsequent NO molecule from Hb-NO may require more energy than removal of a first NO molecule, perhaps due to a change in shape of the Hb-NO after removal of a first NO molecule.

FIG. 8C includes superimposed plots of released NO per milliwatt per square centimeter versus time for irradiation of Hb-NO with (i) a 530 nm peak wavelength green LED device (including one repeat run), (ii) a 850 nm peak wavelength infrared LED device (including one repeat run), and (iii) the 530 nm peak wavelength green LED device in combination with the 850 nm peak wavelength infrared LED device. As expected from the prior experiments, the 850 nm infrared light was ineffective at releasing NO from Hb-NO. The combination of equal parts of 530 nm green light and 850 nm infrared light was also ineffective at releasing NO from Hb-NO. This shows that the addition of 530 nm green light was unable to enhance the effectiveness of 850 nm infrared light in releasing NO from Hb-NO.

In certain embodiments, ES releasing light that includes light having a first peak wavelength is impinged on living tissue, ES increasing light that includes light having a second peak wavelength is impinged on the living tissue, and furthermore a light having a third peak wavelength may be impinged on the living tissue. In certain embodiments, the light having a third peak wavelength may be provided at substantially the same time as (or during a time window overlapping at least one time window of) one or both of the ES increasing light and the ES releasing light. In certain embodiments, the light having a third peak wavelength differs from each of the first peak wavelength and the second peak wavelength by at least 10 nm. In certain embodiments, the light having a third peak wavelength exceeds the second peak wavelength by at least 20 nm. In certain embodiments, the light having a third peak wavelength is provided with a radiant flux in a range of from 5 mW/cm$^2$ to 60 mW/cm$^2$. In certain embodiments, the third peak wavelength is in a range of from 600 nm to 900 nm, or in a range of from 600 nm to 700 nm. In certain embodiments, the third peak wavelength is in a range of from 320 nm to 399 nm.

In certain embodiments, light having a third peak wavelength in a range of from 620 nm to 670 nm (e.g., including specific wavelengths of about 630 nm and about 660 nm) may be useful to provide anti-inflammatory effects and/or to promote vasodilation. Anti-inflammatory effects may be useful to promote wound healing, to reduce acne blemishes, to promote facial aesthetics, and/or to treat atopic dermatitis and other topical dermatological disorders. Vasodilation may also be beneficial to treat androgenic alopecia or other topical dermatological disorders.

In certain embodiments, light having a third peak wavelength may be useful to promote thermal and/or infrared heating of living mammalian tissue, such as may be useful in certain contexts including wound healing.

In certain embodiments utilizing modulated light therapy to control NO generation and release, human immune response may be altered and/or controlled. Such responses may include, but are not limited to: ATP production; DNA and RNA synthesis; gene transcription; extracellular matrix (e.g., collagen and elastin) secretion; protein expression (including but not limited to NOS enzymes); cell signaling pathways (including cytokine expression (e.g., interleukins), growth factors (e.g., vascular endothelial growth factor, insulin growth factor, insulin-like growth factors, fibroblast growth factors, and tumor necrosis factors); Wnt signaling pathways; and NF-kB pathways); cellular viability; cellular apoptosis; cellular proliferation and migration; reactive oxygen species generation; cellular response to reactive oxygen species (e.g., expression of superoxide dismutase); and inhibition of the enzyme 5α-reductase (to decrease DHT production and thereby reduce or reverse hair loss).

Methods and devices disclosed herein for photomodulation of nitric oxide in living mammalian tissue are contemplated for use with a wide variety of tissues. In certain embodiments, the tissue comprises epithelial tissue. In certain embodiments, the tissue comprises mucosal tissue. In certain embodiments, the tissue is within a body cavity of a patient. In certain embodiments, the tissue comprises cervical tissue.

In certain embodiments, the impinging of light having a first peak wavelength and the impinging of light having a second peak wavelength is performed with a single therapeutic device.

In certain embodiments, a device for photomodulation of nitric oxide in living mammalian tissue as disclosed herein may include a flexible substrate supporting one or more light emitting elements and arranged to conform to at least a portion of a human body. In certain embodiments, a flexible substrate may include a flexible printed circuit board (PCB), such as may include at least one polyimide-containing layer and at least one layer of copper or another electrically conductive material. In other embodiments, a device for photomodulation of nitric oxide as disclosed herein may include a rigid substrate supporting one or more light emitting elements. In certain embodiments, one or more surfaces of a device for photomodulation of nitric oxide may include a light-transmissive encapsulant material arranged to cover any light emitter(s) and at least a portion of an associated substrate (e.g., flexible PCB). A preferred encapsulant material is silicone, which may be applied by any suitable means such as molding, dipping, spraying, dispensing, or the like. In certain embodiments, one or more functional materials may be added to or coated on an encapsulant material. In certain embodiments, at least one surface, or substantially all surfaces (e.g., front and back surfaces) of a flexible PCB may be covered with encapsulant material.

In certain embodiments, a substrate as described herein may be arranged to support one or more light emitting elements. In certain embodiments, one or more light emitting elements may include multi-emitting light emitting devices such as multi-LED packages. In certain embodiments, one or more light emitting elements may be arranged for direct illumination, wherein at least a portion of emissions generated by the one or more light emitting elements is arranged to be transmitted directly through a light-transmissive external surface of a device without need for an intervening waveguide or reflector. In certain embodiments, one or more light emitting elements may be arranged for indirect illumination (e.g., side illumination), wherein emissions generated by the one or more light emitting elements are arranged to be transmitted to a light-transmissive external surface via a waveguide and/or a reflector, without a light emitting element being in direct line-of-sight arrangement relative to a light-transmissive external surface. In certain embodiments, a hybrid configuration may be employed, including one or more light emitting elements arranged for direct illumination, and further including one or more light emitting elements arranged for indirect illumination. In certain embodiments, one or more reflective materials (e.g., reflective flexible PCB or other reflective films) may be provided along selected surfaces of a device to reduce internal absorption of light and to direct light emissions toward an intended light-transmissive surface. In certain embodiments, a flexible light emitting device may include a substantially uniform thickness. In other embodiments, a flexible light emitting device may include a thickness that varies with position, such as a thickness that tapers in one direction or multiple directions. In certain embodiments, presence of a tapered thickness may help a flexible light emitting device to more easily be wrapped against or to conform to areas of a mammalian (e.g., human) body.

In certain embodiments, one or multiple holes or perforations may be defined in a substrate and any associated encapsulant material. In certain embodiments, holes may be arranged to permit transit of air, such as may be useful for thermal management. In certain embodiments, holes may be arranged to permit transit of wound exudate. In certain embodiments, one or more holes may be arranged to permit sensing of at least one condition through the hole(s). Holes may be defined by any suitable means such as laser perforation, die pressing, slitting, punching, blade cutting, and roller perforation. In certain embodiments, holes may have uniform or non-uniform size, placement, and/or distribution relative to a substrate and encapsulant material.

In certain embodiments, a device for photomodulation of nitric oxide in living mammalian tissue as disclosed herein may include one or more light-affecting elements such as one or more light extraction features, wavelength conversion materials, light diffusion or scattering materials, and/or light diffusion or scattering features. In certain embodiments, one or more light affecting elements may be arranged in a layer between a light emitting element and a light transmissive surface of a device. In certain embodiments, an encapsulant material (e.g., encapsulant material layer) may be arranged between at least one light emitting element and one or more light affecting elements. In certain embodiments, one or more light affecting elements may be formed or dispersed within an encapsulant material.

In certain embodiments, impingement of light on living tissue and/or operation of a device as disclosed herein may be responsive to one or more signals generated by one or more sensors or other elements. Various types of sensors are contemplated, including temperature sensors, photosensors, image sensors, proximity sensors, pressure sensors, chemical sensors, biosensors, accelerometers, moisture sensors, oximeters, current sensors, voltage sensors, and the like. Other elements that may affect impingement of light and/or operation of a device as disclosed herein include a timer, a cycle counter, a manually operated control element, a wireless transmitter and/or receiver (as may be embodied in a transceiver), a laptop or tablet computer, a mobile phone, or another portable electronic or digital device external to a lighting device. Wired and/or wireless communication between a device as disclosed herein and one or more signal generating or signal receiving elements may be provided.

In certain embodiments, impingement of light on living tissue and/or operation of a device as disclosed herein may be responsive to one or more temperature signals. For example, a temperature condition may be sensed on or proximate to (a) a device arranged to emit ES increasing light and/or ES releasing light or (b) the tissue; at least one signal indicative of the temperature condition may be generated; and operation of a lighting device may be controlled responsive to the at least one signal. Such control may include initiation of operation, deviation (or alteration) of operation, or termination of operation of light emitting elements, such as elements arranged to emit ES increasing light and/or ES releasing light. In certain embodiments, thermal foldback protection may be provided at a threshold temperature (e.g., >42° Celsius) to prevent a user from experiencing burns or discomfort. In certain embodiments, thermal foldback protection may trigger a light emitting device to terminate operation, reduce current, or change an operating state in response to receipt of a signal indicating an excess temperature condition.

In certain embodiments, a device for modulating nitric oxide in living mammalian tissue as disclosed herein may be used for wound care, and may include one or more sensors. In certain embodiments, one or more light emitters and photodiodes may be provided to illuminate a wound site with one or more selected wavelengths (e.g., green light) to detect blood flow in or proximate to the wound site to provide photoplethsmyography data. One sensor or multiple sensors may be provided. A device may alternatively or additionally include sensors arranged to detect blood pressure, bandage or dressing covering pressure, heart rate, temperature, presence or concentration of chemical or biological species (e.g., in wound exudate), or other conditions.

In certain embodiments, a device for modulating nitric oxide in living mammalian tissue as disclosed herein may include a memory element to store information indicative of one or more sensor signals. Such information may be used for diagnosis, assessing patient compliance, assessing patient status, assessing patient improvement, and assessing function of the device. In certain embodiments, information indicative of one or more sensor signals may be transmitted via wired or wireless means (e.g., via Bluetooth, WiFi, Zigbee, or another suitable protocol) to a mobile phone, a computer, a data logging device, or another suitable device that may optionally be connected to a local network, a wide-area network, a telephonic network, or other communication network. In certain embodiments, a data port (e.g., micro USB or other type) may be provided to permit extraction or interrogation of information contained in a memory.

Details of illustrative devices that may be used for modulating nitric oxide in living mammalian tissue are described hereinafter.

Figure 9:
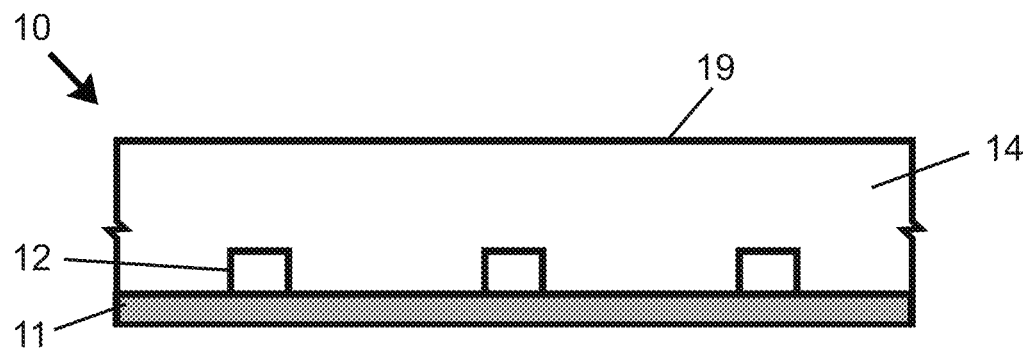
FIG. 9 is a side cross-sectional schematic view of a portion of a device for delivering light energy to living mammalian tissue, the device including multiple direct view light emitting sources supported by a substrate and covered with an encapsulant material layer.

FIG. 9 is a side cross-sectional schematic view of a portion of a device 10 for delivering light energy to living mammalian tissue, the device 10 including multiple direct view light emitting sources 12 supported by a substrate 11 and covered with an encapsulant material 14, which may be embodied in a sheet or layer. The substrate 11 preferably includes a flexible PCB, which may include a reflective surface to reflect light toward a light-transmissive outer surface 19 of the device 10. As shown in FIG. 9, the encapsulant material 14 covers the light emitting sources 12 and an upper surface of the substrate 11; however, it is to be appreciated that in certain embodiments the encapsulant material 14 may cover both upper and lower surfaces of the substrate 11. In certain embodiments, different light emitting sources 12 may generate light having different peak wavelengths. In certain embodiments, one or more light emitting sources 12 may include a multi-emitter package arranged to generate one or multiple peak wavelengths of light. In certain embodiments, one or more light emitting sources 12 may be arranged to produce one or both of ES increasing light and ES releasing light.

Figure 10:
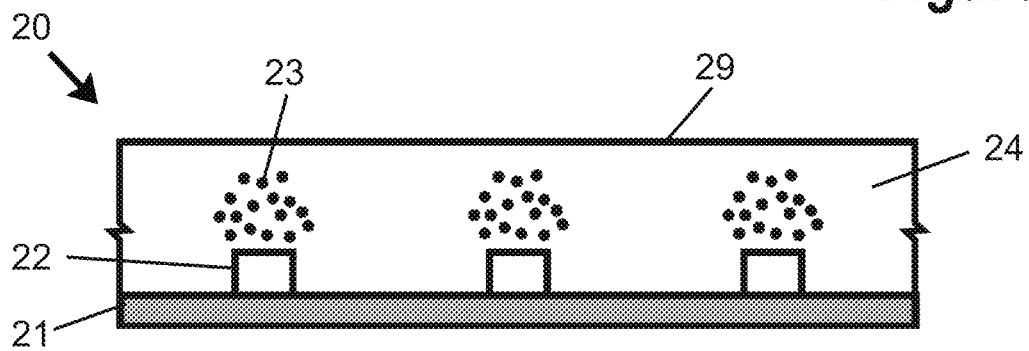
FIG. 10 is a side cross-sectional schematic view of a portion of a device for delivering light energy to living mammalian tissue, the device including multiple direct view light emitting sources supported by a substrate and covered with an encapsulant material layer, wherein at least one functional material (e.g., wavelength conversion and/or scattering material) is disposed within the encapsulant material layer.

FIG. 10 is a side cross-sectional schematic view of a portion of a device 20 for delivering light energy to living mammalian tissue, the device 20 including multiple direct view light emitting sources 22 supported by a substrate 21 and covered with an encapsulant material 24, which may be embodied in a sheet or layer. The substrate 21 preferably includes a flexible PCB, which may include a reflective surface to reflect light toward a light-transmissive outer surface 29 of the device 20. At least one functional material (e.g., wavelength conversion material and/or scattering material) 23 is disposed within the encapsulant material 24. In certain embodiments, the at least one functional material 23 includes one or more wavelength conversion materials, such as at least one of a phosphor material, a fluorescent dye material, a quantum dot material, and a fluorophore material. In certain embodiments, wavelength materials of different peak wavelengths may be applied over different light emitting sources 22. In certain embodiments, the at least one functional material 23 is applied by dispensing or printing. In certain embodiments, one or more light emitting sources 22 may include a multi-emitter package arranged to generate one or multiple peak wavelengths of light. In certain embodiments, one or more light emitting sources 22 may be arranged to produce one or both of ES increasing light and ES releasing light.

Figure 11:
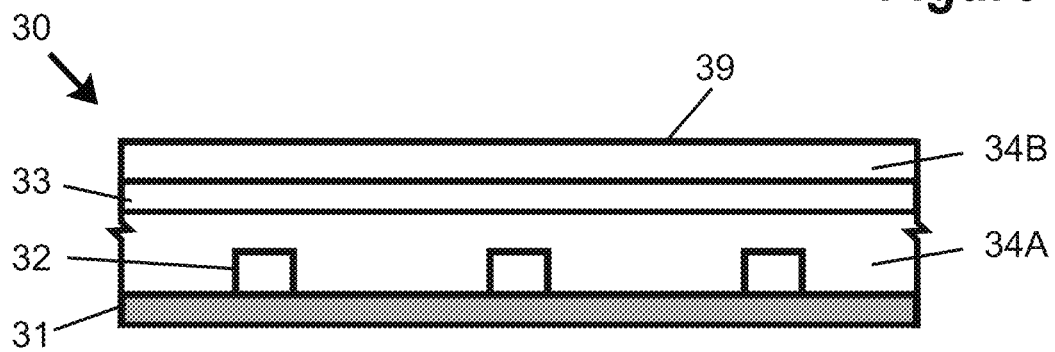
FIG. 11 is a side cross-sectional schematic view of a portion of a device for delivering light energy to living mammalian tissue, the device including multiple direct view light emitting sources supported by a substrate and covered with two encapsulant material layers, with at least one functional material (e.g., wavelength conversion and/or scattering material) layer disposed between the encapsulant material layers.

FIG. 11 is a side cross-sectional schematic view of a portion of a device 30 for delivering light energy to living mammalian tissue, the device 30 including multiple direct view light emitting sources 32 supported by a substrate 31 and covered with two encapsulant material layers 34A, 34B, with at least one functional material (e.g., wavelength conversion and/or scattering material) sheet or layer 33 disposed between the encapsulant material layers 34A, 34B. The substrate 31 preferably includes a flexible PCB, which may include a reflective surface to reflect light toward a light-transmissive outer surface 39 of the device 30. In certain embodiments, the at least one functional material sheet or layer 33 includes one or more wavelength conversion materials, such as at least one of a phosphor material, a fluorescent dye material, a quantum dot material, or a fluorophore material. In certain embodiments, one or more light emitting sources 32 may include a multi-emitter package arranged to generate one or multiple peak wavelengths of light. In certain embodiments, one or more light emitting sources 32 may be arranged to produce one or both of ES increasing light and ES releasing light.

Figure 12:
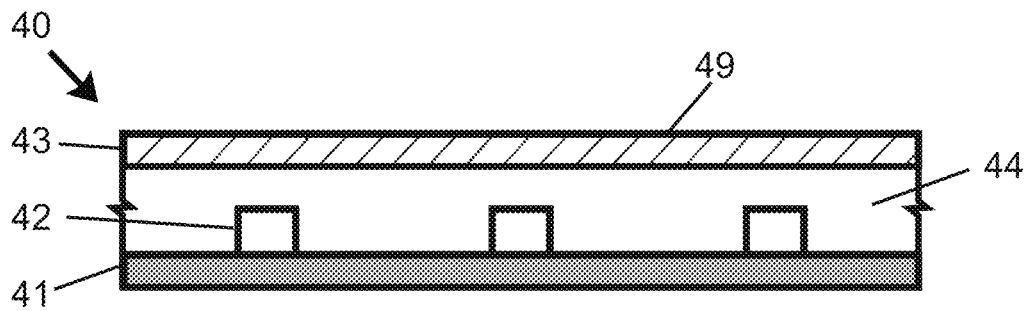
FIG. 12 is a side cross-sectional schematic view of a portion of a device for delivering light energy to living mammalian tissue, the device including multiple direct view light emitting sources supported by a substrate and covered by an encapsulant layer, wherein the encapsulant layer is covered with a diffusion or scattering material layer.

FIG. 12 is a side cross-sectional schematic view of a portion of a device 40 for delivering light energy to living mammalian tissue, the device 40 including multiple direct view light emitting sources 42 supported by a substrate 41 and covered by an encapsulant material 44, which may be embodied in a sheet or layer. The substrate 41 preferably includes a flexible PCB, which may include a reflective surface to reflect light toward a light-transmissive outer surface 49 of the device 40. The encapsulant material 44 is covered with a diffusion or scattering material layer 43. In certain embodiments, the diffusion or scattering material layer 43 may include acrylic, PET-G, silicone, or a polymeric sheet. In certain embodiments, the diffusion or scattering material layer 43 may include scattering particles such as zinc oxide, silicon dioxide, titanium dioxide, or the like. In certain embodiments, one or more light emitting sources 42 may include a multi-emitter package arranged to generate one or multiple peak wavelengths of light. In certain embodiments, one or more light emitting sources 42 may be arranged to produce one or both of ES increasing light and ES releasing light.

Figure 13:
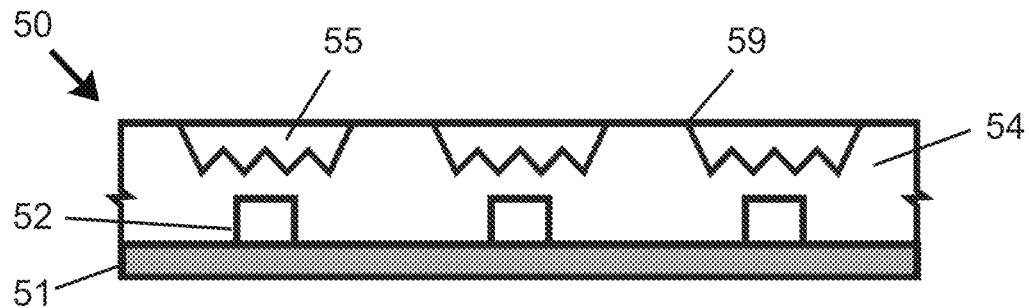
FIG. 13 is a side cross-sectional schematic view of a portion of a device for delivering light energy to living mammalian tissue, the device including multiple direct view light emitting sources supported by a substrate, multiple molded features overlying the light emitting sources, and an encapsulant or light coupling material arranged between the light emitting sources and the molded features.

FIG. 13 is a side cross-sectional schematic view of a portion of a device 50 for delivering light energy to living mammalian tissue, the device 50 including multiple direct view light emitting sources 52 supported by a substrate 51. The substrate 51 preferably includes a flexible PCB, which may include a reflective surface to reflect light toward a light-transmissive outer surface 59 of the device 50. Multiple molded features 55 (e.g., molded from silicone) overlie the light emitting sources 52. An encapsulant or light coupling material 54 is arranged between the light emitting sources 52 and the molded features 55. In certain embodiments, light coupling material 54 may include a light coupling gel with an index of refraction that differs from an index of refraction of the molded features 55. The molded features 55 may be arranged along the light transmissive outer surface 59 of the device 50. In certain embodiments, one or more light emitting sources 52 may include a multi-emitter package arranged to generate one or multiple peak wavelengths of light. In certain embodiments, one or more light emitting sources 52 may be arranged to produce one or both of ES increasing light and ES releasing light.

Figure 14:
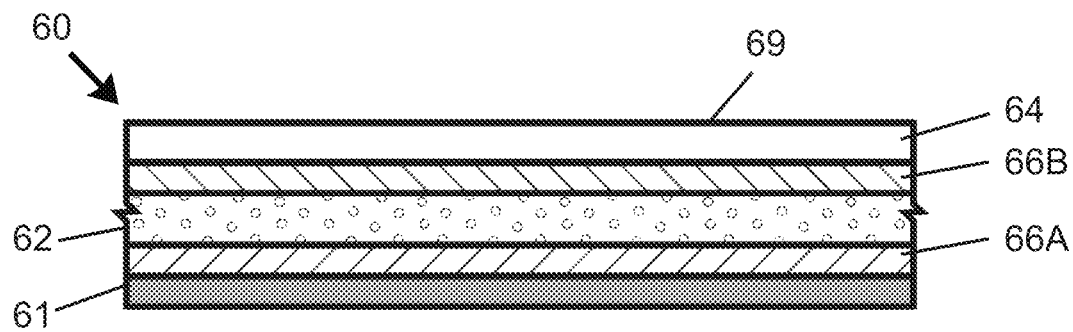
FIG. 14 is a side cross-sectional schematic view of a portion of a device for delivering light energy to living mammalian tissue, the device including a flexible substrate, one or more organic light emitting diode layers arranged between an anode and cathode, and an encapsulant layer arranged over the cathode.

FIG. 14 is a side cross-sectional schematic view of a portion of a device 60 for delivering light energy to living mammalian tissue, the device 60 including a flexible substrate 61, a passive-matrix organic light emitting diode (OLED) structure (embodied in an anode layer 66A, a cathode layer 66B, and an OLED stack 62 between the anode and cathode layers 66A, 66B. In certain embodiments, the OLED stack 62 may be configured to generate multiple wavelengths of light. The substrate 61 preferably includes a flexible PCB, which may include a reflective surface to reflect light toward a light-transmissive outer surface 69 of the device 60. An encapsulant layer 64 is arranged over the cathode layer 66B and preferably defines the light-transmissive outer surface 69 of the device 60. In certain embodiments, one or more light emitting wavelengths produced by the OLED stack 62 may include ES increasing light and/or ES releasing light.

Figure 15:
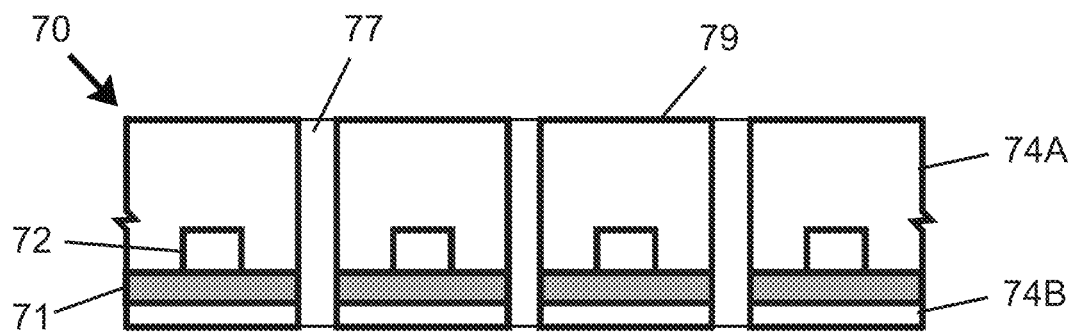
FIG. 15 is a side cross-sectional schematic view of a portion of a device for delivering light energy to living mammalian tissue, the device including a flexible substrate, multiple direct view light emitting sources supported by the substrate, encapsulant material layers arranged above and below the substrate and over the light emitting sources, and holes or perforations defined through both the substrate and the encapsulant material layers.

FIG. 15 is a side cross-sectional schematic view of a portion of a device 70 for delivering light energy to living mammalian tissue, the device 70 including a flexible substrate 71, multiple direct view light emitting sources 72 supported by the substrate 71, and encapsulant material layers 74A, 74B arranged above and below the substrate 71, respectively. The substrate 71 preferably includes a flexible PCB, which may include a reflective surface to reflect light toward a light-transmissive outer surface 79 of the device 70. The light emitting device 70 further includes holes or perforations 77 defined through both the substrate 71 and the encapsulant material layers 74A, 74B. In certain embodiments, one or more light emitting sources 72 may be arranged to produce one or both of ES increasing light and ES releasing light.

Figure 16:
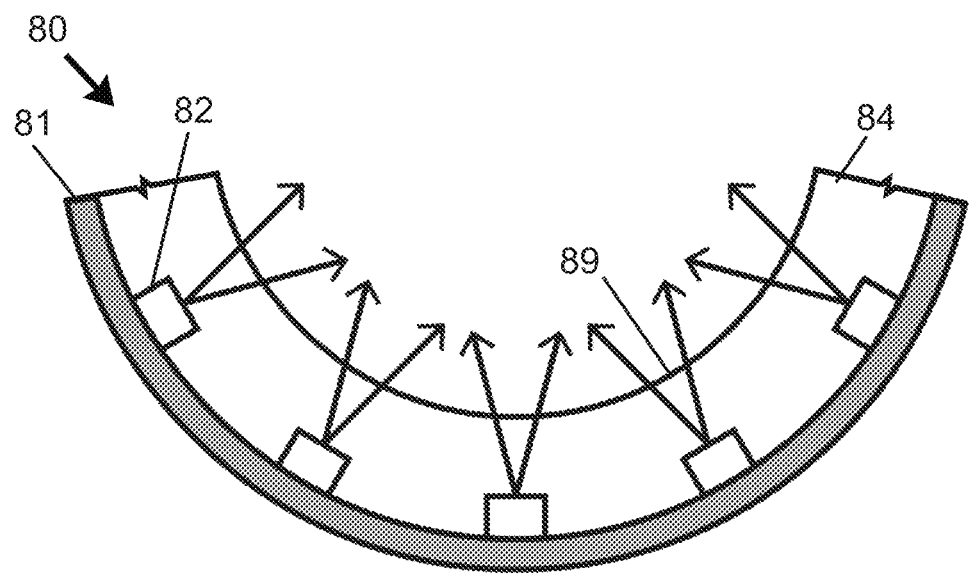
FIG. 16 is a side cross-sectional schematic view of a portion of a device for delivering light energy to living mammalian tissue, wherein the device includes multiple direct view light emitting sources supported by a substrate and covered by an encapsulant layer, and the device is arranged in a concave configuration.

FIG. 16 is a side cross-sectional schematic view of a portion of a device 80 for delivering light energy to living mammalian tissue, wherein the device 80 includes multiple direct view light emitting sources 82 supported by a flexible substrate 81 and covered by an encapsulant layer 84. The substrate 81 preferably includes a flexible PCB, which may include a reflective surface to reflect light toward a light-transmissive outer surface 89 of the device 80. The device 80 is preferably flexible to permit it to be bent or shaped into a variety of shapes to conform to a portion of a mammalian body. As illustrated, the device 80 is arranged in a concave configuration with the multiple light emitting sources 82 arranged to direct emissions toward a center of curvature of the device 80. In certain embodiments, one or more light emitting sources 82 may be arranged to produce one or both of ES increasing light and ES releasing light.

Figure 17:
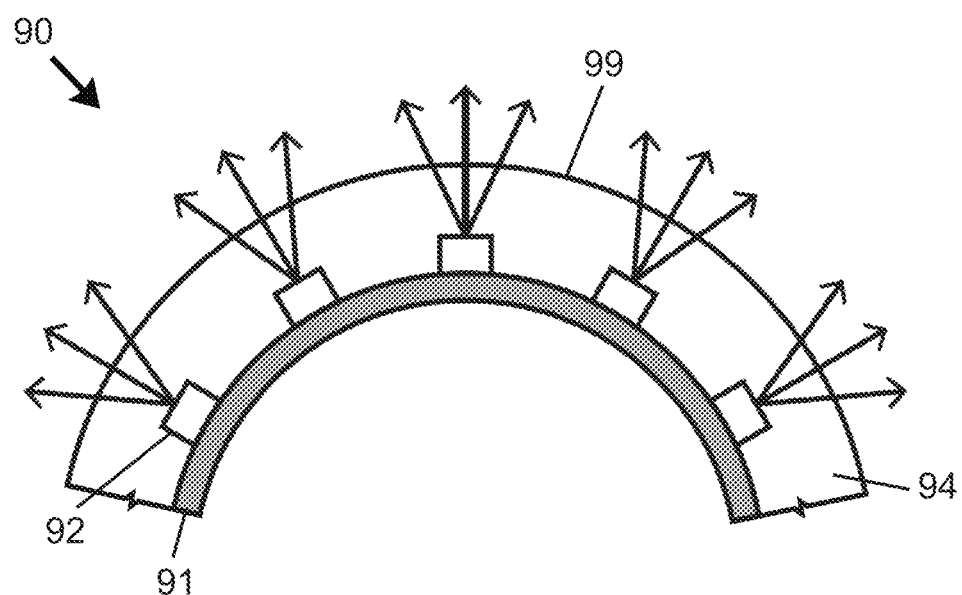
FIG. 17 is a side cross-sectional schematic view of a portion of a device for delivering light energy to living mammalian tissue, wherein the device includes multiple direct view light emitting sources supported by a substrate and covered by an encapsulant layer, and the device is arranged in a convex configuration.

FIG. 17 is a side cross-sectional schematic view of a portion of a device 90 for delivering light energy to living mammalian tissue, wherein the device 90 includes multiple direct view light emitting sources 92 supported by a flexible substrate 91 and covered by an encapsulant layer 94. The substrate 91 preferably includes a flexible PCB, which may include a reflective surface to reflect light toward a light-transmissive outer surface 99 of the device 90. The device 90 is preferably flexible to permit it to be bent or shaped into a variety of shapes to conform to a portion of a mammalian body. As illustrated, the device 90 is arranged in a convex configuration with the multiple light emitting elements 92 arranged to direct emissions away from a center of curvature of the device 90. In certain embodiments, one or more light emitting sources 92 may be arranged to produce one or both of ES increasing light and ES releasing light.

Figure 18:
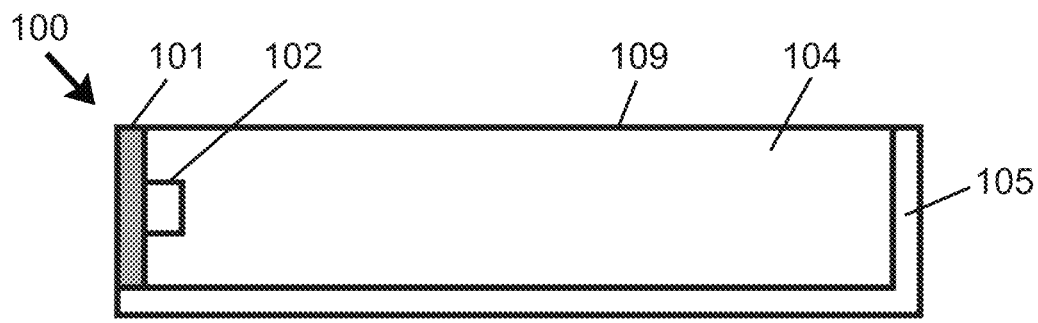
FIG. 18 is a side cross-sectional schematic view of a portion of a device for delivering light energy to living mammalian tissue, wherein the device is edge lit with one or more light emitting sources supported by a flexible printed circuit board (PCB), other non-light-transmitting surfaces of the device are bounded by a flexible reflective substrate, and the flexible PCB and light emitting source(s) are covered with an encapsulant material.

FIG. 18 is a side cross-sectional schematic view of a portion of a device 100 for delivering light energy to living mammalian tissue, wherein the device 100 is edge lit with one or more light emitting sources 102 supported by a flexible printed circuit board (PCB) 101 that preferably includes a reflective surface. Other non-light-transmissive surfaces of the device 100 are bounded by a flexible reflective substrate 105 arranged to reflect light toward a light-transmissive outer surface 109 of the device 100. The flexible PCB 101, the light emitting source(s) 102, and the flexible reflective substrate 105 are covered with an encapsulant material 104, which may include silicone. As illustrated, the device 100 may include a substantially constant thickness. In certain embodiments, one or more light emitting sources 102 may be arranged to produce one or both of ES increasing light and ES releasing light.

Figure 19:
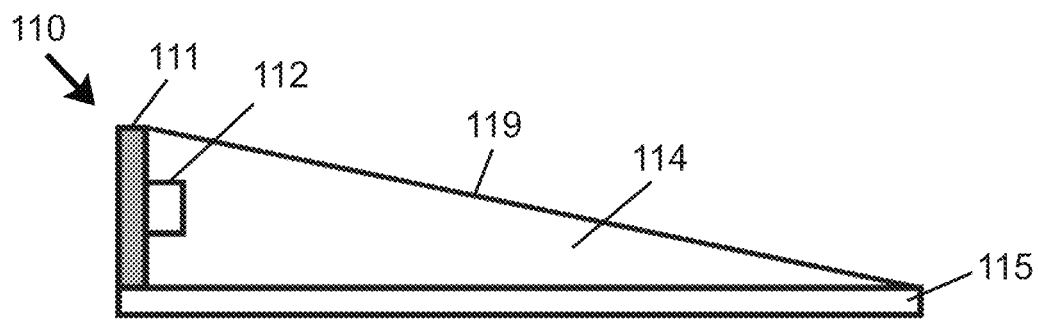
FIG. 19 is a side cross-sectional schematic view of a portion of a device for delivering light energy to living mammalian tissue, wherein the device is edge lit with one or more light emitting sources supported by a flexible printed circuit board (PCB), another non-light-transmitting surface of the device is bounded by a flexible reflective substrate, the flexible PCB and light emitting source(s) are covered with an encapsulant material, and the device is tapered in thickness.

FIG. 19 is a side cross-sectional schematic view of a portion of a device 110 for delivering light energy to living mammalian tissue, wherein the device 110 is edge lit with one or more light emitting sources 112 supported by a flexible PCB 111 that preferably includes a reflective surface. A non-light-transmitting face of the device 110 is bounded by a flexible reflective substrate 115 arranged to reflect light toward a light-transmissive outer surface 119 of the device 110. The flexible PCB 111, the light emitting source(s) 112, and the flexible reflective substrate 115 are covered with an encapsulant material 114, which may include silicone. As illustrated, the device 110 may include a thickness that is tapered with distance away from the light emitting sources 112. Such tapered thickness may enable the device 110 to more easily be wrapped against or to conform to areas of a mammalian (e.g., human) body. In certain embodiments, one or more light emitting sources 112 may be arranged to produce one or both of ES increasing light and ES releasing light.

Figure 20:
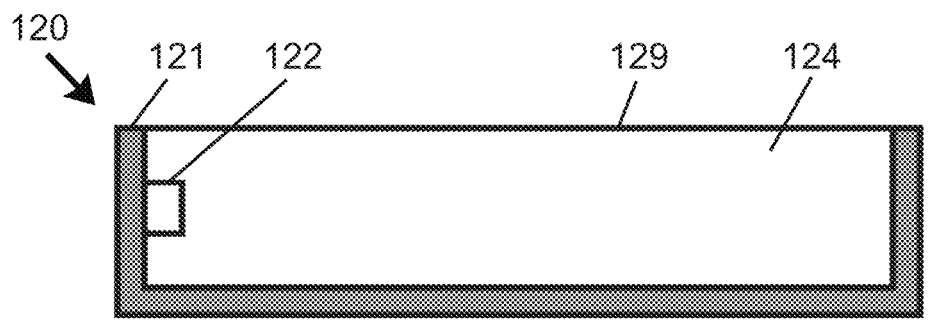
FIG. 20 is a side cross-sectional schematic view of a portion of a device for delivering light energy to living mammalian tissue, wherein the device is edge lit with one or more light emitting sources supported by a flexible PCB having a reflective surface, non-light-transmitting surfaces of the device are further bounded by the flexible PCB, and the flexible PCB and light emitting source(s) are covered with an encapsulant material.

FIG. 20 is a side cross-sectional schematic view of a portion of a device 120 for delivering light energy to living mammalian tissue, wherein the device 120 is edge lit with one or more light emitting sources 122 supported by a flexible PCB 121 that bounds multiple edges and a face of the device 120. The flexible PCB 121 preferably includes a reflective surface arranged to reflect light toward a light-transmissive outer surface 129 of the device 120. The flexible PCB 121 and the light emitting source(s) 122 are covered with an encapsulant material 124, which may include silicone. In certain embodiments, one or more light emitting sources 122 may be arranged to produce one or both of ES increasing light and ES releasing light.

Figure 21:
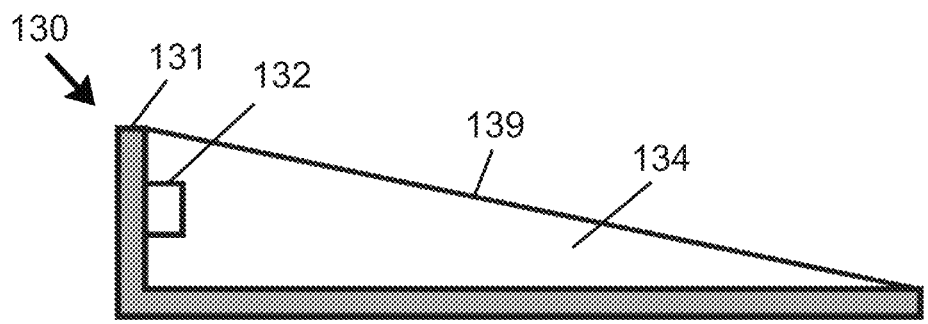
FIG. 21 is a side cross-sectional schematic view of a portion of a device for delivering light energy to living mammalian tissue, wherein the device is edge lit with one or more light emitting sources supported by a flexible PCB having a reflective surface, another non-light-transmitting surface of the device is further bounded by the flexible PCB, the flexible PCB and light emitting source(s) are covered with an encapsulant material, and the device is tapered in thickness.

FIG. 21 is a side cross-sectional schematic view of a portion of a device 130 for delivering light energy to living mammalian tissue, wherein the device 130 is edge lit with one or more light emitting sources 132 supported by a flexible PCB 131 that bounds one edge and one face of the device 130. The flexible PCB 131 preferably includes a reflective surface arranged to reflect light toward a light-transmissive outer surface 139 of the device 130. The flexible PCB 131 and the light emitting source(s) 132 are covered with an encapsulant material 134, which may include silicone. As illustrated, the device 130 may include a thickness that is tapered with distance away from the light emitting sources 132. In certain embodiments, one or more light emitting sources 132 may be arranged to produce one or both of ES increasing light and ES releasing light.

Figure 22:
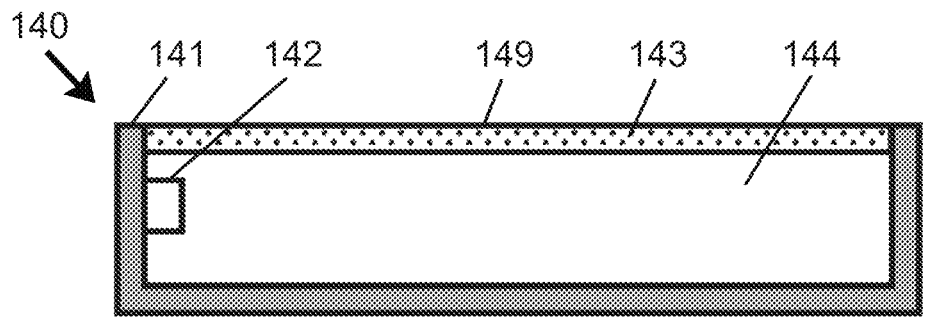
FIG. 22 is a side cross-sectional schematic view of a portion of a device for delivering light energy to living mammalian tissue, wherein the device is edge lit with one or more light emitting sources supported by a flexible PCB having a reflective surface, other non-light-transmitting surfaces of the device are further bounded by the flexible PCB, the flexible PCB and light emitting source(s) are covered with an encapsulant material, and a light-transmitting face of the device includes a diffusing and/or scattering layer.

FIG. 22 is a side cross-sectional schematic view of a portion of a device 140 for delivering light energy to living mammalian tissue, wherein the device 140 is edge lit with one or more light emitting sources 142 supported by a flexible PCB 141 that bounds multiple edges and a face of the device 140. In certain embodiments, one or more light emitting sources 142 may include a multi-emitter package arranged to generate one or multiple peak wavelengths of light. The flexible PCB 141 preferably includes a reflective surface arranged to reflect light toward a light-transmissive outer surface 149 of the device 140. The flexible PCB 141 and the light emitting source(s) 142 are covered with an encapsulant material 144, which may include silicone. Between the light-transmissive outer surface 149 and the encapsulant material 144, the device 140 further includes a diffusing and/or scattering layer 143. In certain embodiments, the diffusing and/or scattering layer 143 may include a sheet of material; in other embodiments, the diffusing and/or scattering layer 143 may include particles applied in or on the encapsulant material 144. In certain embodiments, one or more light emitting sources 142 may be arranged to produce one or both of ES increasing light and ES releasing light.

Figure 23:
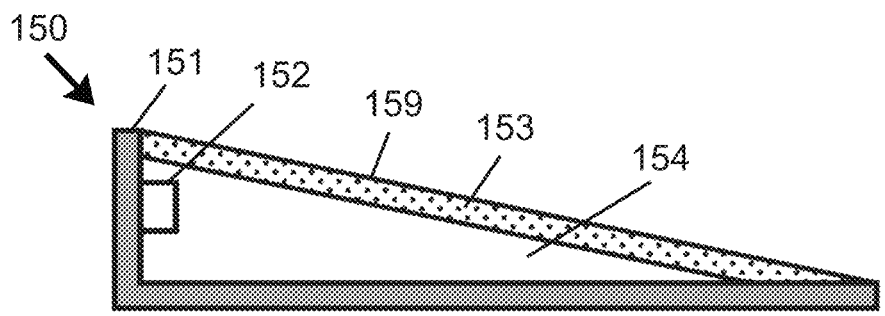
FIG. 23 is a side cross-sectional schematic view of a portion of a device for delivering light energy to living mammalian tissue, wherein the device is edge lit with one or more light emitting sources supported by a flexible PCB having a reflective surface, another non-light-transmitting surface of the device is further bounded by the flexible PCB, the flexible PCB and light emitting source(s) are covered with an encapsulant material, a light transmitting face of the device is tapered in thickness, and the light-transmitting face includes a diffusing and/or scattering layer.

FIG. 23 is a side cross-sectional schematic view of a portion of a device 150 for delivering light energy to living mammalian tissue, wherein the device 150 is edge lit with one or more light emitting sources 152 supported by a flexible PCB 151 that bounds one edge and one face of the device 150. In certain embodiments, one or more light emitting sources 152 may include a multi-emitter package arranged to generate one or multiple peak wavelengths of light. The flexible PCB 151 preferably includes a reflective surface arranged to reflect light toward a light-transmissive outer surface 159 of the device 150. The flexible PCB 151 and the light emitting source(s) 152 are covered with an encapsulant material 154, which may include silicone. Between the light-transmissive outer surface 159 and the encapsulant material 154, the device 150 further includes a diffusing and/or scattering layer 153. In certain embodiments, the diffusing and/or scattering layer 153 may include a sheet of material; in other embodiments, the diffusing and/or scattering layer 153 may include particles applied in or on the encapsulant material 154. As illustrated, the device 150 may include a thickness that is tapered with distance away from the light emitting sources 152. In certain embodiments, one or more light emitting sources 152 may be arranged to produce one or both of ES increasing light and ES releasing light.

Figure 24:
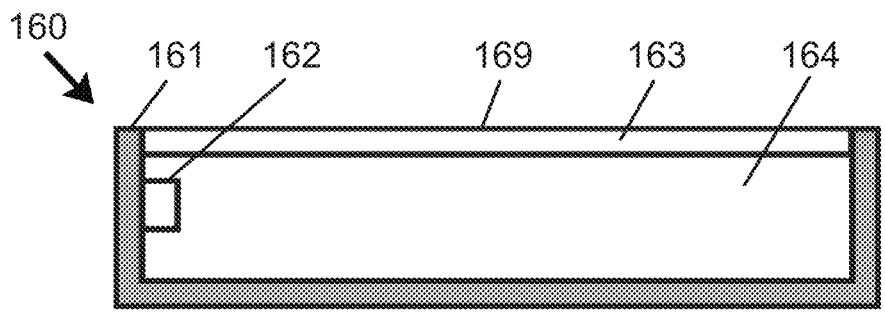
FIG. 24 is a side cross-sectional schematic view of a portion of a device for delivering light energy to living mammalian tissue, wherein the device is edge lit with one or more light emitting sources supported by a flexible PCB having a reflective surface, other non-light-transmitting surfaces of the device are further bounded by the flexible PCB, the flexible PCB and light emitting source(s) are covered with an encapsulant material, and a light-transmitting face of the device includes a wavelength conversion material layer.

FIG. 24 is a side cross-sectional schematic view of a portion of a device 160 for delivering light energy to living mammalian tissue, wherein the device 160 is edge lit with one or more light emitting sources 162 supported by a flexible PCB 161 that bounds multiple edges and a face of the device 160. In certain embodiments, one or more light emitting sources 162 may include a multi-emitter package arranged to generate one or multiple peak wavelengths of light. The flexible PCB 161 preferably includes a reflective surface arranged to reflect light toward a light-transmissive outer surface 169 of the device 160. The flexible PCB 161 and the light emitting source(s) 162 are covered with an encapsulant material 164, which may include silicone. Between the light-transmissive outer surface 169 and the encapsulant material 164, the device 160 further includes a wavelength conversion material 163. In certain embodiments, the wavelength conversion material 163 may include a sheet or layer of material; in other embodiments, the wavelength conversion material 163 may include particles applied in or on the encapsulant material 164. In certain embodiments, one or more light emitting sources 162 may be arranged to produce one or both of ES increasing light and ES releasing light.

Figure 25:
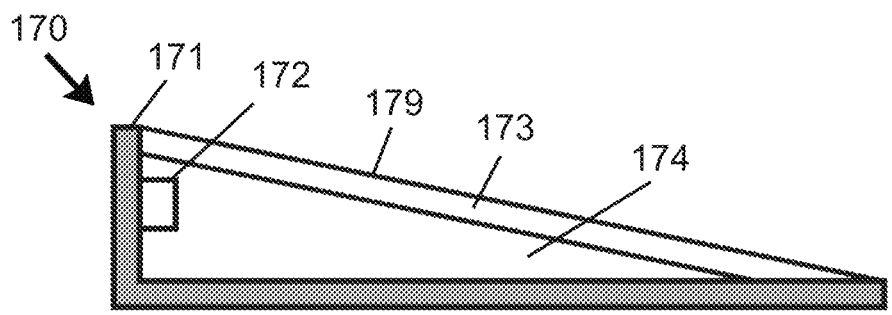
FIG. 25 is a side cross-sectional schematic view of a portion of a device for delivering light energy to living mammalian tissue, wherein the device is edge lit with one or more light emitting sources supported by a flexible PCB having a reflective surface, another non-light-transmitting surface of the device is further bounded by the flexible PCB, the flexible PCB and light emitting source(s) are covered with an encapsulant material, a light transmitting face of the device is tapered in thickness, and the light-transmitting face includes a wavelength conversion material layer.

FIG. 25 is a side cross-sectional schematic view of a portion of a device 170 for delivering light energy to living mammalian tissue, wherein the device 170 is edge lit with one or more light emitting sources 172 supported by a flexible PCB 171 that bounds one edge and one face of the device 170. In certain embodiments, one or more light emitting sources 172 may include a multi-emitter package arranged to generate one or multiple peak wavelengths of light. The flexible PCB 171 preferably includes a reflective surface arranged to reflect light toward a light-transmissive outer surface 179 of the device 170. The flexible PCB 171 and the light emitting source(s) 172 are covered with an encapsulant material 174, which may include silicone. Between the light-transmissive outer surface 179 and the encapsulant material 174, the device 170 further includes a wavelength conversion material 173. In certain embodiments, the wavelength conversion material 173 may include a sheet or layer of material; in other embodiments, the wavelength conversion material 173 may include particles applied in or on the encapsulant material 174. As illustrated, the device 170 may include a thickness that is tapered with distance away from the light emitting sources 172. In certain embodiments, one or more light emitting sources 172 may be arranged to produce one or both of ES increasing light and ES releasing light.

FIG. 26 is a side cross-sectional schematic view of a portion of a device 180 for delivering light energy to living mammalian tissue, wherein the device 180 is edge lit along multiple edges with multiple light emitting sources 182 supported by a flexible PCB 181 having a reflective surface arranged to reflect light toward a light-transmissive outer surface 189 of the device 180. The flexible PCB 181 and light emitting sources 182 are covered with an encapsulant material 184, and a wavelength conversion material 183 is distributed in the encapsulant material 184. In certain embodiments, one or more light emitting sources 182 may include a multi-emitter package arranged to generate one or multiple peak wavelengths of light. In certain embodiments, one or more light emitting sources 182 may be arranged to produce one or both of ES increasing light and ES releasing light.

FIG. 27 is a side cross-sectional schematic view of a portion of a device 190 for delivering light energy to living mammalian tissue, wherein the device 190 is edge lit along multiple edges with multiple light emitting sources 192 supported by a flexible PCB 191 having a reflective surface arranged to reflect light toward a light-transmissive outer surface 199 of the device 190. The device 190 further includes raised light extraction features 197 supported by the flexible PCB 191, with such features 197 serving to reflect laterally-transmitted light toward the outer surface 199. An encapsulant material 194 is provided over the flexible PCB 191, the light emitting sources 192, and the light extraction features 197. In certain embodiments, one or more light emitting sources 192 may include a multi-emitter package arranged to generate one or multiple peak wavelengths of light. In certain embodiments, one or more light emitting sources 192 may be arranged to produce one or both of ES increasing light and ES releasing light.

In certain embodiments, the light extraction features 197 may be dispensed, molded, layered, or painted on the flexible PCB 191. In certain embodiments, different light extraction features 197 may include different indices of refraction. In certain embodiments, different light extraction features 197 may include different sizes and/or shapes. In certain embodiments, light extraction features 197 may be uniformly or non-uniformly distributed over the flexible PCB 191. In certain embodiments, light extraction features 197 may include tapered surfaces. In certain embodiments, different light extraction features 197 may include one or more connected portions or surfaces. In certain embodiments, different light extraction features 197 may be discrete or spatially separated relative to one another. In certain embodiments, light extraction features 197 may be arranged in lines, rows, zig-zag shapes, or other patterns. In certain embodiments, one or more wavelength conversion materials may be arranged on or proximate to one or more light extraction features 197.

FIG. 28 is a side cross-sectional schematic view of a portion of a device 200 for delivering light energy to living mammalian tissue, wherein the device 200 is edge lit along multiple edges with multiple light emitting sources 202 supported by a flexible PCB 201 having a reflective surface arranged to reflect light toward a light-transmissive outer surface 209 of the device 200. In certain embodiments, one or more light emitting sources 202 may be arranged to produce one or both of ES increasing light and ES releasing light. Encapsulant material layers 204A, 204B are arranged above and below the flexible PCB 201 and over the light emitting sources 202. Holes or perforations 205 are defined through the flexible PCB 201 and the encapsulant material layers 204A, 204B. The holes or perforations 205 preferably allow passage of at least one of air and exudate through the device 200.

Holes or perforations defined through a device (e.g., through a PCB and encapsulant layers) as described herein may include holes of various shapes and configurations. Holes may be round, oval, rectangular, square, polygonal, or any other suitable axial shape. Cross-sectional shapes of holes or perforations may be constant or non-constant. Cross-sectional shapes that may be employed according to certain embodiments are shown in FIGS. 29A-29C. FIG. 29A is a cross-sectional view of a first exemplary hole 215A definable through an encapsulant layer 214A of a device for delivering light energy to living mammalian tissue, the hole 215A having a diameter that is substantially constant with depth and extending to an outer light transmissive surface 219A. FIG. 29B is a cross-sectional view of a second exemplary hole 215B definable through an encapsulant layer 214B of a device for delivering light energy to living mammalian tissue, the hole 215B having a diameter that increases with increasing depth and extending to an outer light transmissive surface 219B. FIG. 29C is a cross-sectional view of a third exemplary hole 215C definable through an encapsulant layer 214C of a device for delivering light energy to living mammalian tissue, the hole 215C having a diameter that decreases with increasing depth and extending to an outer light transmissive surface 219C.

In certain embodiments, perforations or holes may encompass at least 2%, at least 5%, at least 7%, at least 10%, at least 15%, at least 20%, or at least 25% of a facial area of a device for delivering light energy to living mammalian tissue as disclosed herein. In certain embodiments, one or more of the preceding ranges may be bounded by an upper limit of no greater than 10%, no greater than 15%, no greater than 20%, or no greater than 30%. In certain embodiments, perforations or holes may be provided with substantially uniform size and distribution, with substantially uniform distribution but non-uniform size, with non-uniform size and non-uniform distribution, or any other desired combination of size and distribution patterns.

Figure 30:
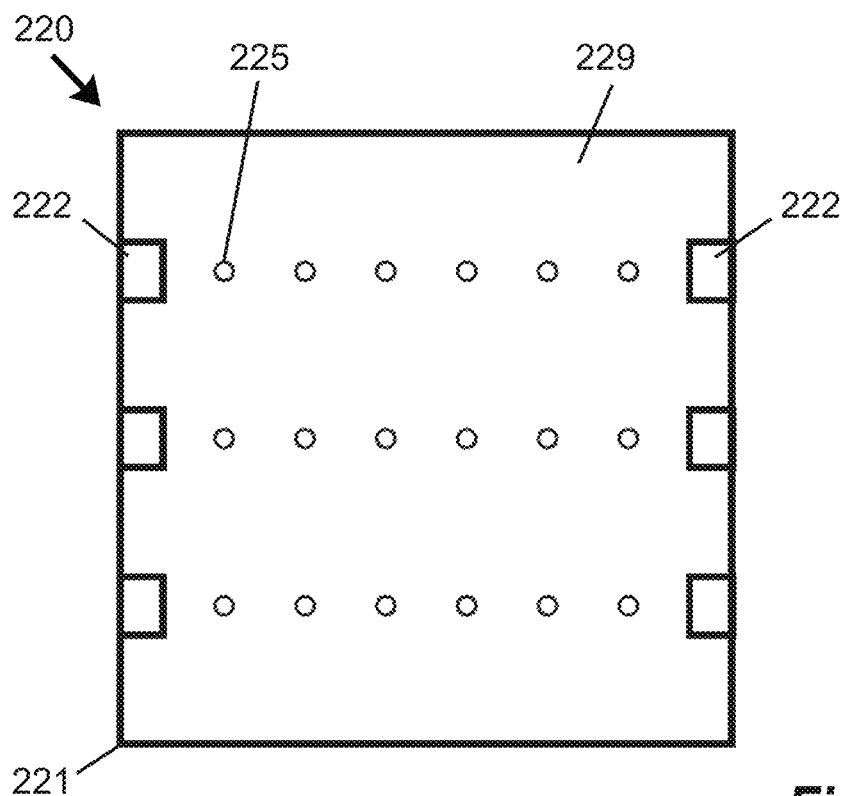
FIG. 30 is a top schematic view of at least a portion of a device for delivering light energy to living mammalian tissue, wherein the device is edge lit along multiple edges with multiple light emitting sources supported by a flexible PCB, and multiple holes or perforations of substantially uniform size and substantially uniform distribution are defined through the flexible PCB.

FIG. 30 is a top schematic view of at least a portion of a device 220 for delivering light energy to living mammalian tissue, wherein the device 220 is edge lit along multiple edges with multiple light emitting sources 222 supported by a flexible PCB 221. The flexible PCB 221 is preferably encapsulated on one or both sides with an encapsulant material. Multiple holes or perforations 225 of substantially uniform size and substantially uniform distribution are defined through the flexible PCB 221 and any associated encapsulant material layers. The flexible PCB 221 preferably includes a reflective material arranged to reflect light toward a light transmissive outer surface 229 of the device 220. In certain embodiments, one or more light emitting sources 222 may be arranged to produce one or both of ES increasing light and ES releasing light.

Figure 31:
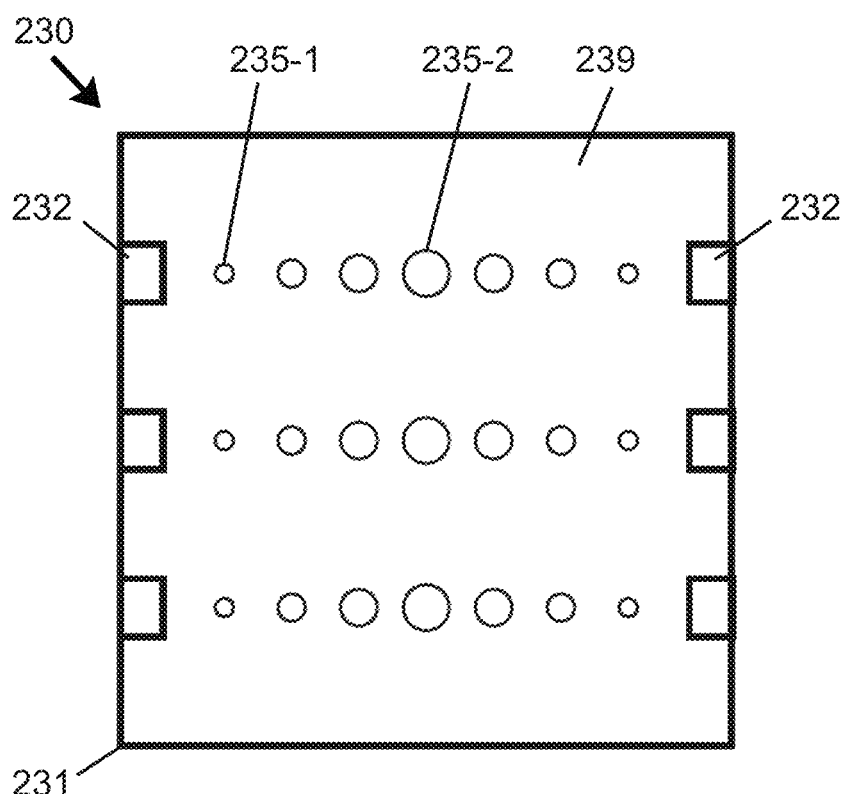
FIG. 31 is a top schematic view of at least a portion of a device for delivering light energy to living mammalian tissue, wherein the device is edge lit along multiple edges with multiple light emitting sources supported by a flexible PCB, and multiple holes or perforations of different sizes but with a substantially uniform distribution are defined through the flexible PCB.

FIG. 31 is a top schematic view of at least a portion of a device 230 for delivering light energy to living mammalian tissue, wherein the device 230 is edge lit along multiple edges with multiple light emitting sources 232 supported by a flexible PCB 231. The flexible PCB 231 is preferably encapsulated on one or both sides with an encapsulant material. Multiple holes or perforations 235-1, 235-2 of differing sizes, but substantially uniform distribution, are defined through the flexible PCB 231 and any associated encapsulant material layers. The flexible PCB 231 preferably includes a reflective material arranged to reflect light toward a light transmissive outer surface 239 of the device 230. In certain embodiments, one or more light emitting sources 232 may be arranged to produce one or both of ES increasing light and ES releasing light.

Figure 32:
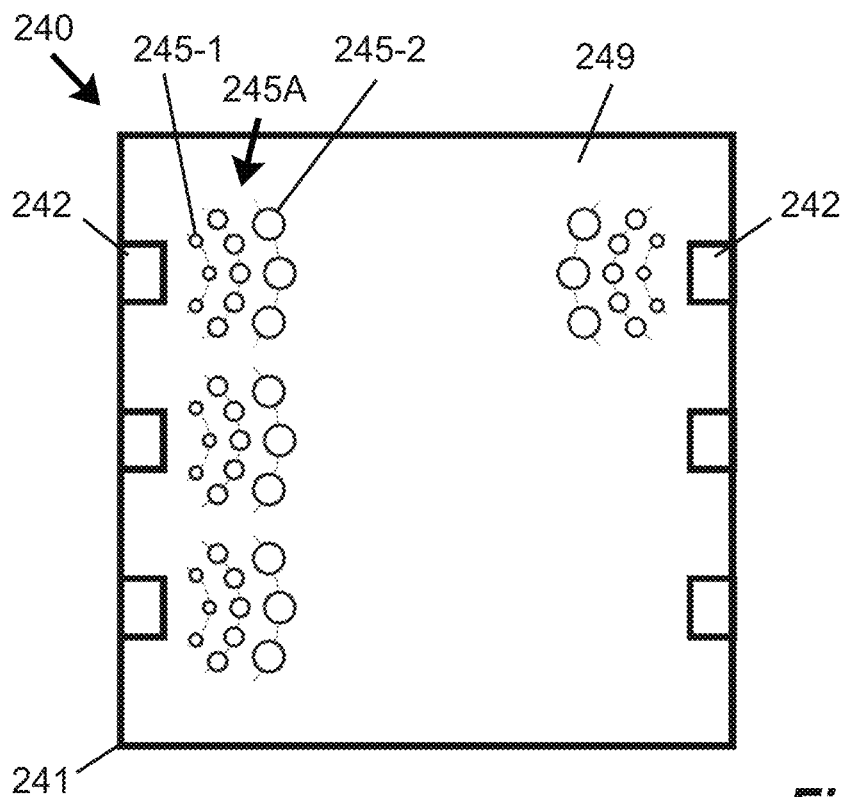
FIG. 32 is a top schematic view of at least a portion of a device for delivering light energy to living mammalian tissue, wherein the device is edge lit along multiple edges with multiple light emitting sources supported by a flexible PCB, and multiple holes or perforations of different sizes are provided in clusters and defined through the flexible PCB proximate to selected light emitting sources.

FIG. 32 is a top schematic view of at least a portion of a device 240 for delivering light energy to living mammalian tissue, wherein the device 240 is edge lit along multiple edges with multiple light emitting sources 242 supported by a flexible PCB 241. The flexible PCB 241 is preferably encapsulated on one or both sides with an encapsulant material. The flexible PCB 241 preferably includes a reflective material arranged to reflect light toward a light transmissive outer surface 249 of the device 240. Multiple holes or perforations 245-1, 245-2 of different sizes are provided in one or more clusters 245A (e.g., proximate to one or more light emitting sources 242) and defined through the flexible PCB 241 and any associated encapsulant material layers. In certain embodiments, one or more light emitting sources 242 may be arranged to produce one or both of ES increasing light and ES releasing light.

Figure 33:
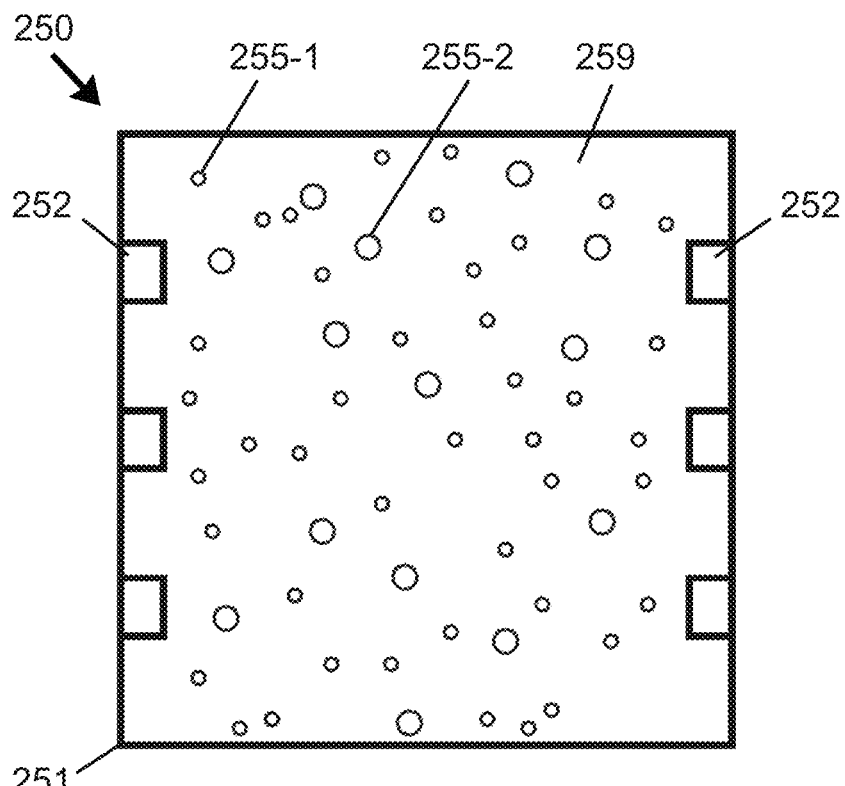
FIG. 33 is a top schematic view of at least a portion of a device for delivering light energy to living mammalian tissue, wherein the device is edge lit along multiple edges with multiple light emitting sources supported by a flexible PCB, and multiple holes or perforations of different sizes and with a non-uniform (e.g., random) distribution are defined through the flexible PCB.

FIG. 33 is a top schematic view of at least a portion of a device 250 for delivering light energy to living mammalian tissue, wherein the device 250 is edge lit along multiple edges with multiple light emitting sources 252 supported by a flexible PCB 251. The flexible PCB 251 is preferably encapsulated on one or both sides with an encapsulant material. The flexible PCB 251 preferably includes a reflective material arranged to reflect light toward a light transmissive outer surface 259 of the device 250. Multiple holes or perforations 255-1, 255-2 of different sizes and with a non-uniform (e.g., random) distribution are defined through the flexible PCB 251 and any associated encapsulant material layers. In certain embodiments, one or more light emitting sources 252 may be arranged to produce one or both of ES increasing light and ES releasing light.

Figure 34A:
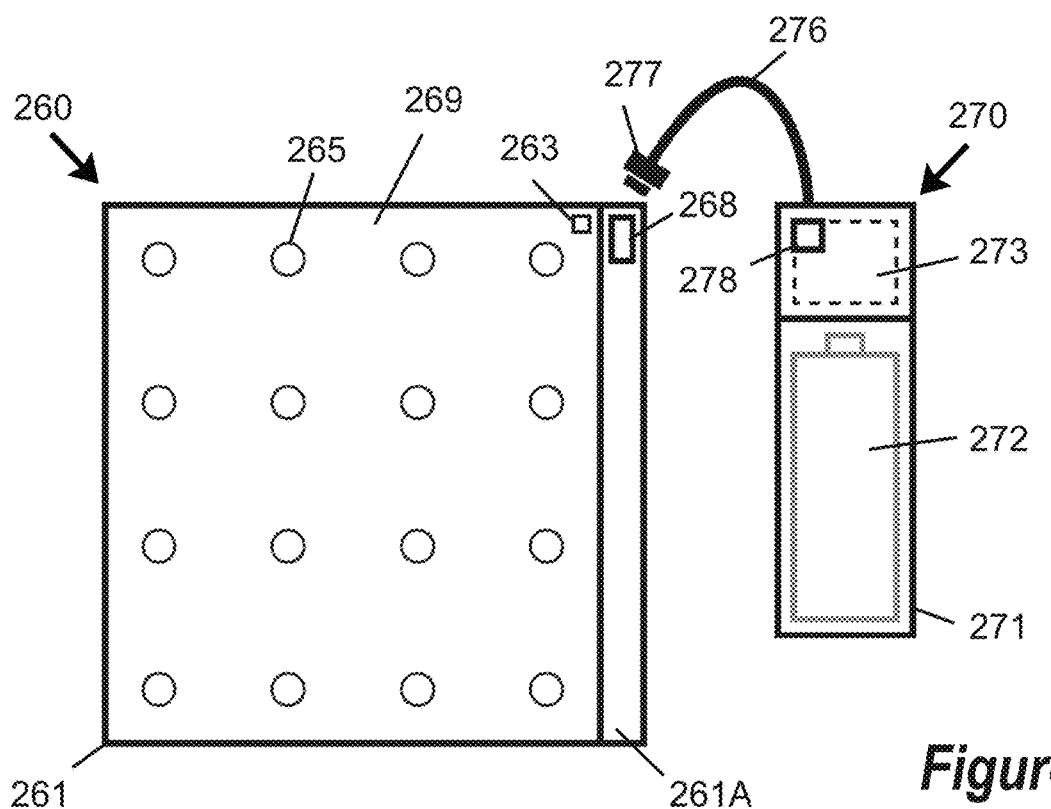
FIG. 34A is a top schematic view of at least a portion of a light emitting device for delivering light energy to living mammalian tissue and at least a portion of a battery/control module, wherein an elongated electrical cord is associated with the battery/control module for connecting the battery/control module to the light emitting device.

FIG. 34A is a top schematic view of at least a portion of a light emitting device 260 for delivering light energy to living mammalian tissue and at least a portion of a battery/control module 270, wherein an elongated electrical cable 276 is associated with the battery/control module 270 for connecting the battery/control module 270 to the light emitting device 260. The light emitting device 260 is edge lit along one edge with a light emitting region 261A supported by a flexible PCB 261. The flexible PCB 261 is preferably encapsulated on one or both sides with an encapsulant material. The flexible PCB 261 preferably includes a reflective material arranged to reflect light toward a light transmissive outer surface 269 of the device 260. Multiple holes or perforations 265 are defined through the flexible PCB 261 and any associated encapsulant material layers. One or more sensors 263 (e.g., temperature sensors or any other types of sensors disclosed herein) are arranged in or on the flexible PCB 261. A socket 268 associated with the light emitting device 260 is arranged to receive a plug 277 to which the electrical cable 276 from the battery/control module 270 is attached. The battery/control module 270 includes a body 271, a battery 272, and a control board 273, which may include an emitter driver circuit and/or any suitable control, sensing, interface, data storage, and/or communication components as disclosed herein. The battery/control module 270 may further include a port or other interface 278 to enable communication with an external device (e.g., laptop or tablet computer, a mobile phone, or another portable digital device) via wired or wireless means.

Figure 34B:
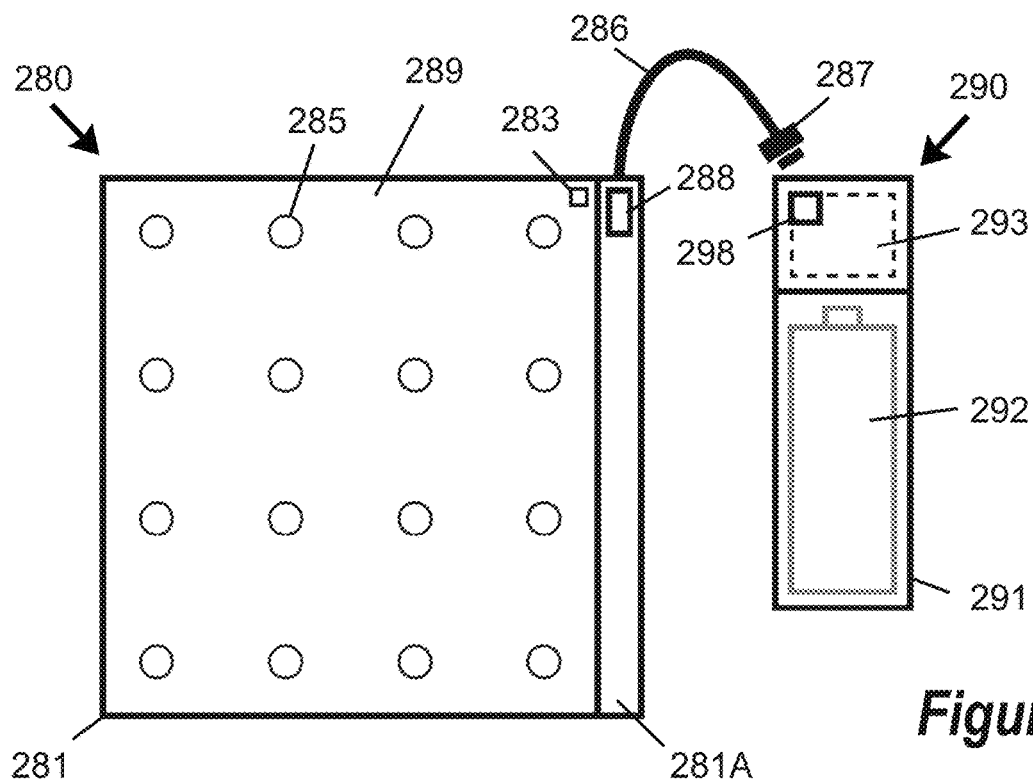
FIG. 34B is a top schematic view of at least a portion of a light emitting device for delivering light energy to living mammalian tissue and at least a portion of a battery/control module, wherein an elongated electrical cord is associated with the light emitting device for connecting the light emitting device to the battery/control module.

FIG. 34B is a top schematic view of at least a portion of a light emitting device 280 for delivering light energy to living mammalian tissue and at least a portion of a battery/control module 290, wherein an elongated electrical cable 286 is associated with the light emitting device 280 for connecting the light emitting device 280 to the battery/control module 290. The light emitting device 280 is edge lit along one edge with a light emitting region 281A supported by a flexible PCB 281. The flexible PCB 281 is preferably encapsulated on one or both sides with an encapsulant material. The flexible PCB 281 preferably includes a reflective material arranged to reflect light toward a light transmissive outer surface 289 of the device 280. Multiple holes or perforations 285 are defined through the flexible PCB 281 and any associated encapsulant material layers. One or more sensors 283 (e.g., temperature sensors or any other types of sensors disclosed herein) are arranged in or on the flexible PCB 281. A socket 298 associated with the battery/control module 290 is arranged to receive a plug 287 to which the electrical cable 286 from the light emitting device 280 is attached. The battery/control module 290 includes a body 291, a battery 292, and a control board 293, which may include an emitter driver circuit and/or any suitable control, sensing, interface, data storage, and/or communication components as disclosed herein. The light emitting device 280 may further include a port or other interface 288 to enable communication with an external device (e.g., laptop or tablet computer, a mobile phone, or another portable digital device) via wired or wireless means.

Figure 35:
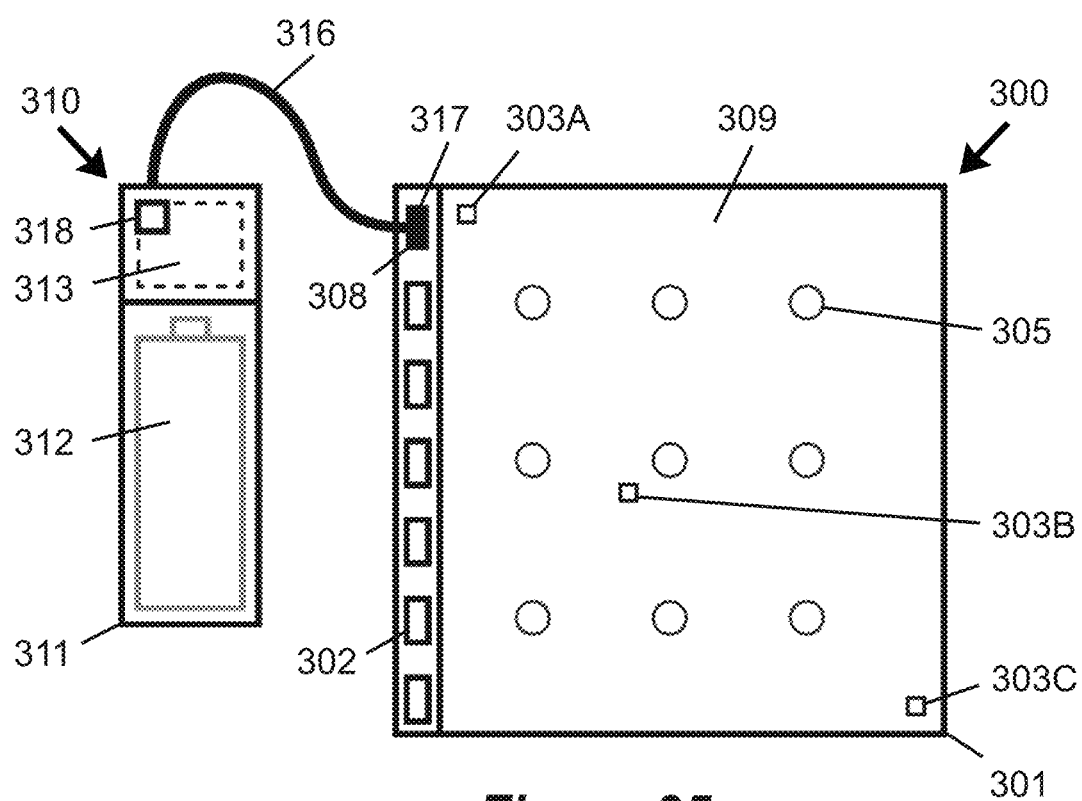
FIG. 35 is a top schematic view of at least a portion of a light emitting device for delivering light energy to living mammalian tissue and being connected via an electrical cord to a battery/control module, wherein the light emitting device includes multiple light emitters, multiple holes or perforations, and multiple sensors.

FIG. 35 is a top schematic view of at least a portion of a light emitting device 300 for delivering light energy to living mammalian tissue and being connected via an electrical cord 316 to a battery/control module 310, wherein the light emitting device 300 includes multiple light emitters 302 supported by a flexible PCB 301, multiple holes or perforations 305, and multiple sensors 303A-303C. The flexible PCB 301 is preferably encapsulated on one or both sides with an encapsulant material. The flexible PCB 301 preferably includes a reflective material arranged to reflect light toward a light transmissive outer surface 309 of the device 300. Multiple holes or perforations 305 are defined through the flexible PCB 301 and any associated encapsulant material layers. Multiple sensors 303A-303C are arranged in or on the flexible PCB 301. In certain embodiments, the sensors 303A-303C may differ in type from one another. In certain embodiments, the sensors 303A-303C may include one or more light emitters and photodiodes to illuminate a wound site with one or more selected wavelengths (e.g., green light) to detect blood flow in or proximate to a wound site to provide photoplethsmyography data. The sensors 303A-303C may alternatively or additionally be arranged to detect blood pressure, bandage or dressing covering pressure, heart rate, temperature, presence or concentration of chemical or biological species (e.g., in wound exudate), or other conditions. A socket 308 associated with the light emitting device 300 is arranged to receive a plug 317 to which the electrical cord 316 from the battery/control module 310 is attached. The battery/control module 310 includes a body 311, a battery 312, and a control board 313, which may include an emitter driver circuit and/or any suitable control, sensing, interface, data storage, and/or communication components as disclosed herein. The battery/control module 310 may further include a port or other interface 318 to enable communication with an external device (e.g., laptop or tablet computer, a mobile phone, or another portable digital device) via wired or wireless means.

Figure 36A:
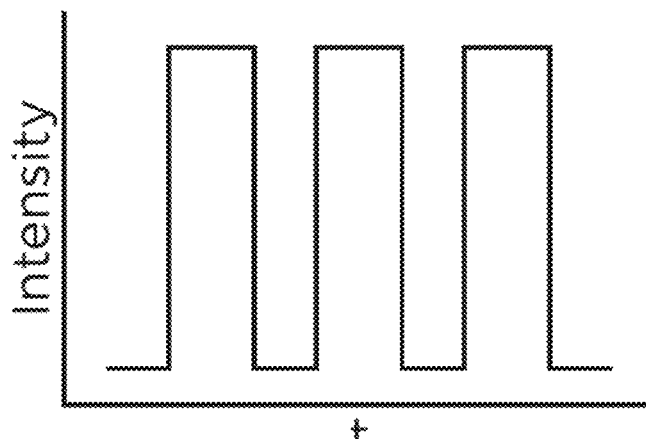
FIG. 36A is a plot of intensity versus time (t) embodying a first exemplary illumination cycle that may be used with at least one emitter of a light emitting device for delivering light energy to living mammalian tissue as disclosed herein.
Figure 36B:
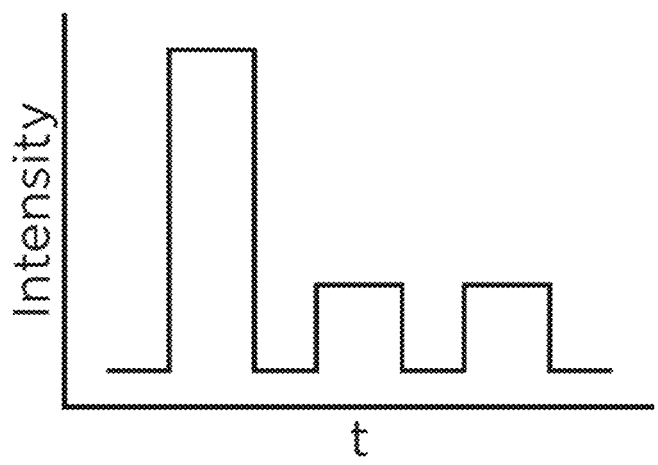
FIG. 36B is a plot of intensity versus time (t) embodying a second exemplary illumination cycle that may be used with at least one emitter of a light emitting device for delivering light energy to living mammalian tissue as disclosed herein.
Figure 36C:
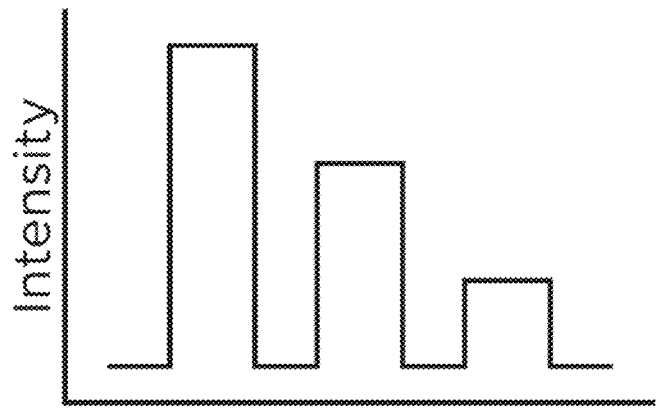
FIG. 36C is a plot of intensity versus time (t) embodying a third exemplary illumination cycle that may be used with at least one emitter of a light emitting device for delivering light energy to living mammalian tissue as disclosed herein.

FIGS. 36A-36C illustrate different pulse profiles that may be used with devices and methods according to the present disclosure. FIG. 36A is a plot of intensity versus time embodying a first exemplary illumination cycle that may be used with at least one emitter of a light emitting device for delivering light energy to living mammalian tissue as disclosed herein. As shown in FIG. 36A, a series of discrete pulses of substantially equal intensity may be provided during at least one time window or a portion thereof. FIG. 36B is a plot of intensity versus time embodying a second exemplary illumination cycle that may be used with at least one emitter of a light emitting device disclosed herein. As shown in FIG. 36B, intensity may be reduced from a maximum (or high) value to a reduced but non-zero value during at least one time window. FIG. 36C is a plot of intensity versus time embodying a third exemplary illumination cycle that may be used with at least one emitter of a light emitting device disclosed herein. As shown in FIG. 36C, intensity may be steadily reduced from a maximum (or high) value to sequentially reduced values over time. Other pulse profiles may be used according to certain embodiments.

Figure 37:
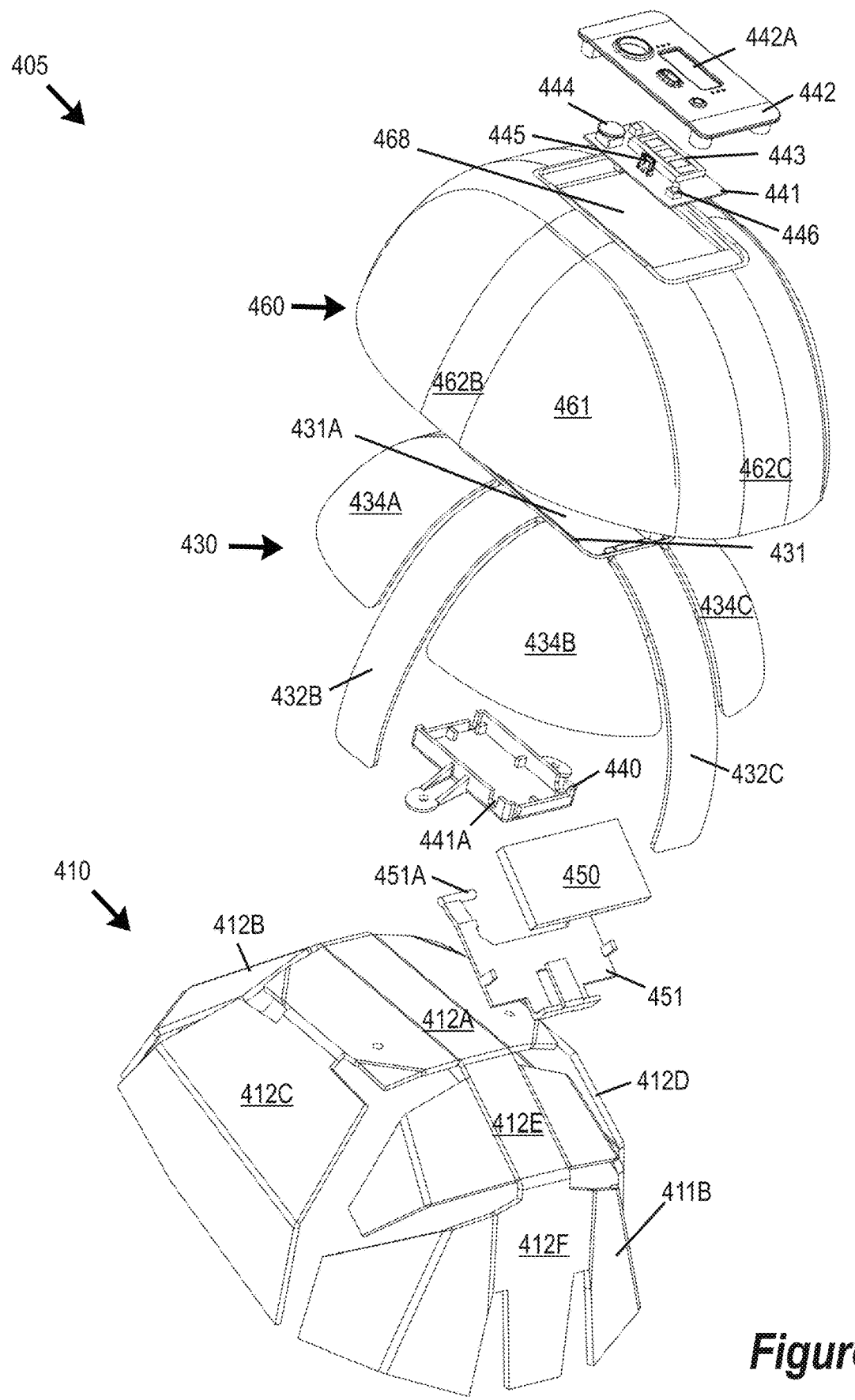
FIG. 37 is an exploded view of a light emitting device embodied in a wearable cap for delivering light energy to a scalp of a patient, the device including at least one light emitter supported by a flexible PCB arranged in a concave configuration, a concave support member shaped to receive the flexible PCB and support a battery and control module, and a fabric covering arranged to cover the support member and flexible substrate.

FIG. 37 is an exploded view of a light emitting device 405 embodied in a wearable cap for delivering light energy to a scalp of a patient. The device 405 includes multiple light emitters and standoffs supported by a flexible PCB 410 including multiple interconnected panels 412A-412F arranged in a concave configuration. A concave shaping member 430 (including a central frame 431, ribs 432A-432D, and curved panels 434A-434D) is configured to receive the flexible PCB 410. The ribs 432A-432D and curved panels 434A-434D project generally outwardly and downwardly from the central frame 431. Gaps are provided between portions of adjacent ribs 432A-432D and curved panels 434A-434D to accommodate outward expansion and inward contraction, and to enable transfer of heat and/or fluid (e.g., evaporation of sweat). A fabric covering member 460 is configured to cover the concave shaping member 430 and the flexible PCB 410 contained therein. A battery 450 and a battery holder 451 are arranged between the flexible PCB 410 and the concave shaping member 430. An electronics housing 440 is arranged to be received within an opening 431A defined in the central frame 431 of the concave shaping member 430. Pivotal coupling elements 441A, 451A are arranged to pivotally couple the battery holder 451 to the electronics housing 440. An electronics board 441 is insertable into the electronics housing 440, which is enclosed with a cover 442. Arranged on the electronics board 441 are a cycle counter 443, a control button 444, a charging/data port 445, and a status lamp 446. The various elements associated with the electronics housing 440 and the electronics board 441 may be referred to generally as a "control module." Windows 442A defined in the cover 442 provide access to the cycle counter 443, the control button 444, the charging/data port 445, and the status lamp 446. The fabric covering element 460 includes a fabric body 461 and multiple internal pockets 462A-462D arranged to receive portions of the ribs 432A-432D. An opening 468 at the top of the fabric covering element 460 is arranged to receive the cover 442.

Figure 38:
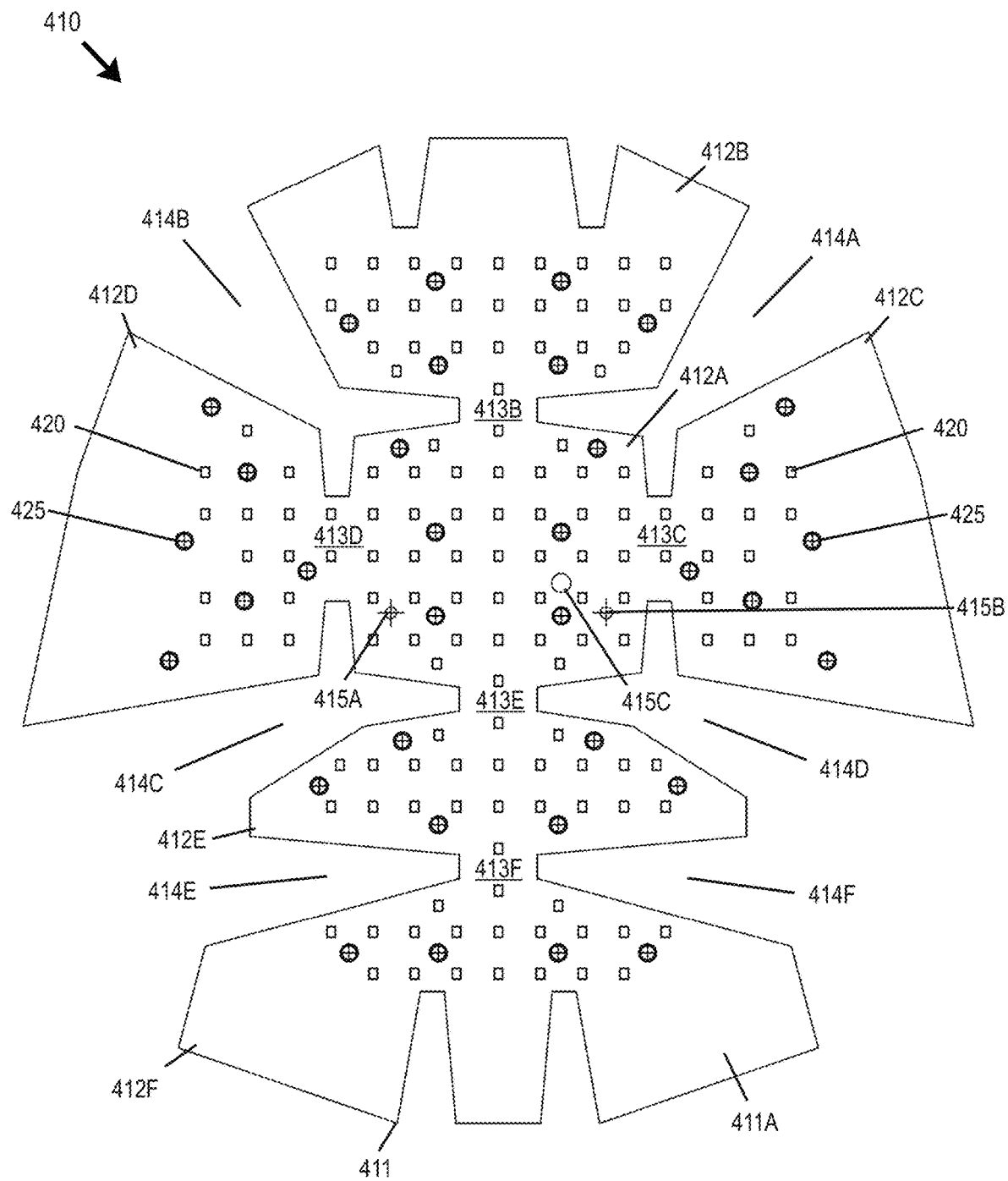
FIG. 38 is a bottom plan view of the flexible PCB of FIG. 37 prior to being shaped into a concave configuration.

FIG. 38 is a bottom plan view of the flexible PCB 410 including light emitters 420 and standoffs 425 arranged thereon. The PCB 410 includes a polyimide substrate 411, an inner surface 411A, and an outer surface 411B (shown in FIG. 37). In one embodiment, the light emitters 420 include a total of 280 light emitting diodes arranged as 56 strings of 5 LEDs, with a string voltage of 11V, a current limit of 5 mA, and a power consumption of 3.08 watts. FIG. 38 illustrates 36 standoffs 425 extending from the inner surface 411A of the flexible PCB 410. The flexible PCB 410 includes six interconnected panels 412A-412F, with the panels 412A-412F being connected to one another via narrowed tab regions 413B-413F. Gaps 414A-414F are provided between the various panels 412A-412F, with such gaps 414A-414F (which are extended proximate to the narrowed tab regions 413B-413F) being useful to permit transport of heat and/or fluid (e.g., evaporation of sweat) between the panels 412A-412F. As shown in FIG. 38, holes 415A, 415B are defined through the substrate 411 to receive fasteners (not shown) for joining the flexible PCB 410 to corresponding holes (not shown) defined in the electronics housing 440. A further opening 415C may be provided for sensor communication between a proximity sensor (e.g., photosensor) and the interior of the flexible PCB 410 when the flexible PCB 410 is shaped into a concave configuration.

Figure 39:
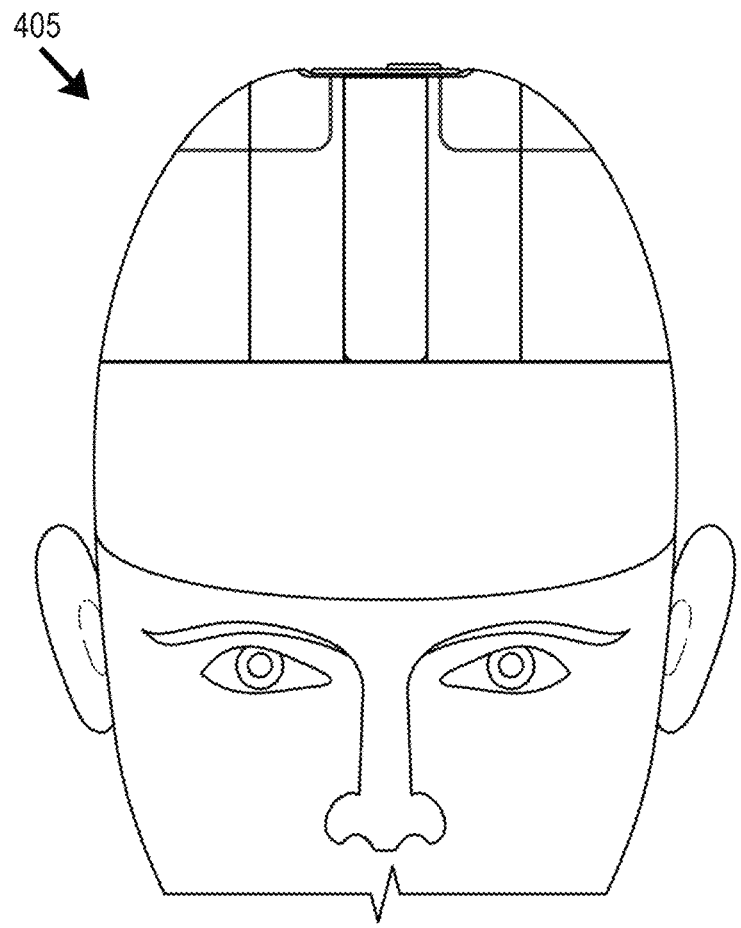
FIG. 39 is a front elevation view of the light emitting device of FIG. 37 affixed to a modeled human head.

FIG. 39 is a front elevation view of the assembled light emitting device 405 embodied in the wearable cap of FIG. 37 superimposed over a modeled human head. As shown in FIG. 39, the device 405 is embodied in a cap with a lower edge between a user's forehead and hairline, and above a user's ears.

Figure 40:
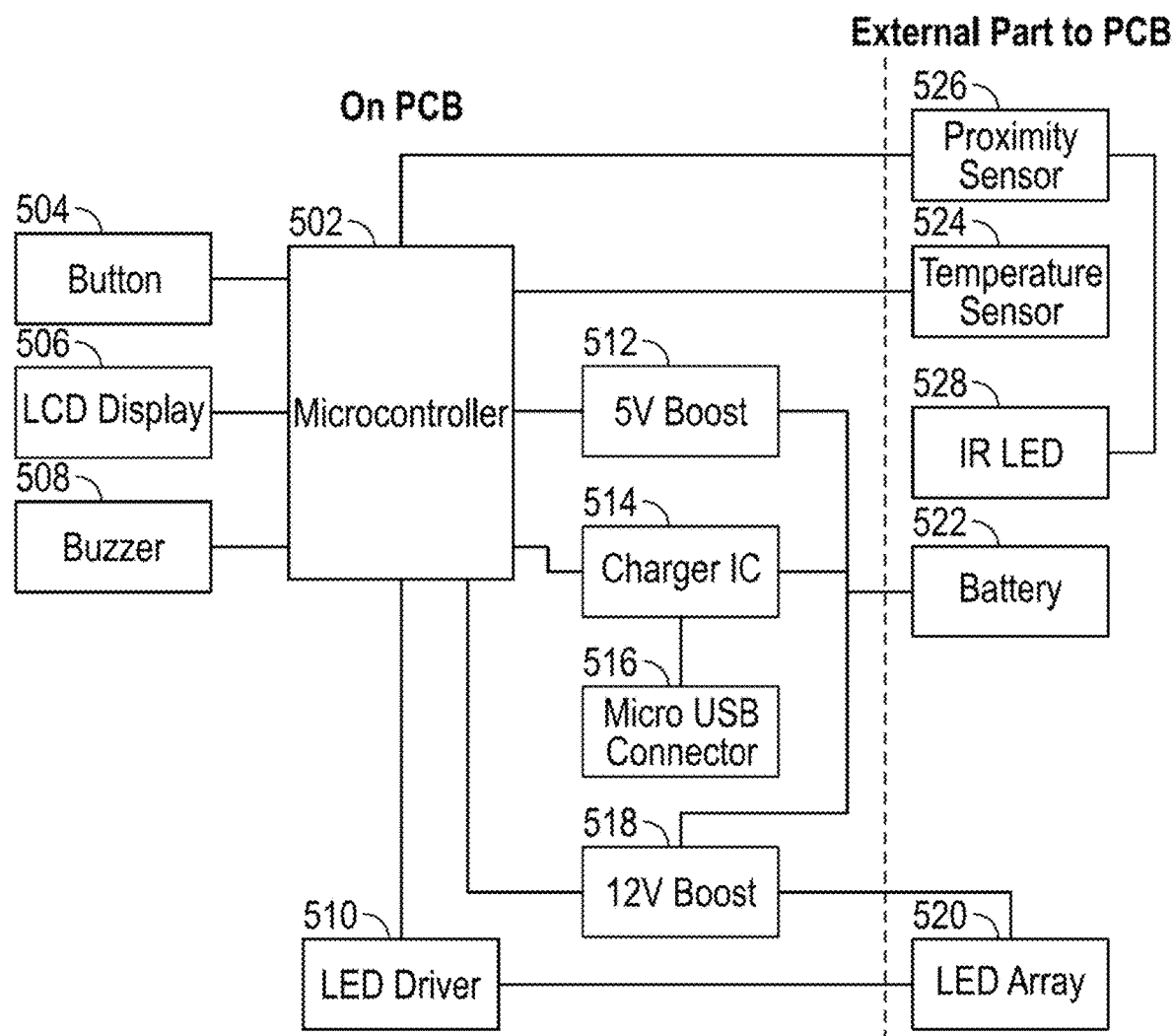
FIG. 40 is a schematic diagram showing interconnections between components of a light emitting device or delivering light energy to tissue of a patient according to one embodiment.

FIG. 40 is a schematic diagram showing interconnections between components of a light emitting device for delivering light energy to tissue of a patient according to one embodiment. A microcontroller 502 is arranged to receive power from a battery 522 (nominally 3.7V) via a 5V voltage boost circuit 512. The microcontroller may be arranged to control a charging integrated circuit 514 arranged between a microUSB connector 516 and the battery 522, wherein the microUSB connector 516 may be used to receive current for charging the battery 522. In certain embodiments, the microUSB connector 516 may also be used for communicating data and/or instructions to or from the microcontroller 502 and/or an associated memory. The microcontroller 502 is also arranged to control a 12V boost circuit 518 for increasing voltage to one or more LED arrays 520. The microcontroller 502 further controls one or more LED driver circuits 510 arranged to drive the LED array(s) 520. The microcontroller 502 is also arranged to receive inputs from a user input button 504, a temperature sensor 524, and a proximity sensor 526 (which includes an infrared LED 528). The microcontroller 502 is further arranged to provide output signals to a LCD display 506 and a buzzer 508. Certain components are located off-board relative to a controller PCB, as indicated by the vertical dashed line in FIG. 40. In operation of the light emitting device, a user may depress the button 504 to start operation. If the proximity sensor 526 detects that the device has been placed in suitable proximity to desired tissue, then the microcontroller 502 may trigger the LED driver circuit(s) 510 to energize the LED array(s) 520. Temperature during operation is monitored with the temperature sensor 524. If an excess temperature condition is detected, then the microcontroller 502 may take appropriate action to reduce current supplied by the LED driver circuit(s) 510 to the LED array(s) 520. Operation may continue until a timer (e.g., internal to the microcontroller 502) causes operation to terminate automatically. One or more indicator LEDs (not shown) may provide a visible signal indicative of charging status of the battery 522. Audible signals for commencement and termination of operation may be provided by the buzzer 508 or a suitable speaker. Information relating to usage cycles, usage time, or any other suitable parameter may be displayed by the LCD display 506.

Figure 41:
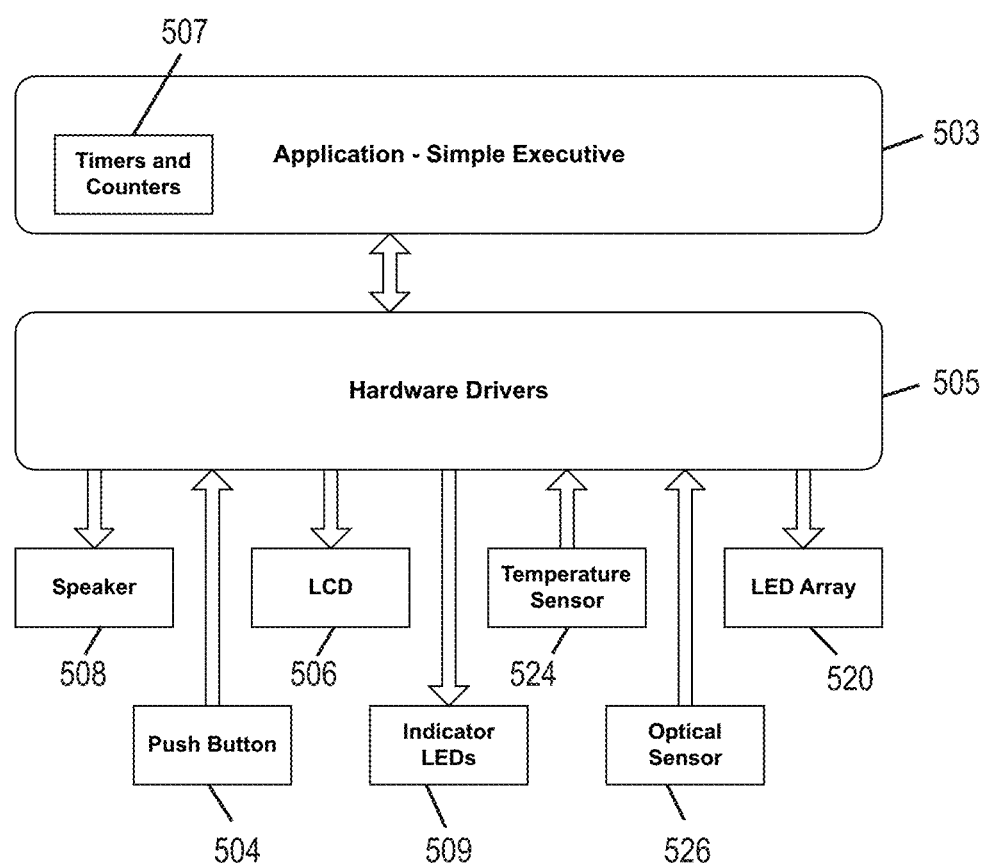
FIG. 41 is a schematic diagram depicting an interface between hardware drivers, functional components, and a software application suitable for operating a light emitting device according to FIG. 40.

FIG. 41 is a schematic diagram depicting an interface between hardware drivers, functional components, and a software application suitable for operating a light emitting device according to FIG. 40. Application executive functions 503, including timers and counters 507, may be performed with one or more integrated circuits (such as the microcontroller 502 illustrated in FIG. 40). Hardware drivers 505 may be used to interface with various input and output elements, such as the LED array(s) 520, the speaker or buzzer 508, the LCD display 506, the temperature sensor 524, the push button 504, the indicator LEDs 509, and the optical sensor (proximity sensor) 526.

FIG. 42 is a schematic elevation view of at least a portion of a light emitting device 600 for delivering light energy to tissue in an internal cavity (e.g., body cavity) of a patient according to one embodiment. In certain embodiments, a body cavity may comprise a vaginal cavity, an oral cavity, or an esophageal cavity. If used in an oral or esophageal cavity, one or more unobstructed channels or tubes (not shown) may be provided in, on, or through the device 600 to avoid interruption with patient breathing. The device 600 includes a body 601 that may be rigid, semi-rigid, or articulated. A treatment head 603 has arranged therein or thereon one or more light emitters 605, which are preferably encapsulated in silicone or another suitable light transmissive material. In certain embodiments, the one or more light emitters 605 may be arranged to produce ES increasing light and ES releasing light for impingement on tissue located within an internal cavity of a patient to trigger release of NO. In certain embodiments, the light emitters may be external to the body 601, and light emissions of the light emitters may be extracted at features that are arranged on the end of the body 601 (e.g., in or along treatment head 603), and light may exit the treatment head 603 at apertures or positions corresponding to element number 605.

FIG. 43A is a schematic elevation view of at least a portion of a light emitting device 610 including a concave light emitting surface 614 including one or more light emitters 615 for delivering light energy to cervical tissue of a patient according to one embodiment. The device 610 includes a body 611 that may be rigid, semi-rigid, or articulated. A joint 612 may be arranged between the body 611 and a treatment head 613. The treatment head 613 has arranged therein or thereon the one or more light emitters 615, which are preferably encapsulated in silicone or another suitable light transmissive material. In certain embodiments, the one or more light emitters 615 may be configured to generate emissions suitable for neutralizing pathogens such as human papilloma virus (HPV) present on cervical tissue. In certain embodiments, the one or more light emitters 615 may be arranged to produce ES increasing light and ES releasing light for impingement on tissue located within an internal cavity of a patient to trigger release of NO.

FIG. 43B illustrates the device 610 of FIG. 43A inserted into a vaginal cavity 650 to deliver light energy to cervical tissue 655 of a patient proximate to a cervical opening 656. The concave light emitting surface 614 may be configured to approximately match a convex profile of the cervical tissue 655.

FIG. 44A is a schematic elevation view of at least a portion of a light emitting device 620 including a light emitting surface 624 with a protruding probe portion 626 for delivering light energy to cervical tissue of a patient according to another embodiment. The probe portion 626 includes light emitters and is arranged to deliver light energy into a cervical opening. The device 620 includes a body 621 that may be rigid, semi-rigid, or articulated. A joint 622 may be arranged between the body 621 and a treatment head 623. The treatment head 623 has arranged therein or thereon one or more light emitters 625, which are preferably encapsulated in silicone or another suitable light transmissive material. The treatment head 623 may include the light emitting surface 624, which may optionally be convex to cast a wider output beam. In certain embodiments, the one or more light emitters 625 may be configured to generate emissions suitable for neutralizing pathogens such as human papilloma virus (HPV) present on cervical tissue. In certain embodiments, the one or more light emitters 625 may be arranged to produce ES increasing light and ES releasing light for impingement on tissue located within an internal cavity of a patient to trigger release of NO.

FIG. 44B illustrates the device 620 of FIG. 44A inserted into a vaginal cavity 650 to deliver light energy to cervical tissue 655 of a patient proximate and within to a cervical opening 656. The primary light emitting surface 624 may be arranged to impinge light on cervical tissue bounding the vaginal cavity 650, whereas the probe portion 626 may be inserted into the cervical opening 656 to deliver additional light energy therein to increase the amount of cervical tissue subject to receipt of light energy for addressing one or more conditions including pathogen (e.g., HPV) neutralization.

To investigate whether NO may be photomodulated in at least certain types of cells for extended periods (e.g., hours) and to evaluate potential toxicity of photomodulation, Applicant performed various experiments on two types of cells—namely, ketatinocytes and fibroblasts.

Figure 45:
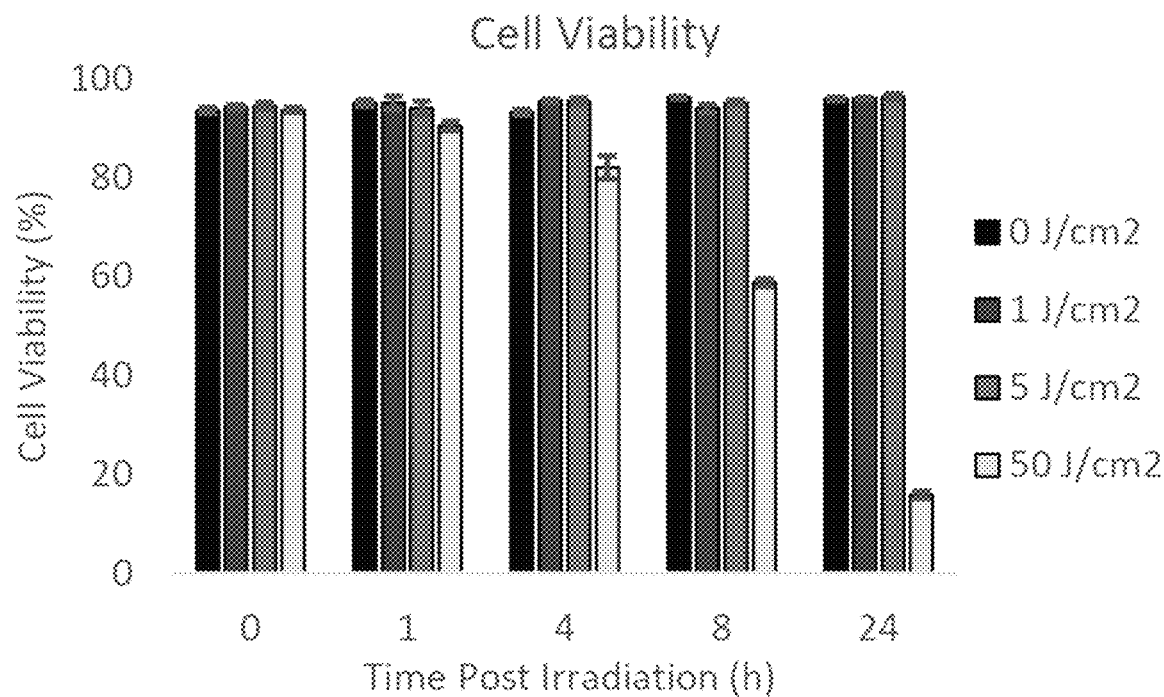
FIG. 45 is a bar chart identifying percentage of viable cells as a function of time post 420 nm irradiation (from 0 to 24 hours) for four different fluence values ranging from 0 $J/cm^2$ to 50 $J/cm^2$ for NO generation in keratinocytes resulting from photobiomodulation.

Referring to FIGS. 45-48, isolated ketatinocytes were exposed to 420 nm light to achieve doses of 0, 1, 5, and 50 J/cm$^2$. Fluence of light was found to determine efficacy of NO modulation as well as cytotoxicity. As shown in FIG. 45, cell viability over periods from 0 to 24 hours from light exposure was unaffected by doses of 0, 1, and 5 J/cm$^2$, but light exposure at 50 J/cm$^2$ resulted in a substantial drop in cell viability, declining to a value below 20% within 24 hours after irradiation.

Figure 46:
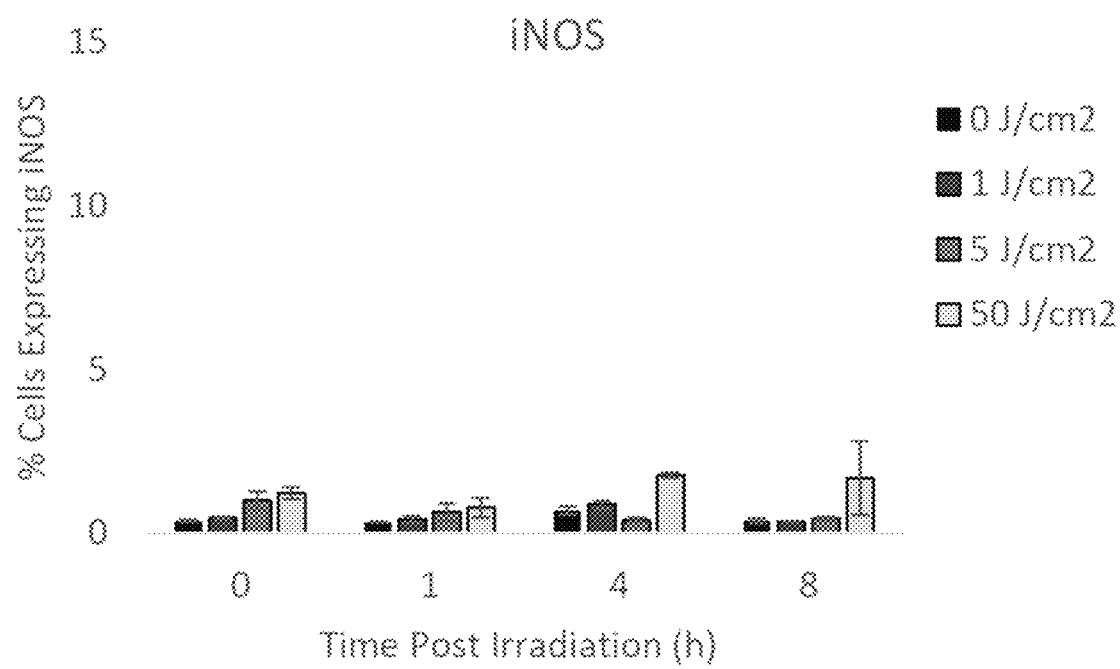
FIG. 46 is a bar chart identifying percentage of cells expressing iNOS as a function of time post 420 nm irradiation (from 0 to 8 hours) for four different fluence values ranging from 0 $J/cm^2$ to 50 $J/cm^2$ for NO generation in keratinocytes resulting from photobiomodulation.
Figure 47:
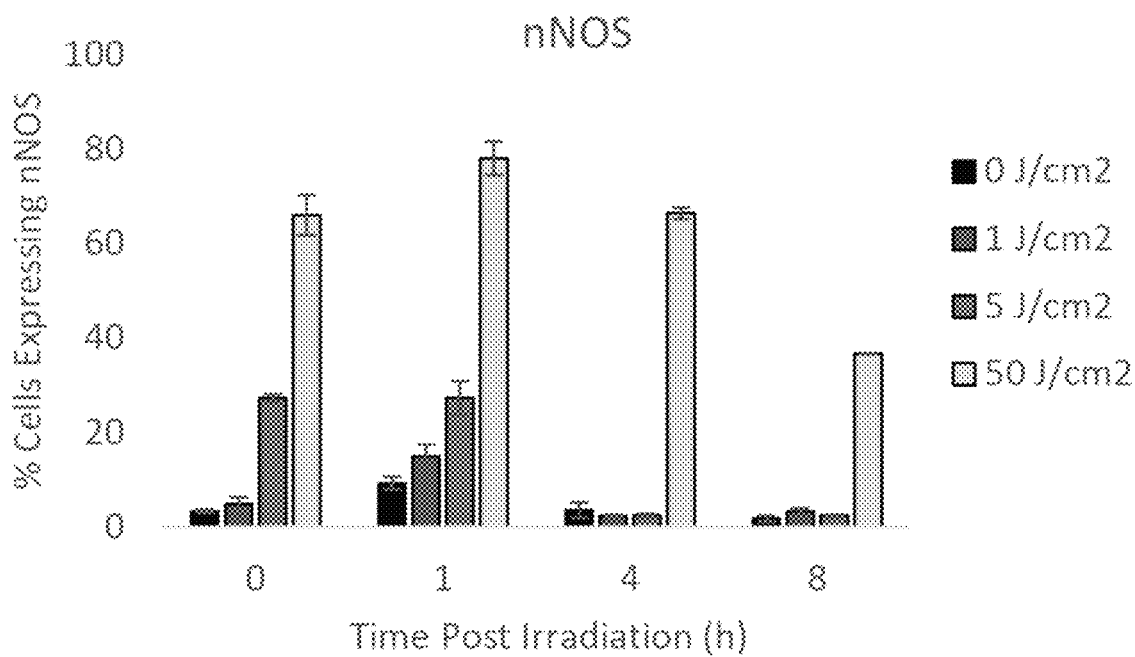
FIG. 47 is a bar chart identifying percentage of cells expressing nNOS as a function of time post 420 nm irradiation (from 0 to 8 hours) for four different fluence values ranging from 0 $J/cm^2$ to 50 $J/cm^2$ for NO generation in keratinocytes resulting from photobiomodulation.

Referring to FIGS. 46 and 47, the amount of NOS enzymes (namely, iNOS in FIG. 46, and nNOS in FIG. 47) expressed in the keratinocyte cells was quantified at intervals of 0 hours (immediately), 1 hour, 4 hours, and 8 hours after irradiation ended. The number of cells exhibiting iNOS and nNOS increased with increasing irradiation. In FIG. 46, the percentage of cells expressing iNOS generally remained the same or decreased 1 hour after light exposure; the percentage of cells expressing iNOS increased for doses of 1 and 50 J/cm$^2$ at a time 4 hours after light exposure, and the percentage of cells expressing iNOS remained elevated only for the dose of 50 J/cm$^2$ at a time 24 hours after light exposure. In FIG. 47, the percentage of cells expressing nNOS generally increased for all doses of 0, 1, 5, and 50 J/cm$^2$ at a time 1 hour after light exposure, the percentage of cells expressing nNOS remained elevated only for the dose of 50 J/cm$^2$ at a time period of 4 hours and 8 hours after light exposure. FIGS. 46 and 47 show the capability of generated nitric oxide synthases with photomodulation.

Figure 48:
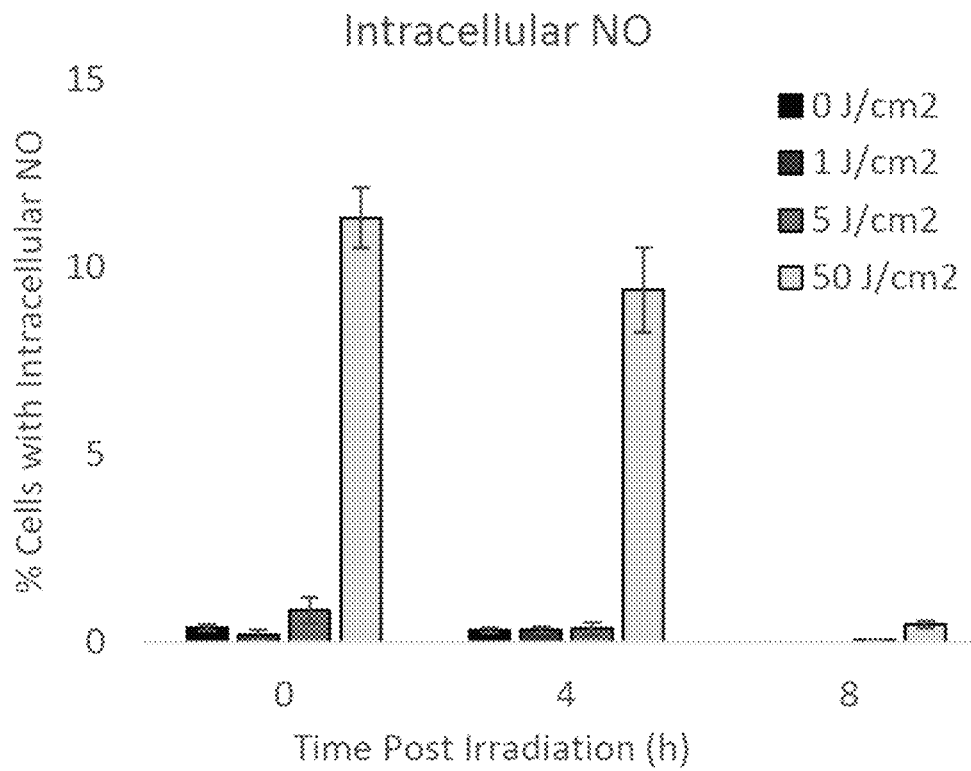
FIG. 48 is a bar chart identifying percentage of cells with intracellular NO as a function of time post 420 nm irradiation (from 0 to 8 hours) for four different fluence values ranging from 0 $J/cm^2$ to 50 $J/cm^2$ for NO generation in keratinocytes resulting from photobiomodulation.

Referring to FIG. 48, intracellular NO was measured with 4-Amino-5-Methylamino-2',7'-Difluorofluorescein Diacetate (DAF-FM Diacetate). The number of cells exhibiting intracellular NO increased with increasing irradiation. Intracellular NO was measured immediately after light exposure as well as 4 and 8 hours after exposure. FIG. 48 shows that NO is released for greater than 4 hours after irradiation, thereby suggesting enzymatic NO generation.

Figure 49:
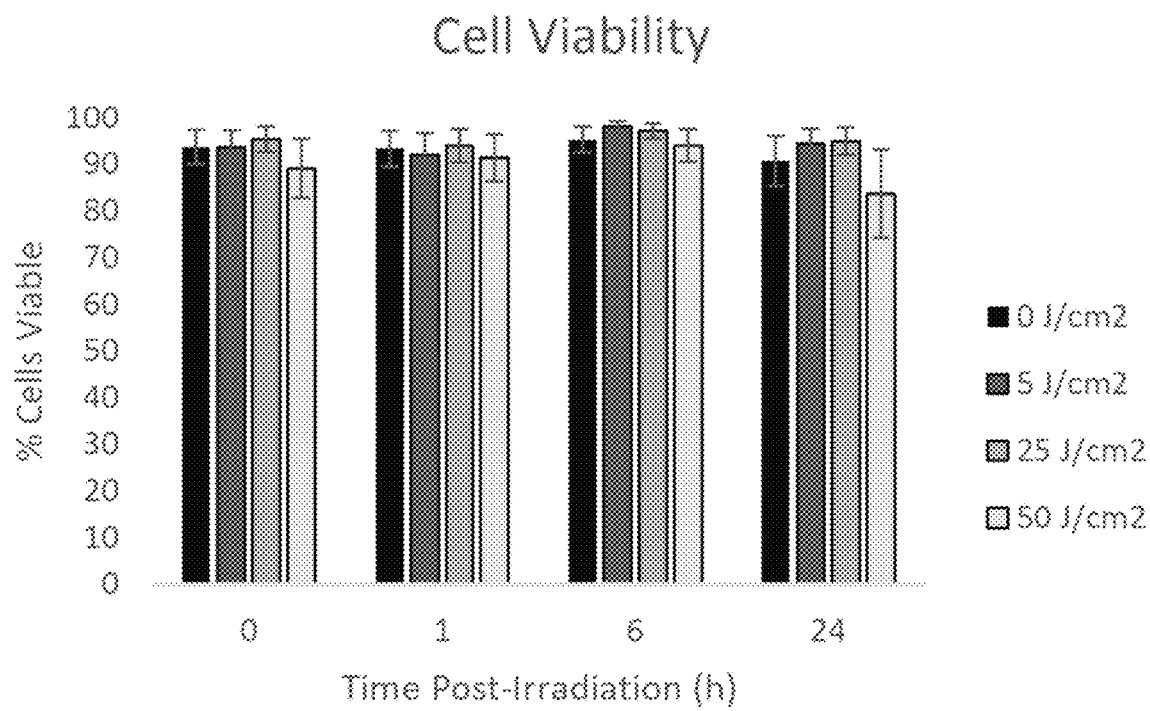
FIG. 49 is a bar chart identifying percentage of viable cells as a function of time post 420 nm irradiation (from 0 to 24 hours) for four different fluence values ranging from 0 $J/cm^2$ to 50 $J/cm^2$ for NO generation in fibroblasts resulting from photobiomodulation.

Turning to FIGS. 49-52, isolated fibroblasts were exposed to 420 nm light to achieve doses of 0, 5, 25, and 50 J/cm$^2$. Fluence of light was found to determine efficacy of NO modulation as well as cytotoxicity. As shown in FIG. 49, cell viability over periods from 0 to 24 hours from light exposure was substantially unaffected by doses of 0, 5, 25, and 50 J/cm$^2$.

Figure 50:
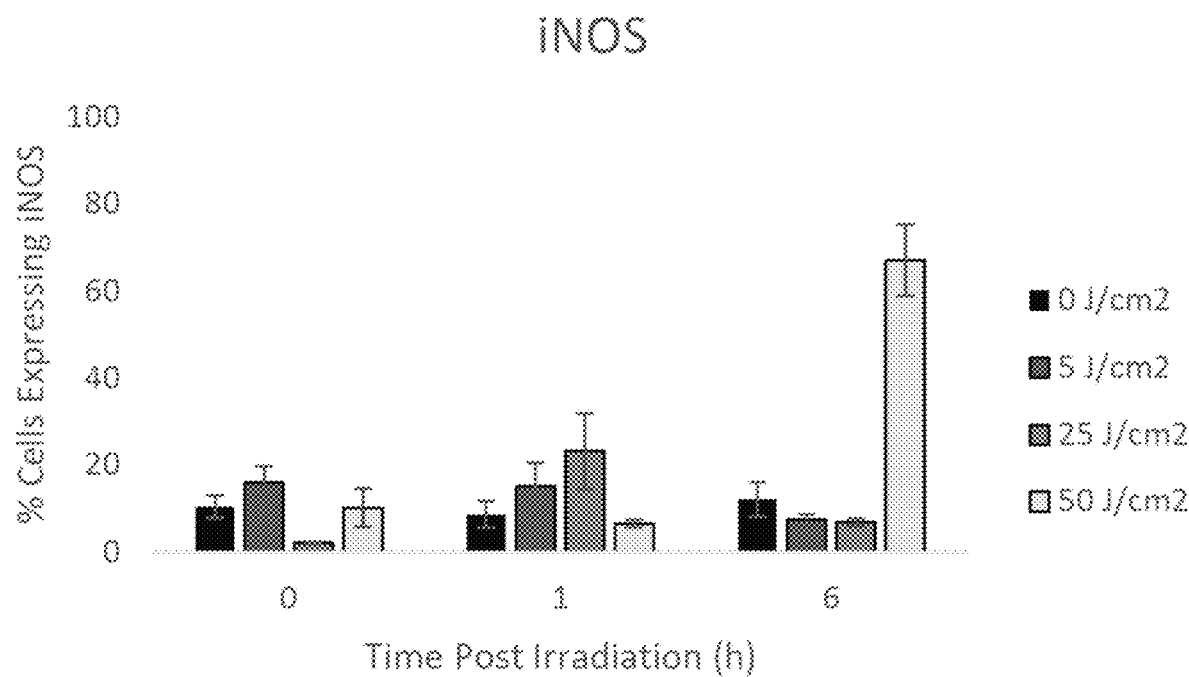
FIG. 50 is a bar chart identifying percentage of cells expressing iNOS as a function of time post 420 nm irradiation (from 0 to 6 hours) for four different fluence values ranging from 0 $J/cm^2$ to 50 $J/cm^2$ for NO generation in fibroblasts resulting from photobiomodulation.
Figure 51:
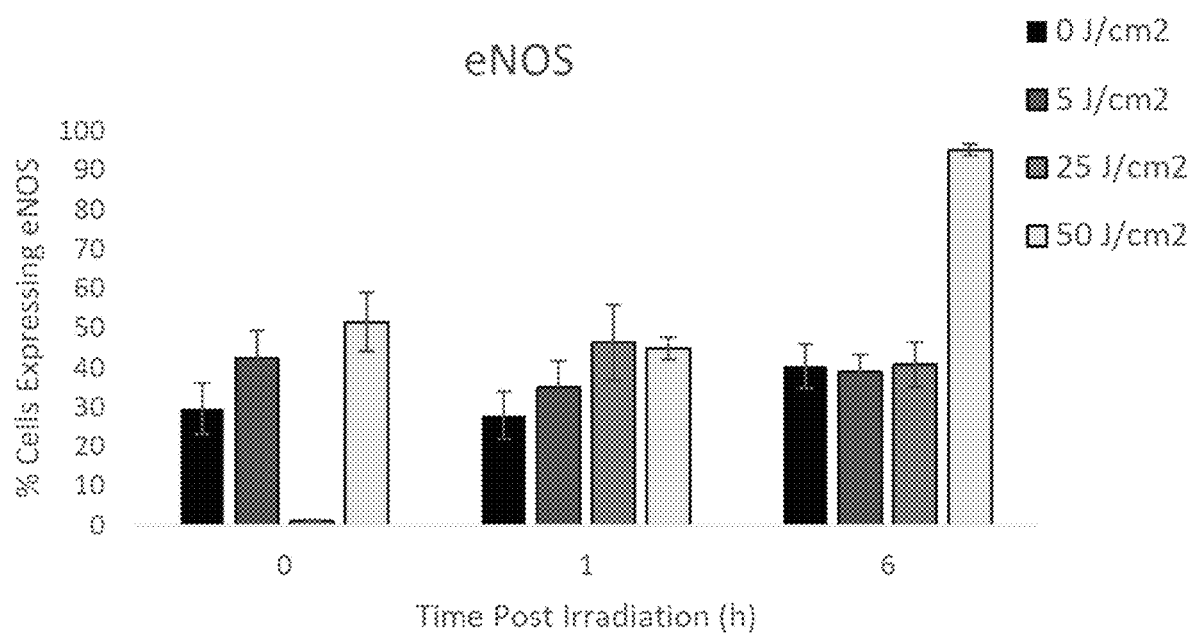
FIG. 51 is a bar chart identifying percentage of cells expressing eNOS as a function of time post 420 nm irradiation (from 0 to 6 hours) for four different fluence values ranging from 0 $J/cm^2$ to 50 $J/cm^2$ for NO generation in fibroblasts resulting from photobiomodulation.

Referring to FIGS. 50 and 51, the amount of NOS enzymes (namely, iNOS in FIG. 50, and eNOS in FIG. 51) expressed in the fibroblast cells was quantified at intervals of 0 hours (immediately), 1 hour, and 6 hours after irradiation ended. In both figures, the number of cells exhibiting iNOS or eNOS generally increased with increasing irradiation. In FIG. 50, the percentage of cells expressing iNOS was particularly elevated for the dose of 50 J/cm² at a time period of 6 hours after irradiation, thereby suggesting enzymatic NO generation. Referring to FIG. 51, the percentage of cells expressing eNOS remained generally elevated at a time period of 6 hours after irradiation, but the dose of 50 J/cm² was particularly elevated at this time period.

Figure 52:
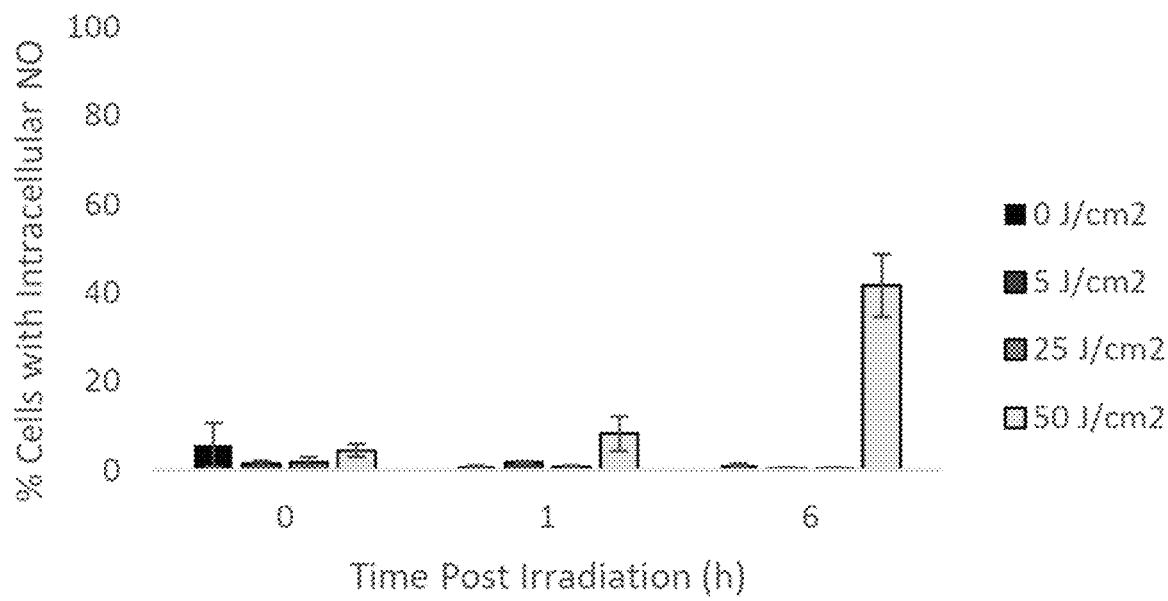
FIG. 52 is a bar chart identifying percentage of cells with intracellular NO as a function of time post 420 nm irradiation (from 0 to 6 hours) for four different fluence values ranging from 0 $J/cm^2$ to 50 $J/cm^2$ for NO generation in fibroblasts resulting from photobiomodulation.

Referring to FIG. 52, intracellular NO was measured with 4-Amino-5-Methylamino-2',7'-Difluorofluorescein Diacetate (DAF-FM Diacetate). The number of cells exhibiting intracellular NO increased with increasing irradiation. Intracellular NO was measured immediately after light exposure as well as 1 and 6 hours after exposure. FIG. 52 shows that NO is released for greater than 4 hours after irradiation, thereby suggesting enzymatic NO generation. The percentage of cells with intracellular NO remained elevated at 1 hour and 6 hours after irradiation for the dose of 50 J/cm², but was particularly elevated at 6 hours for 50 J/cm².

Taken in combination, FIGS. 49-52 demonstrate the capability of generating nitric oxide synthases and NO using 420 nm light for 6 hours post irradiation without associated toxicity.

Efficacy of the liberation of nitric oxide from protein complexes (by breaking nitroso or nitrosyl bonds) depends on the wavelength of light used. Different types of bonds (e.g., RSNO, RNNO, and metal-NO) may require different light wavelength and light irradiation values to effectuate release of nitric oxide. To investigate whether certain light wavelengths and light irradiation values may be more effective than others at releasing different endogenous stores of NO (i.e., to serve as ES releasing light), Applicant performed various experiments with hemoglobin-NO, S-nitrosoglutathione (GSNO), albumin-NO, cytochrome c-NO, cytochrome c-oxidase-NO, and mitochondria-NO. Details of these experiments are described hereinafter in connection with FIGS. 53 to 64.

Figure 53:
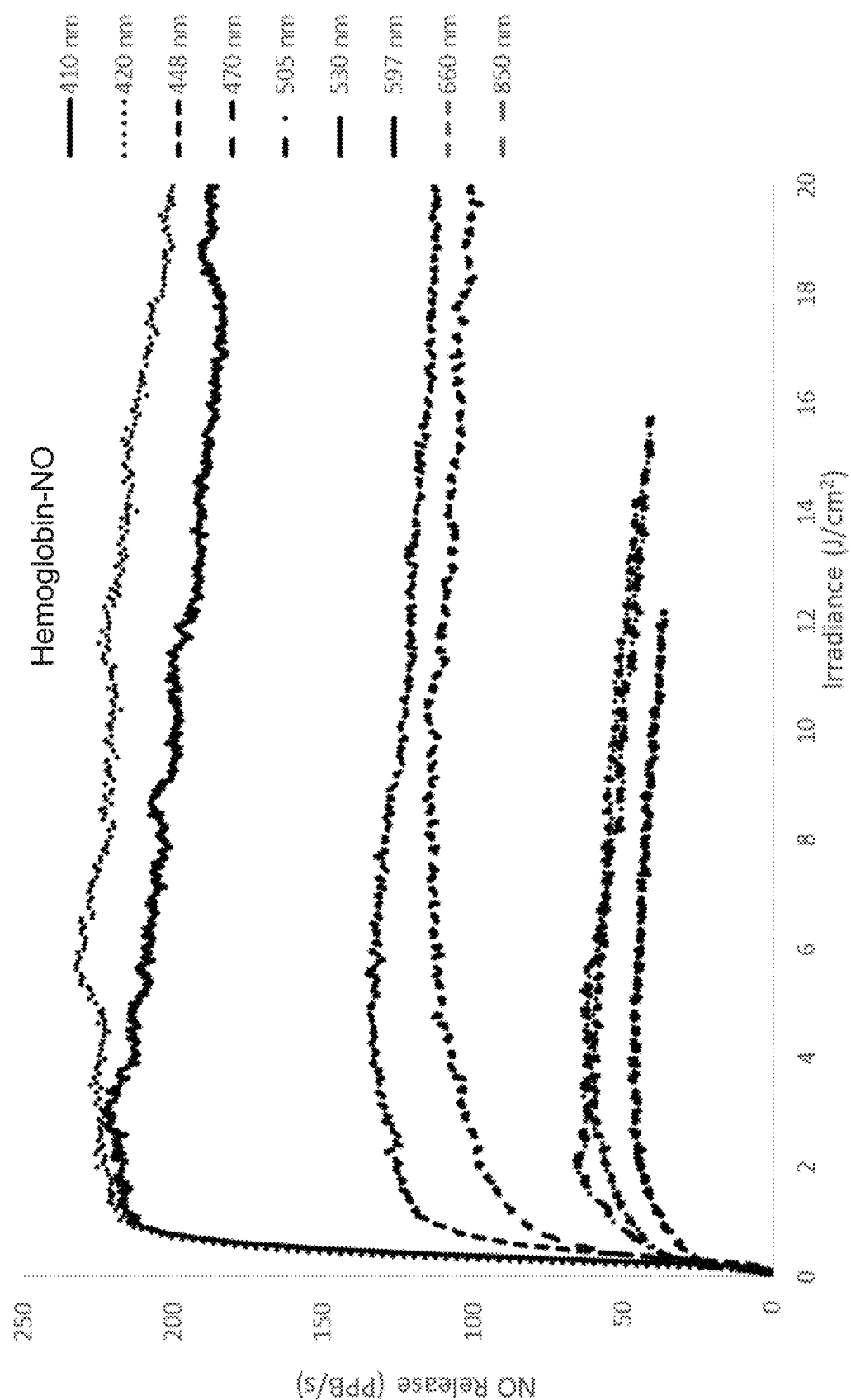
FIG. 53 is a plot of NO release rate (PPB/s) versus irradiance (J/cm$^2$) from hemoglobin-NO for nine (9) different wavelengths of incoherent light ranging from 410 nm to 850 nm.
Figure 54:
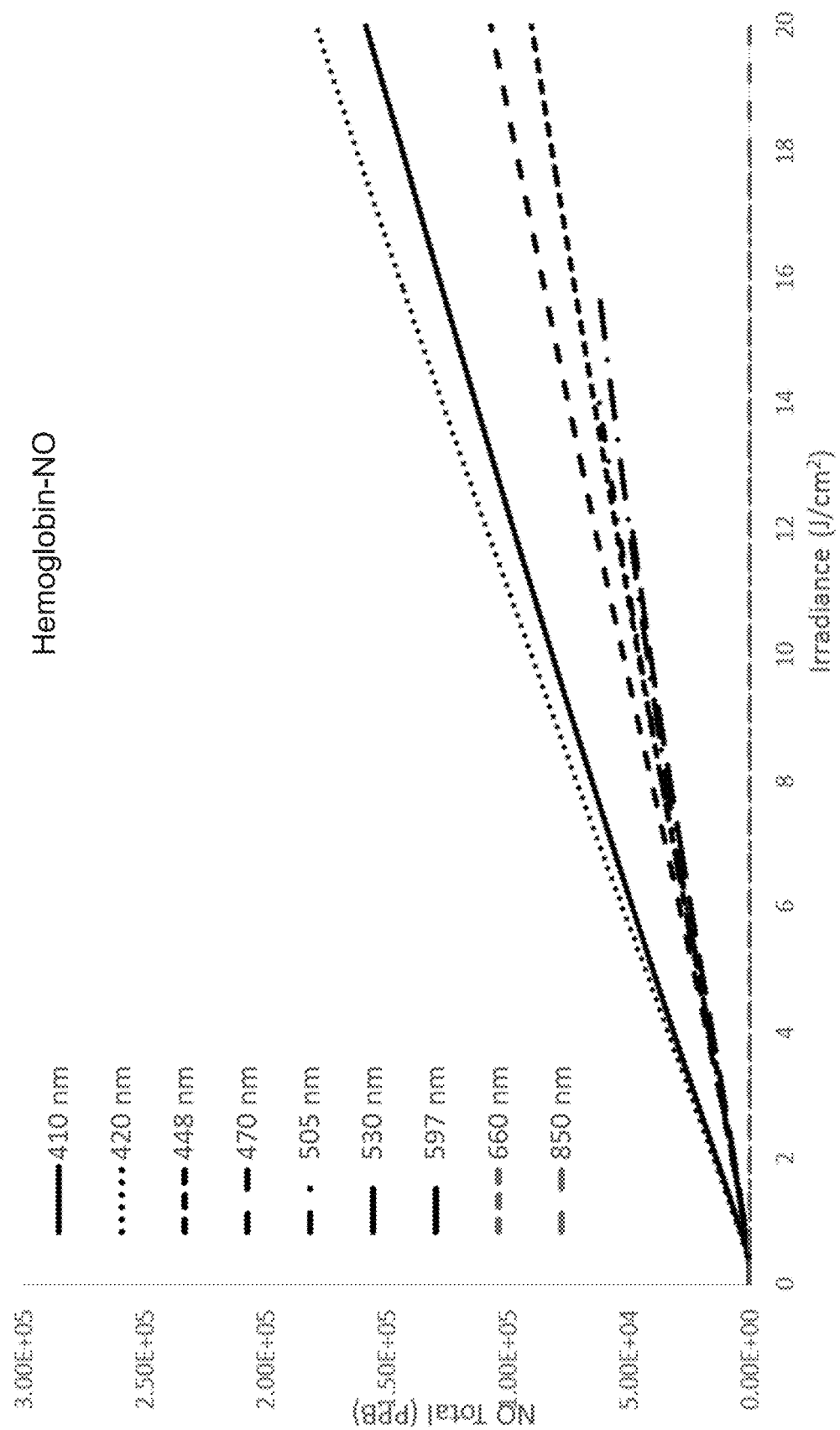
FIG. 54 is a plot of total NO release (PPB) versus irradiance (J/cm$^2$) from hemoglobin-NO for nine (9) different wavelengths of incoherent light ranging from 410 nm to 850 nm.

FIG. 53 is a plot of NO release rate (PPB/s) versus irradiance (J/cm²) from hemoglobin-NO for nine (9) different wavelengths of incoherent light ranging from 410 nm to 850 nm. Nitric oxide was added to hemoglobin by reacting proline-NONOate with hemoglobin in PBS (pH 6.5) under anaerobic conditions and in the dark. After 45 minutes of reaction, the NO release was measured as a function of irradiation using a chemiluminescence detector. As shown, all wavelengths resulted in release of NO (at a roughly constant rate for all irradiance values greater than about 2 J/cm²), but the release rate was highest for 420 nm light, second highest for 410 nm light, and lowest for longer wavelengths (e.g., 850 nm light). Referring to FIG. 54, total NO released from hemoglobin was quantified by integrating the data on NO release rate of FIG. 53. A linear relationship is observed for each wavelength, with higher irradiance values resulting in higher total NO release. The highest amount of total NO release was achieved with 420 nm light, the second highest amount was achieved with 410 nm light, and the lowest amount of total NO release was achieved with 597 nm light. Notably, FIG. 54 omits data for 660 nm light and 850 nm light.

Figure 55:
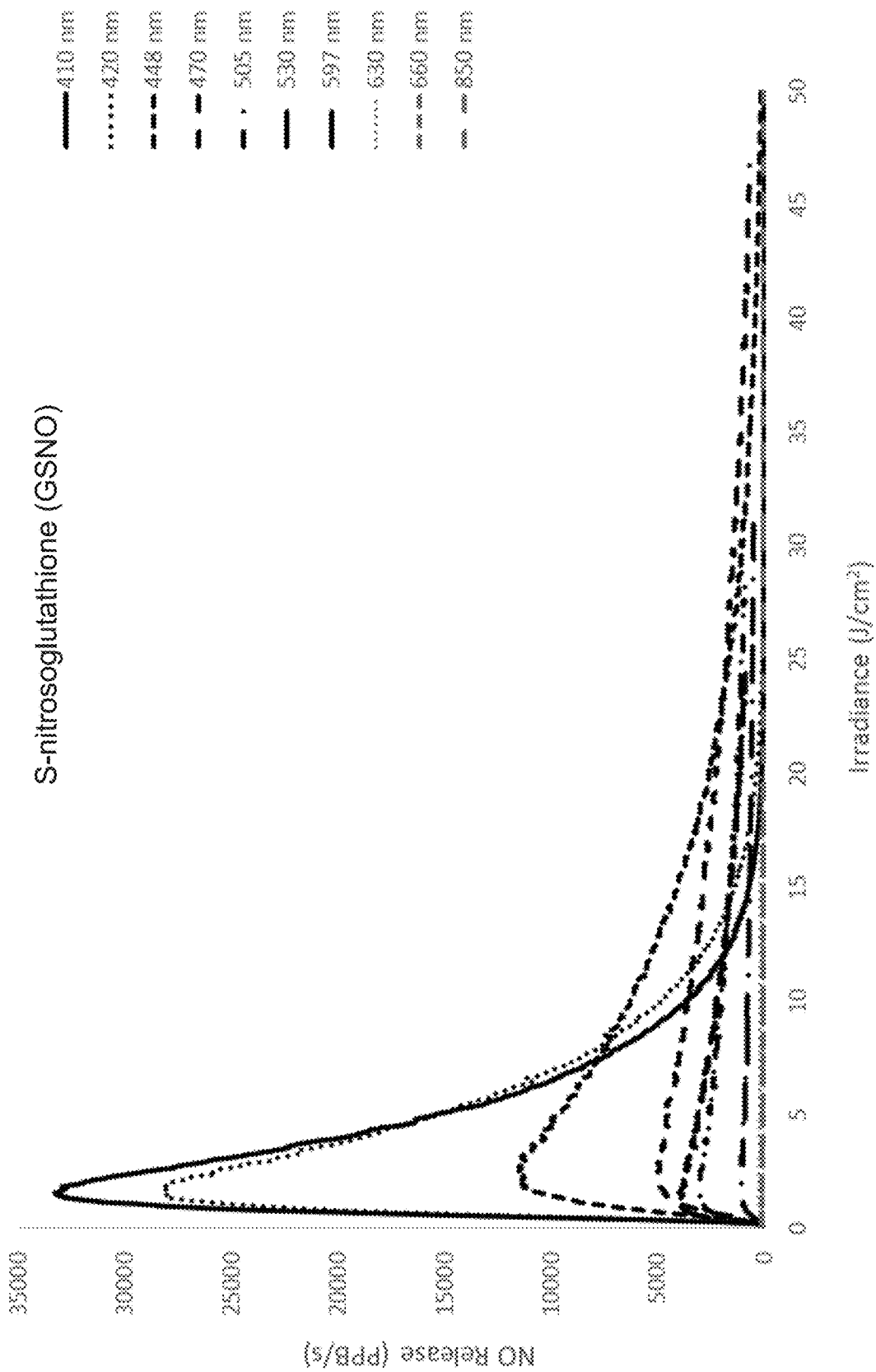
FIG. 55 is a plot of NO release rate (PPB/s) versus irradiance (J/cm$^2$) from S-nitrosoglutathione (GSNO) for ten (10) different wavelengths of incoherent light ranging from 410 nm to 850 nm.
Figure 56:
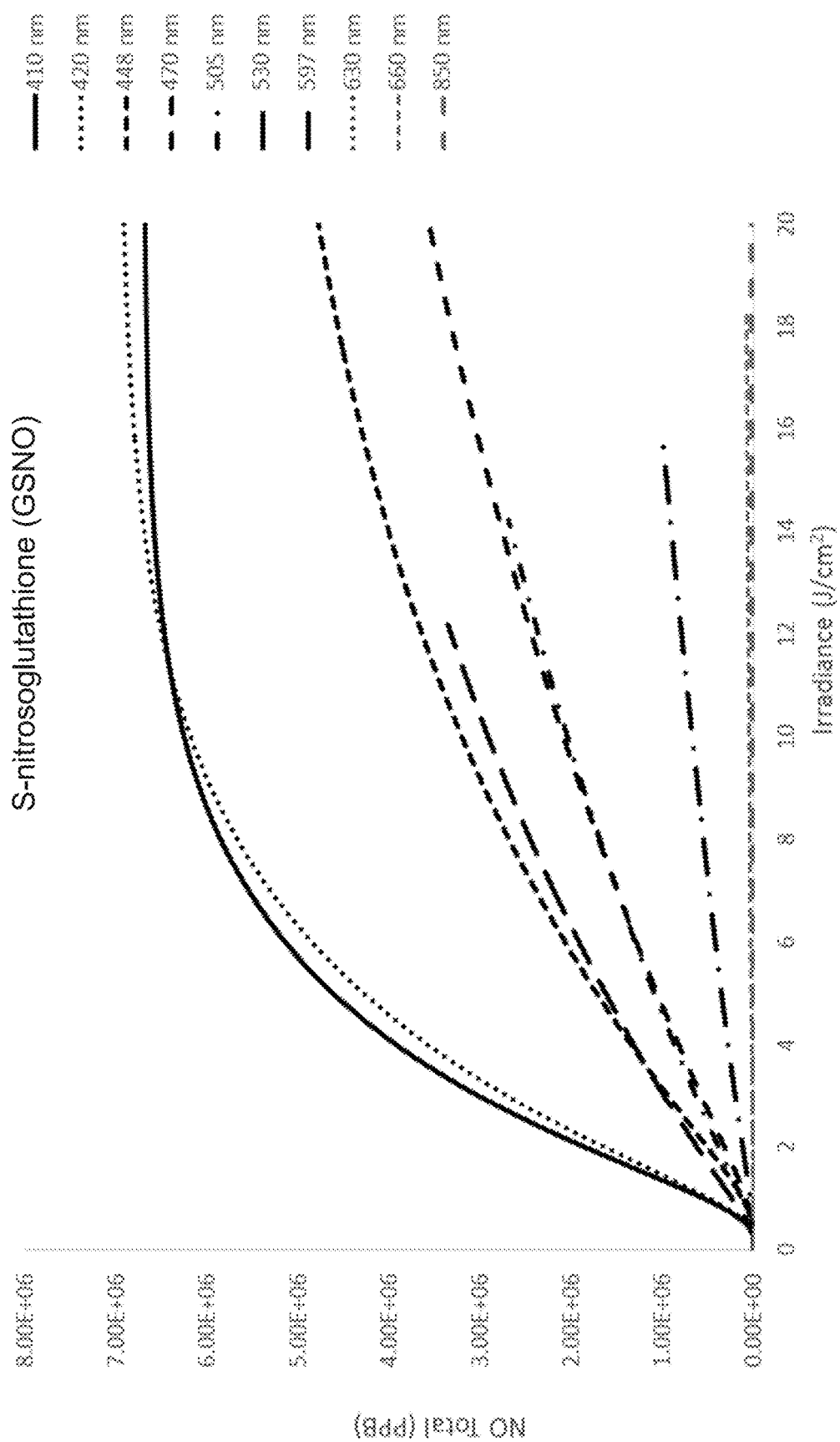
FIG. 56 is a plot of total NO release (PPB) versus irradiance (J/cm$^2$) from S-nitrosoglutathione (GSNO) for ten (10) different wavelengths of incoherent light ranging from 410 nm to 850 nm.

FIG. 55 is a plot of NO release rate (PPB/s) versus irradiance (J/cm2) from S-nitrosoglutathione (GSNO) for ten (10) different wavelengths of incoherent light ranging from 410 nm to 850 nm. The NO-release from S-nitrosoglutathione was measured in PBS (pH 6.5), at room temperature as a function of irradiation via chemiluminescent detection. As shown, all wavelengths resulted in some release of NO, but the release rate was highest for the shortest wavelength (410 nm) light and lowest for the longest wavelength (850 nm) light. Referring to FIG. 56, total NO released from hemoglobin was quantified by integrating the data on NO release rate of FIG. 55. The highest amounts of total NO release were achieved with 410 nm and 420 nm light, and the lowest amount of total NO release was achieved with 850 nm light.

Figure 57:
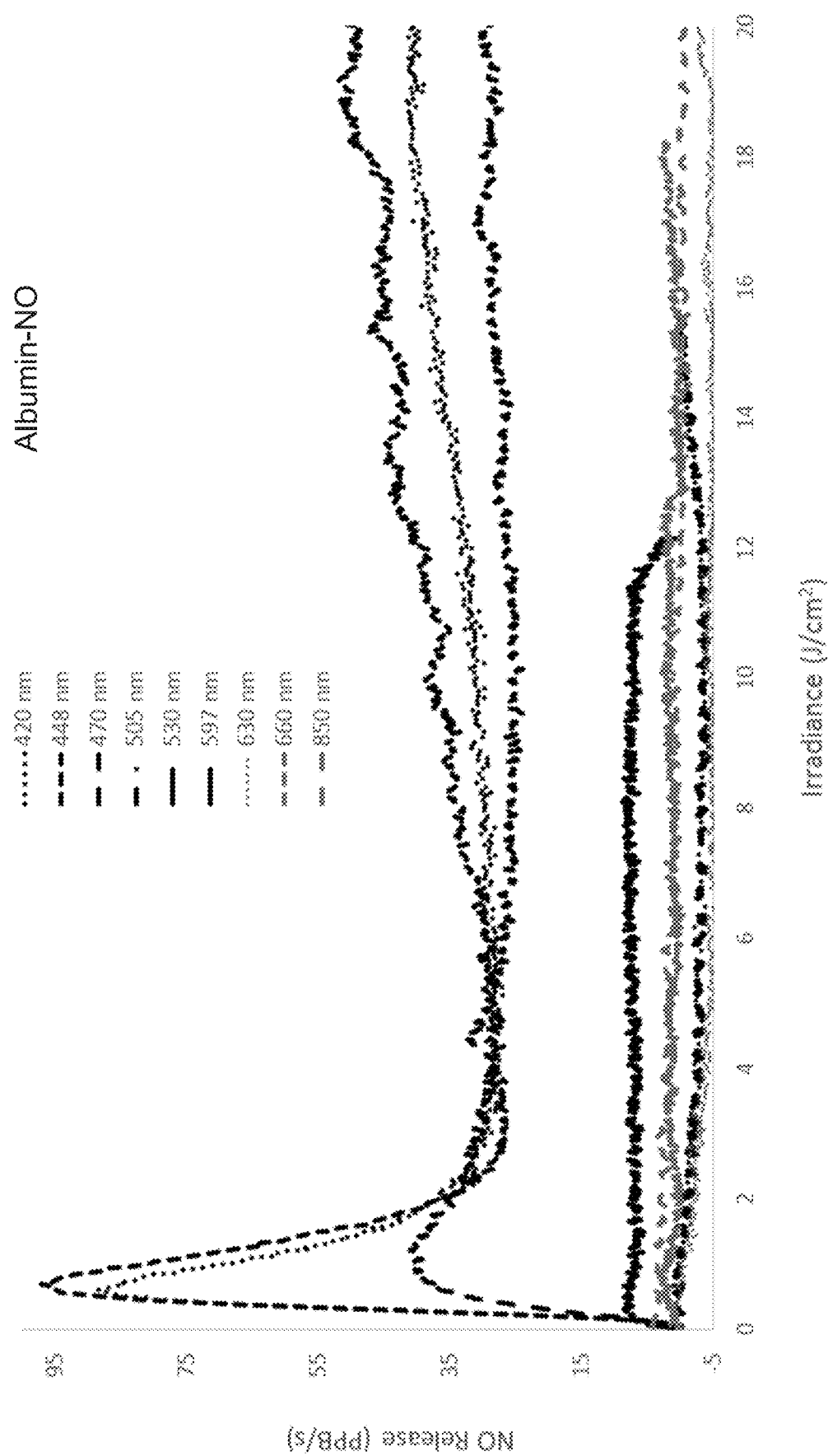
FIG. 57 is a plot of NO release rate (PPB/s) versus irradiance (J/cm$^2$) from albumin-NO for nine (9) different wavelengths of incoherent light ranging from 420 nm to 850 nm.
Figure 58:
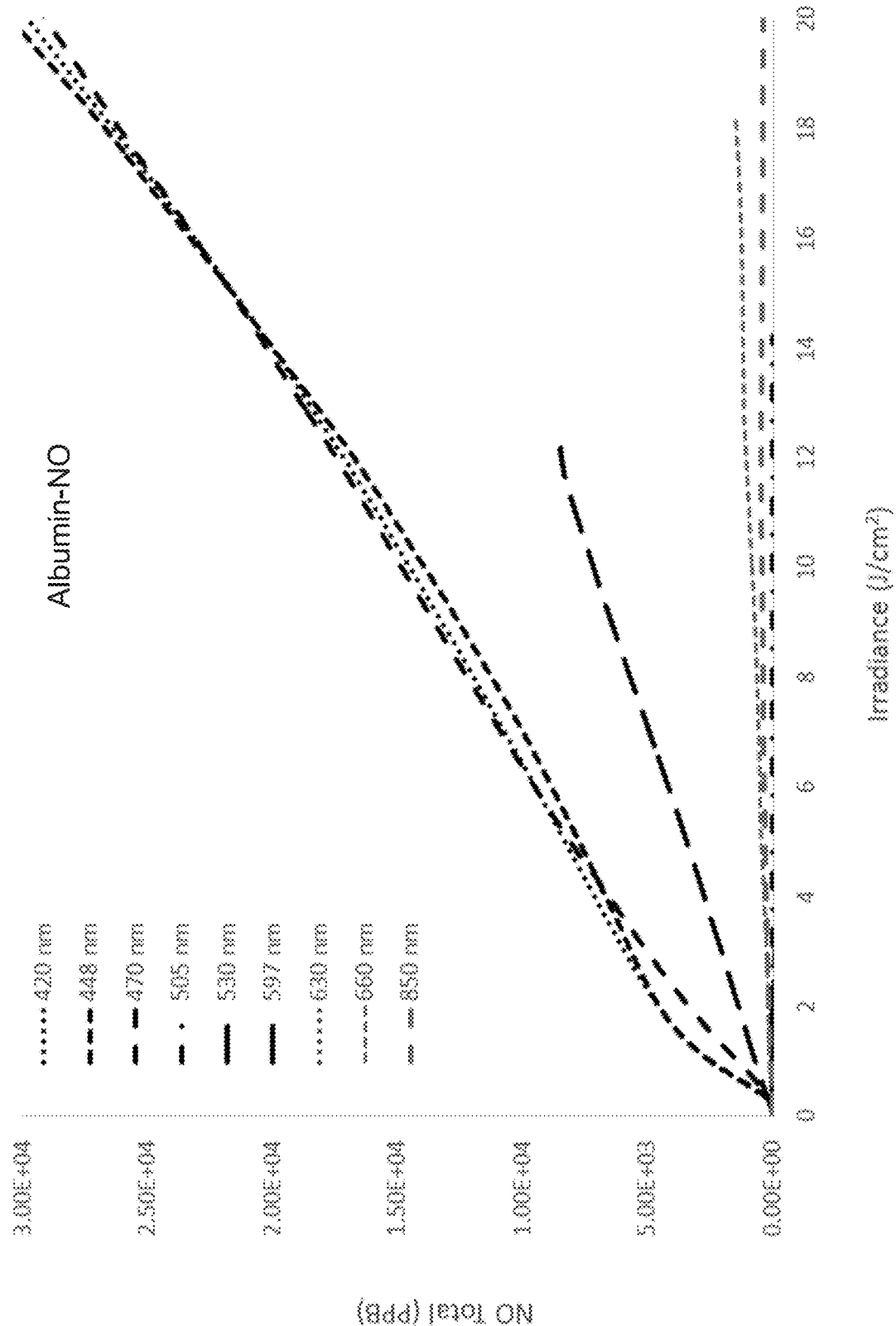
FIG. 58 is a plot of total NO release (PPB) versus irradiance (J/cm$^2$) from albumin-NO for nine (9) different wavelengths of incoherent light ranging from 420 nm to 850 nm.

FIG. 57 is a plot of NO release rate (PPB/s) versus irradiance (J/cm²) from albumin-NO for nine (9) different wavelengths of incoherent light ranging from 420 nm to 850 nm. Nitric oxide was added to bovine serum albumin by reacting with proline-NONOate in PBS (pH 6.5) under anaerobic conditions and in the dark. After 45 minutes of reaction, the NO release was measured as a function of irradiation using a chemiluminescence detector. As shown, the highest NO release rate was achieved for the wavelength of 448 nm, and the second and third highest NO release rates were achieved for wavelengths of 420 nm and 470 nm, respectively, with each of the foregoing three wavelengths causing an initial spike or increase in NO release rate followed by a lower release rate. Referring to FIG. 58, total NO released from albumin-NO was quantified by integrating the data on NO release rate of FIG. 57. Similar amounts of total NO release were achieved for 420 nm light, 448 nm light, and 470 nm light. An intermediate amount of total NO release was achieved for 505 nm light. Relatively little total NO release was achieved for light of other wavelengths.

Figure 59:
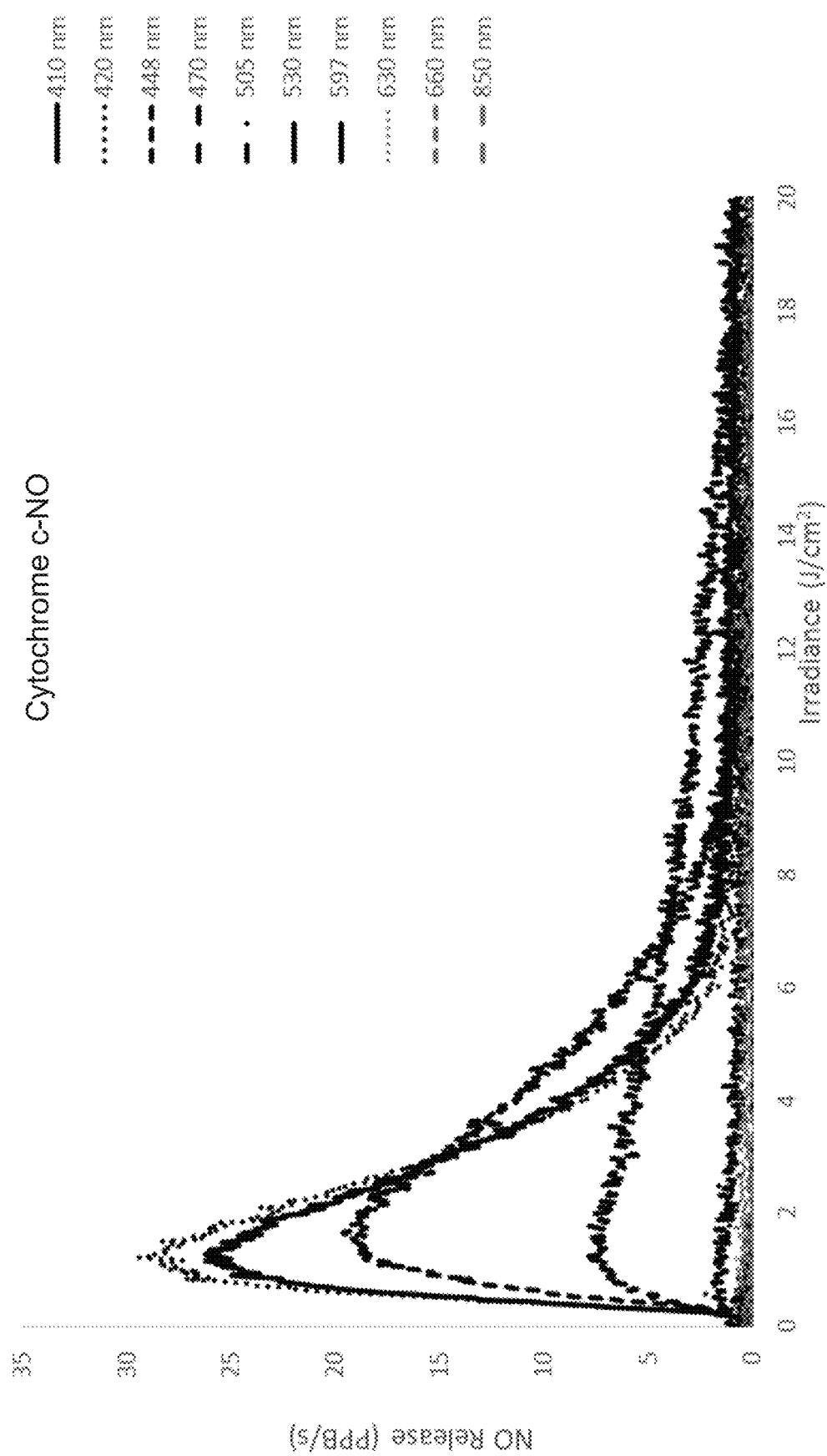
FIG. 59 is a plot of NO release rate (PPB/s) versus irradiance (J/cm$^2$) from cytochrome c-NO for ten (10) different wavelengths of incoherent light ranging from 410 nm to 850 nm.
Figure 60:
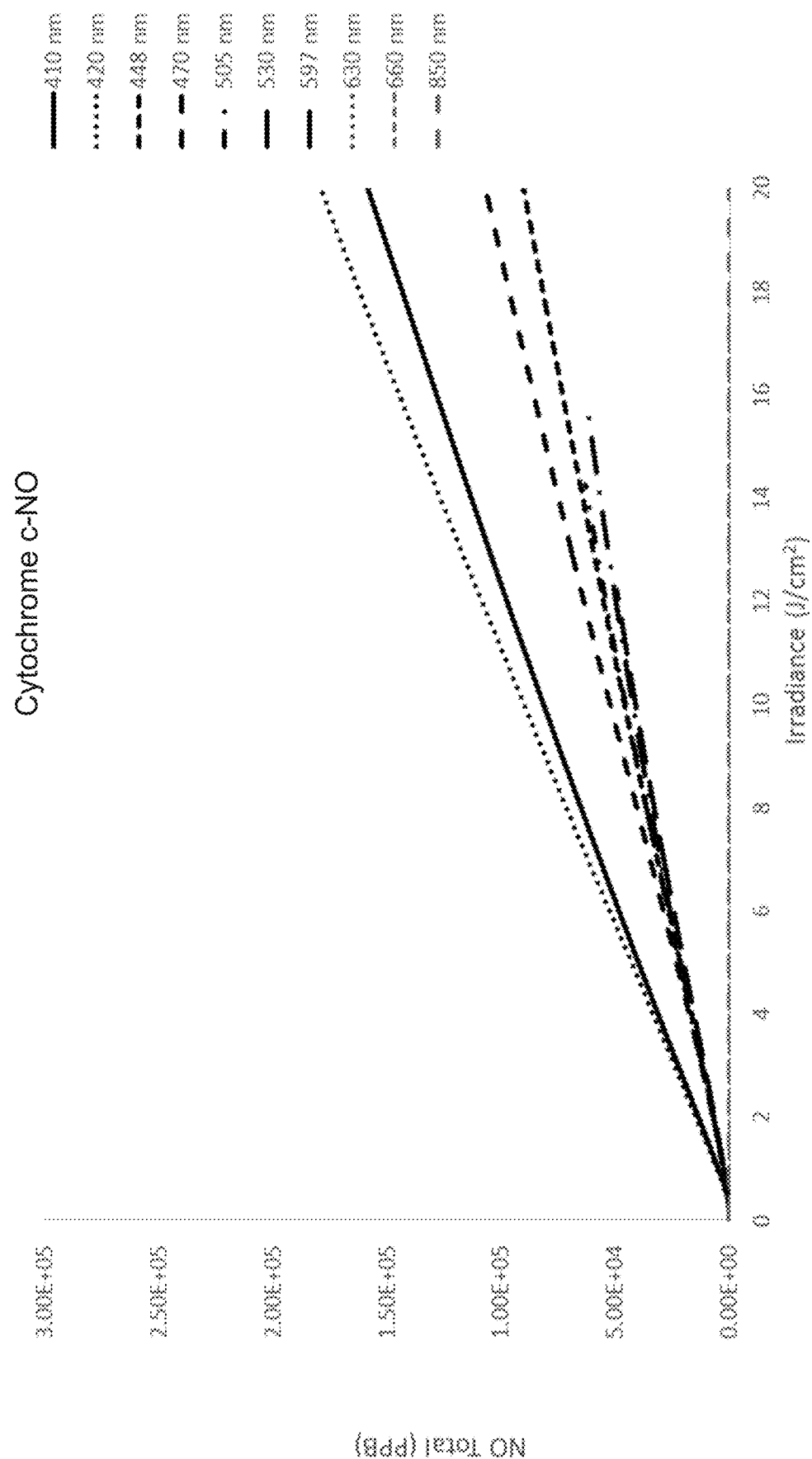
FIG. 60 is a plot of total NO release (PPB) versus irradiance (J/cm$^2$) from cytochrome c-NO for ten (10) different wavelengths of incoherent light ranging from 410 nm to 850 nm.

FIG. 59 is a plot of NO release rate (PPB/s) versus irradiance (J/cm²) from cytochrome c-NO for ten (10) different wavelengths of incoherent light ranging from 410 nm to 850 nm. Nitric oxide was added to cytochrome c by reacting proline-NONOate in PBS (pH 6.5) under anaerobic conditions and in the dark. After 45 minutes of reaction, the NO release was measured as a function of irradiation using a chemiluminescence detector. As shown, the highest four NO release rates were achieved for 420 nm light, 410 nm light, 448 nm light, and 470 nm light, respectively, with each exhibiting a peak release rate near an irradiance value of about 2 J/cm², while all wavelengths exhibiting a reduced or negligible NO release rate as irradiance values approached 20 J/cm². Referring to FIG. 60, total NO released from cytochrome c-NO was quantified by integrating the data on NO release rate of FIG. 59. As shown, the highest four amounts of total NO release were achieved for 420 nm light, 410 nm light, 448 nm light, and 470 nm light, respectively.

Figure 61:
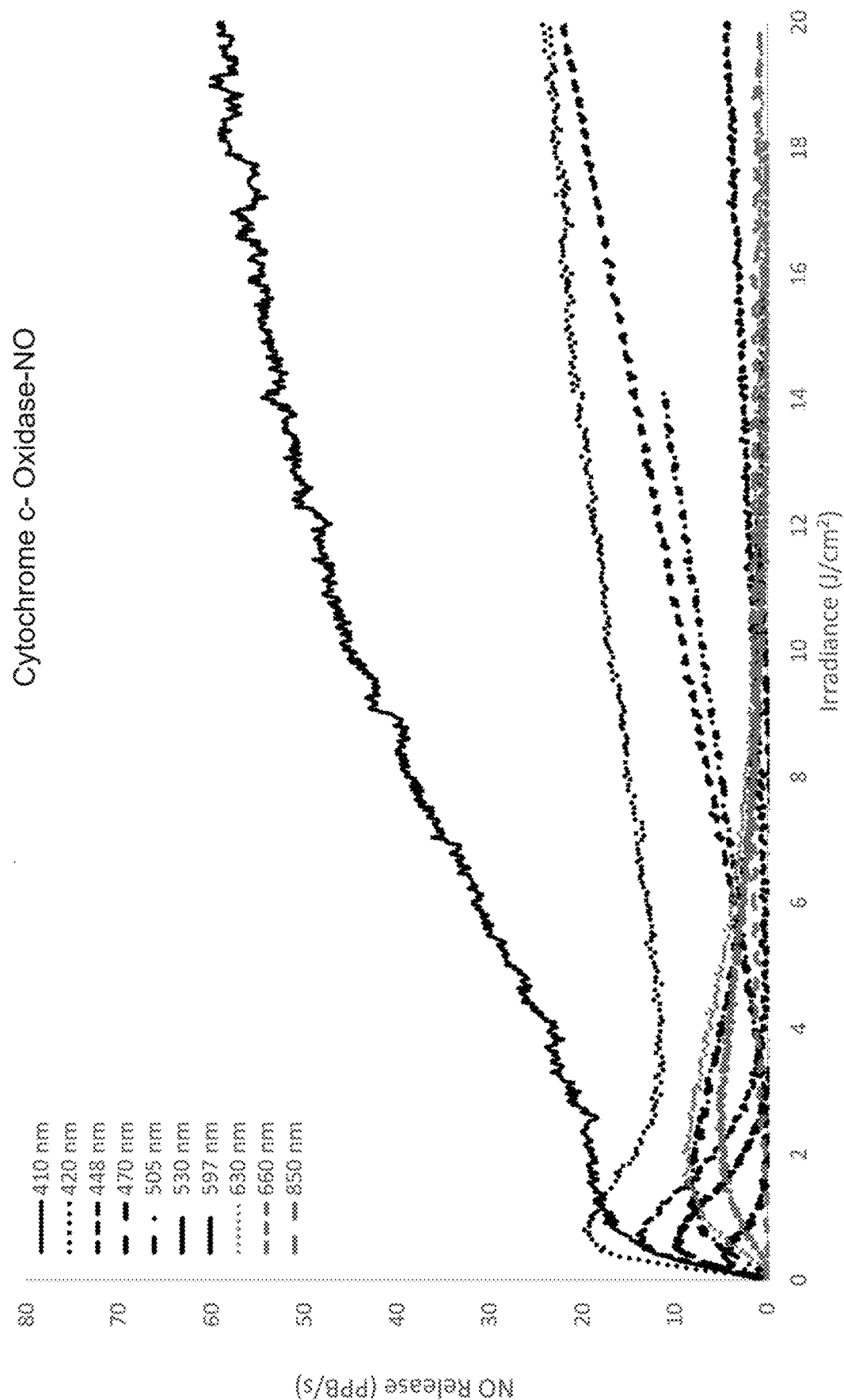
FIG. 61 is a plot of NO release rate (PPB/s) versus irradiance (J/cm$^2$) from cytochrome c-oxidase-NO for ten (10) different wavelengths of incoherent light ranging from 410 nm to 850 nm.
Figure 62:
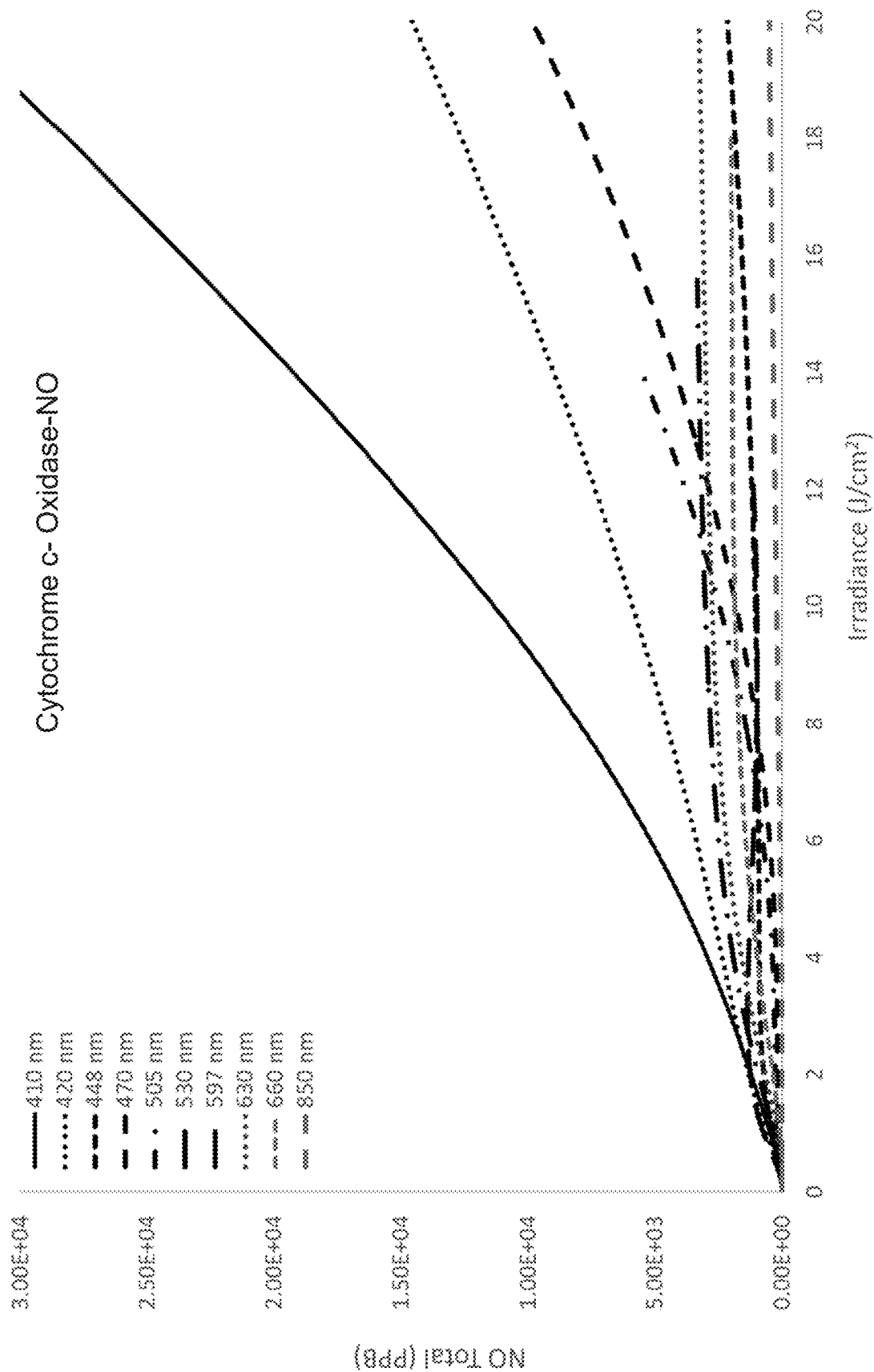
FIG. 62 is a plot of total NO release (PPB) versus irradiance (J/cm$^2$) from cytochrome c-oxidase-NO for ten (10) different wavelengths of incoherent light ranging from 410 nm to 850 nm.

FIG. 61 is a plot of NO release rate (PPB/s) versus irradiance (J/cm²) from cytochrome c-oxidase NO for ten (10) different wavelengths of incoherent light ranging from 410 nm to 850 nm. Nitric oxide was added to cytochrome c oxidase by reacting with proline-NONOate in PBS (pH 6.5) under anaerobic conditions and in the dark. After 45 minutes of reaction, the NO release was measured as a function of irradiation using a chemiluminescence detector. As shown, the highest four NO release rates were achieved for 410 nm light, 420 nm light, 448 nm light, and 470 nm light, respectively. For 410 nm light, NO release rate generally increased with increasing irradiance, whereas for other wavelengths, at least a local peak of NO release rate was achieved for irradiance values of around 1 to 2 J/cm², followed by an increase in NO release rate with increasing irradiance for 420 nm light, 448 nm light, and 470 nm light, but higher wavelengths of light resulted in decreased NO release rate with increasing irradiance. Referring to FIG. 62, total NO released from cytochrome c-oxidase-NO was quantified by integrating the data on NO release rate of FIG. 61. The highest three amounts of total NO release were achieved for 410 nm light, 420 nm light, and 448 nm light, respectively, with greater slopes for shorter wavelengths.

Figure 63:
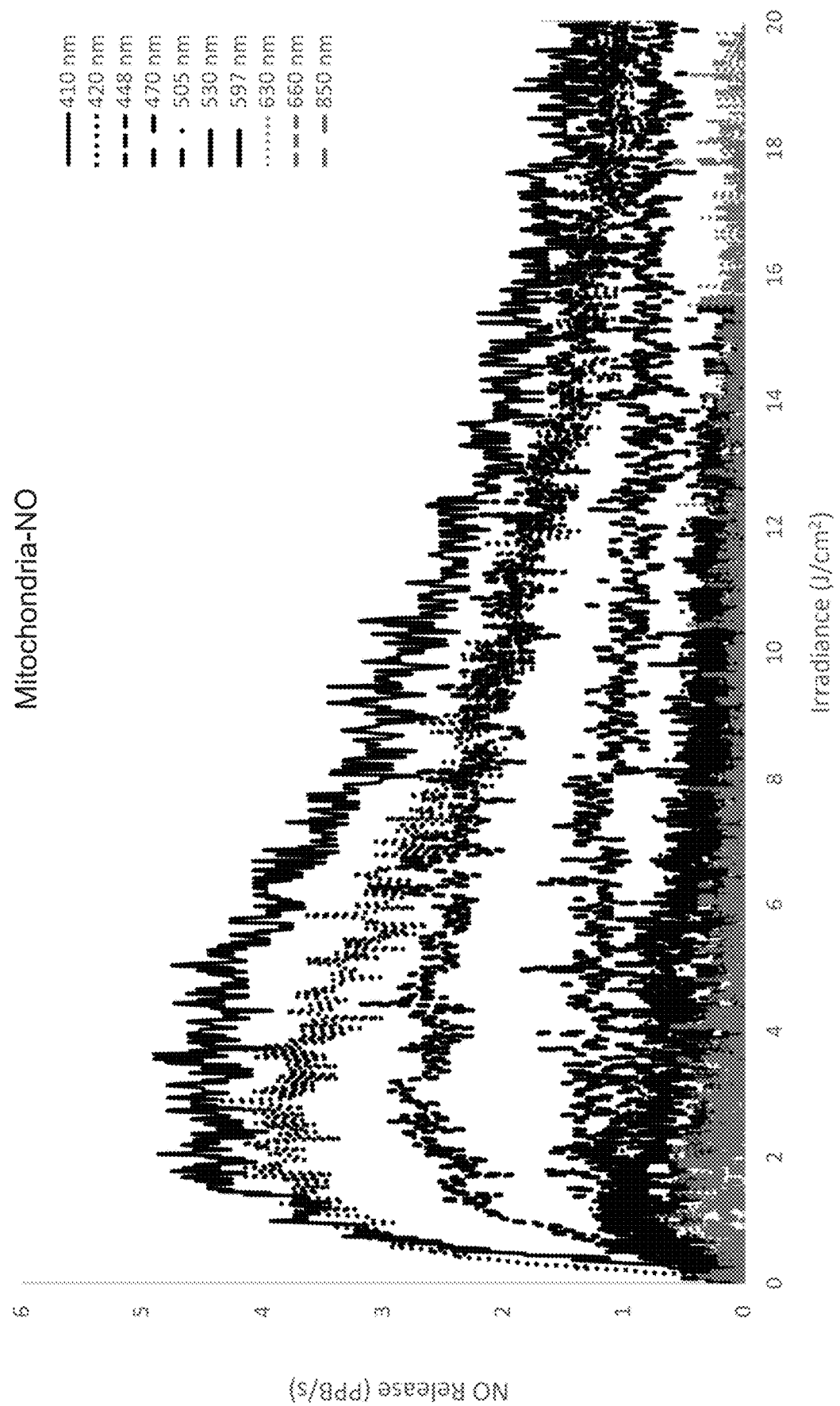
FIG. 63 is a plot of NO release rate (PPB/s) versus irradiance (J/cm$^2$) from mitochondria-NO for ten (10) different wavelengths of incoherent light ranging from 410 nm to 850 nm.
Figure 64:
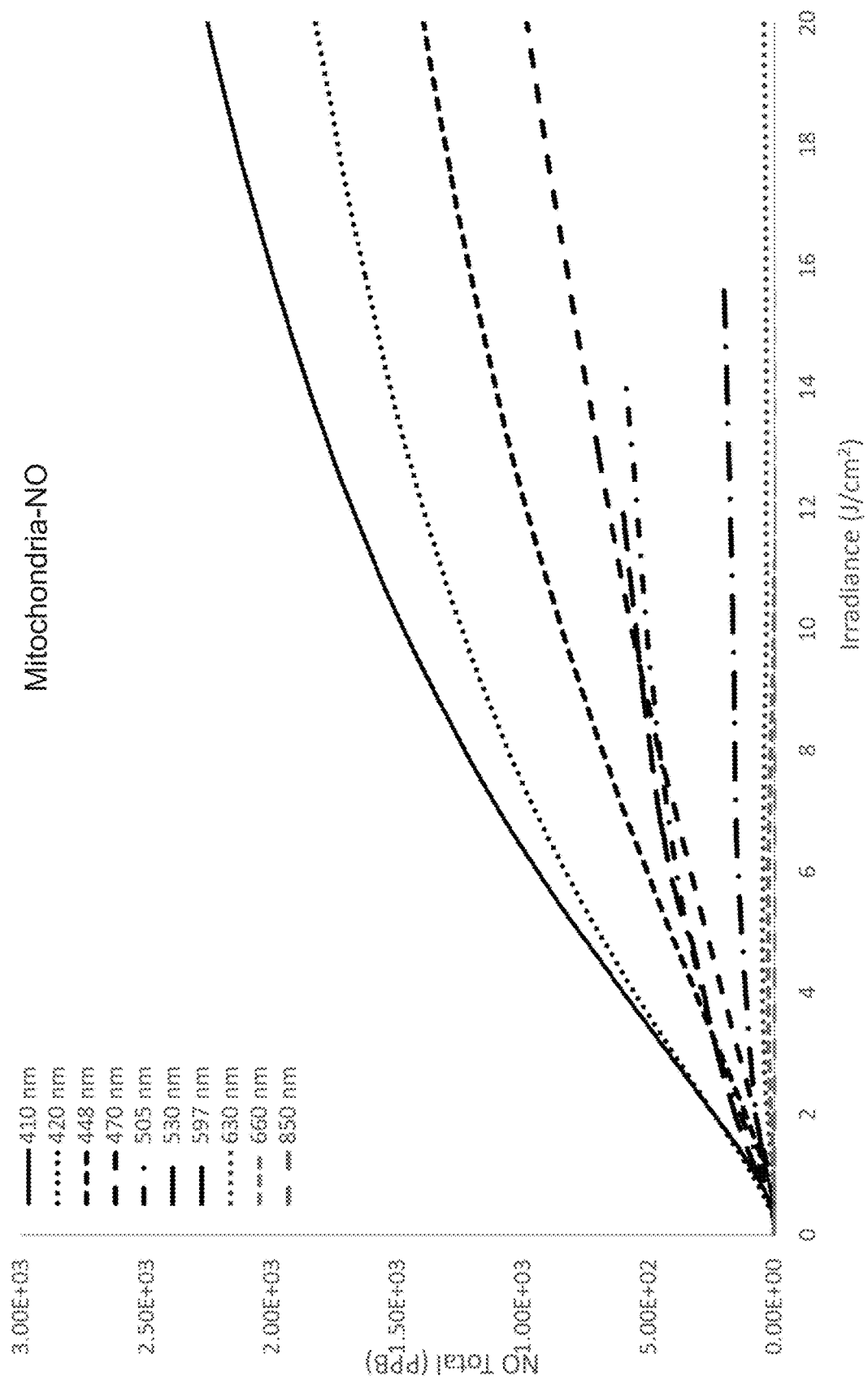
FIG. 64 is a plot of total NO release (PPB) versus irradiance (J/cm$^2$) from mitochondria-NO for ten (10) different wavelengths of incoherent light ranging from 410 nm to 850 nm.

FIG. 63 is a plot of NO release rate (PPB/s) versus irradiance (J/cm²) from mitochondria-NO for ten (10) different wavelengths of incoherent light ranging from 410 nm to 850 nm. Nitric oxide was added to mitochondria isolated from bovine heart by reacting it with S-nitrosoglutatione in PBS (pH 6.5) under anaerobic conditions and in the dark. After 45 minutes of reaction, the NO release was measured as a function of irradiation using a chemiluminescence detector. As shown, the highest four NO release rates were achieved for 410 nm light, 420 nm light, 448 nm light, and 470 nm light, respectively. For each wavelength, a peak of NO release rate was achieved for irradiance values in a range of from about 2 to 4 J/cm², followed by a decrease in NO release rate with increasing irradiance. Referring to FIG. 64, total NO released from mitochondria-NO was quantified by integrating the data on NO release rate of FIG. 63. The highest four amounts of total NO release were achieved for 410 nm light, 420 nm light, 448 nm light, and 470 nm light, respectively.

The preceding FIGS. 53 to 64 show that different types of bonds (e.g., RSNO, RNNO, and metal-NO) may require different light wavelengths and/or light irradiation values to effectuate release of nitric oxide. Based on the data represented in FIGS. 53 to 64, an important wavelength of interest is 420 nm, since this wavelength represents perhaps the closest safe wavelength to the ultraviolet range (since substantially all incoherent emissions having a peak wavelength of 420 nm, including portions tailing above and below this peak value, remain well above the 400 nm UV threshold), exhibits a demonstrated high (or highest) NO release from a wide range of proteins (Hemoglobin-NO, S-Nitrosglutathione (GSNO), Albumin-NO, Cytochrome c-NO, Cytochrome c oxidase-NO, and Mitochondria-NO), and appears to lead to enzymatic generation of NO. A secondary wavelength of interest is 530 nm, since it appears to be more effective than longer wavelength red at triggering NO release from GSNO. These conclusions contradict various findings in the art (e.g., by Karu, T, Handbook of Laser Wavelengths, Chapter 48, "Low-Power Laser Therapy", pp. 48-1 to 48-25 (2003); by Ball, K., et al., "Low intensity light stimulates nitrite-dependent nitric oxidant synthesis but not oxygen consumption by cytochrome c oxidase: implications for phototherapy," Journal of Photochemistry and Photobiology B: Biology 102 (2011) 182-191; and by Hamblin, M., "The Role of Nitric Oxide in Low Level Light Therapy," Proc. of SPIE Vol. 6846, 684602, (2008)) that red light including wavelengths in a range of from 605 nm to 820 nm may be particularly suitable for releasing NO from heme groups of CCO, for release of NO from CCO generally, and for increased ATP synthesis.

Based on the findings that short wavelength blue light is effective for enhancing endogenous stores of nitric oxide and/or triggering nitric oxide release, one aspect of the disclosure relates to a method of modulating nitric oxide in living mammalian tissue, the method comprising: impinging light on the tissue, wherein the light impinged on the tissue comprises incoherent light emissions including a first peak wavelength in a range of from 410 nm to 440 nm and a first radiant flux, and wherein the first peak wavelength and the first radiant flux are selected to stimulate at least one of (i) enzymatic generation of nitric oxide to increase endogenous stores of nitric oxide or (ii) release of nitric oxide from endogenous stores of nitric oxide; wherein the light impinged on the tissue is substantially devoid of light emissions having a peak wavelength in a range of from 600 nm to 900 nm (e.g., encompassing red visible light as well as a portion of the infrared range). An absence of red and/or infrared light contradicts various references describing the desirability of red and/or infrared light as primary wavelengths for skin penetration and to provide phototherapeutic benefit.

In certain embodiments, the light impinged on the tissue is devoid of emissions of any wavelength conversion material (e.g., a phosphor, a quantum dot, or another lumiphoric material) stimulated by incoherent light emissions having a peak wavelength in a range of from 410 nm to 440 nm. In certain embodiments, the tissue on which light is impinged is devoid of an applied or received photosensitive therapeutic compound or agent (e.g., a pharmaceutical composition or the like, which may be administered topically, orally, or via injection). In certain embodiments, at least 65%, at least 75%, at least 80%, at least 85%, or at least 95% of a fluence of light impinged on the tissue consists of the incoherent light emissions including a first peak wavelength in a range of from 410 to 440 nm. In certain embodiments, the light impinged on the tissue is substantially devoid of light emissions having a peak wavelength in a range of from 441 nm to 490 nm. In certain embodiments, the incoherent light emissions including a first peak wavelength in a range of from 410 nm to 440 nm are provided as a plurality of discrete pulses.

In certain embodiments, the light impinged on the tissue further comprises incoherent light emissions including a second peak wavelength in a range of from 500 nm to 540 nm. This is consistent with Applicant's finding that light having a peak wavelength of 530 nm appears to be more effective than certain other wavelengths (including longer wavelength red) at triggering NO release from GSNO. In certain embodiments, the incoherent light emissions including a first peak wavelength in a range of from 410 nm to 440 nm are impinged on the tissue during a first time window, the incoherent light emissions including a second peak wavelength in a range of from 500 nm to 540 nm are impinged on the tissue during a second time window, and at least a portion of the second time window is non-overlapping with the first time window.

In certain embodiments, the first peak wavelength and the first radiant flux are selected to stimulate enzymatic generation of nitric oxide to increase endogenous stores of nitric oxide. In certain embodiments, the first peak wavelength and the first radiant flux are selected to release nitric oxide from the endogenous stores of nitric oxide.

In certain embodiments, the tissue comprises at least one of epithelial tissue, mucosal tissue, connective tissue, muscle tissue, or cervical tissue. In certain embodiments, the tissue comprises dermal tissue. In certain embodiments, a method further comprises sensing a temperature condition on or proximate to (a) a therapeutic device arranged to impinge light on the tissue, or (b) the tissue; generating at least one signal indicative of the temperature condition; and controlling impingement of light on the tissue responsive to the at least one signal. In certain embodiments, the light impinged on the tissue comprises a fluence in a range of from about 0.5 J/cm² to about 100 J/cm², or from about 2 J/cm² to about 80 J/cm², or from about 5 J/cm² to about 50 J/cm².

In another aspect, the disclosure relates to a device for modulating nitric oxide in living mammalian tissue, the device comprising: an ambient light blocking element; and at least one first light emitting element positioned between the ambient light blocking element and the tissue, wherein the at least one first light emitting element is configured to impinge incoherent light on the tissue, said incoherent light having a first peak wavelength and a first radiant flux, wherein the first peak wavelength and the first radiant flux are selected to stimulate at least one of (i) enzymatic generation of nitric oxide to increase endogenous stores of nitric oxide or (ii) release of nitric oxide from endogenous stores of nitric oxide; wherein the device is substantially devoid of any light emitting element configured to impinge on the tissue light having a peak wavelength in a range of from 600 nm to 900 nm.

In certain embodiments, the device is substantially devoid of any light emitting element configured to impinge light having a peak wavelength in a range of from 441 nm to 490 nm on the tissue. In certain embodiments, the device is devoid of any wavelength conversion material configured to be stimulated by the at least one first light emitting element. In certain embodiments, the device further comprises a flexible substrate supporting the at least one first light emitting element. In certain embodiments, the device is configured to conform to the tissue with a light-transmissive material arranged in contact with the tissue. In certain embodiments, the light impinged on the tissue is substantially devoid of light emissions having a peak wavelength in a range of from 441 nm to 490 nm. In certain embodiments, the device further comprises driver circuitry configured to generate the incoherent light emissions including the first peak wavelength, wherein the first peak wavelength is in a range of from 410 nm to 440 nm, and said incoherent light emissions comprise a plurality of discrete pulses.

In certain embodiments, the device further comprises at least one second light emitting element configured to impinge incoherent light on the tissue, said incoherent light having a second peak wavelength and a second radiant flux, wherein the second peak wavelength is in a range of from 500 nm to 540 nm. In certain embodiments, the device is configured to impinge incoherent light emissions including the first peak wavelength during a first time window, wherein the first peak wavelength is in a range of from 410 nm to 440 nm, and being configured to impinge incoherent light emissions including the second peak wavelength in a range of from 500 nm to 530 nm during a second time window, wherein at least a portion of the second time window is non-overlapping with the first time window. In certain embodiments, the device further comprises a probe configured for insertion into a mammalian body cavity or opening (e.g., incision) defined in a mammalian body, wherein the at least one first light emitting element is supported by the probe.

Figure 65:
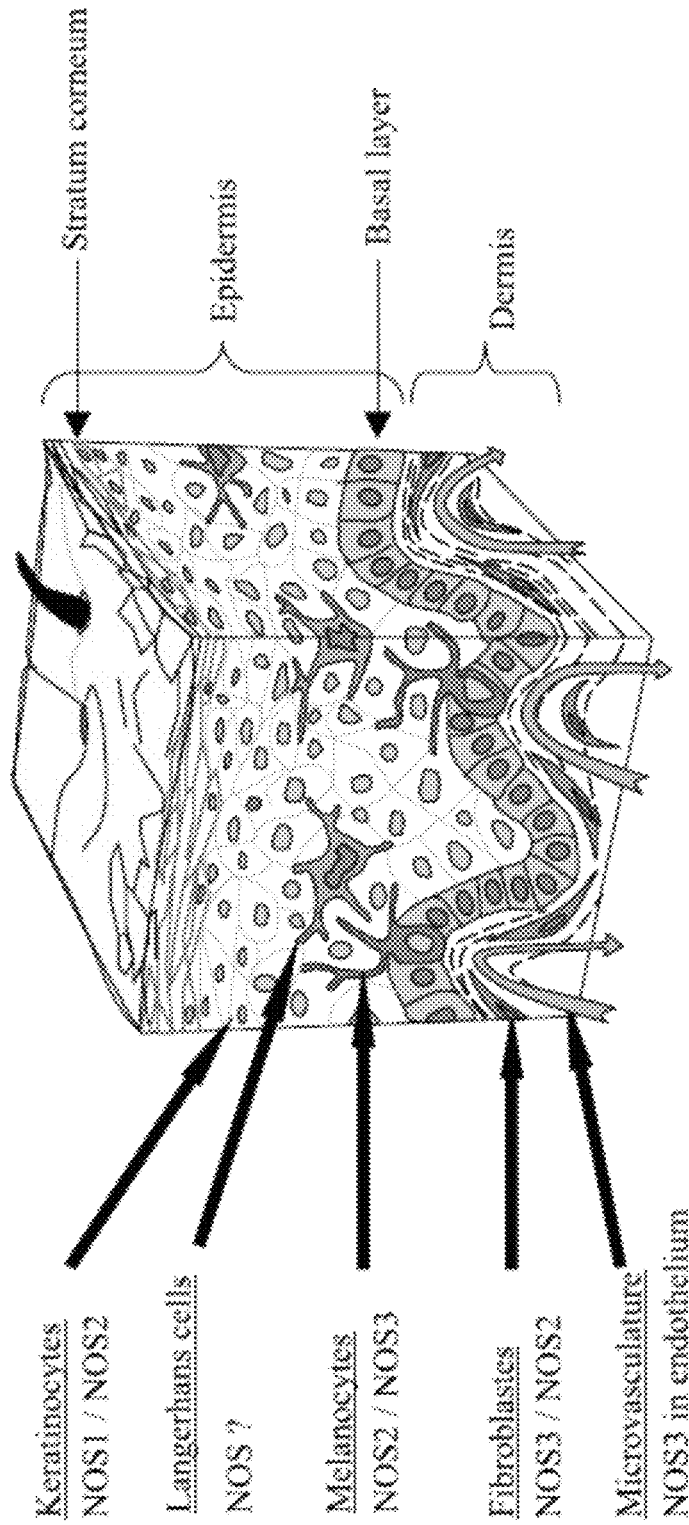
FIG. 65 is a related art perspective view illustration of a cross-section of dermis and epidermis layers of human skin showing various types of cells containing nitric oxide compounds.

FIG. 65 is a perspective view illustration of a cross-section of dermis and epidermis layers of human skin showing various types of cells containing nitric oxide synthases or enzymes. Such image is reproduced from Cals-Grierson, M. M and Ormerod, A. D. Nitric Oxide 10 (2004) 179-193. As shown, the epidermis (extending from the stratum corneum to and including the basal layer) includes keratinocytes, Langerhans cells, and melanocytes, whereas the dermis (under the basal layer) includes fibroblasts and microvasculature. Different NOS enzymes occur in different layers of the skin. nNOS (or NOS1) is present in keratinocytes; eNOS (or NOS3) is present in fibroblasts, melanocytes, and the endothelium; and iNOS (or NOS2) is present throughout. Both nNOS and eNOS are calcium dependent enzymes. iNOS is inducible and therefore increases in response to the immune system.

Figure 66:
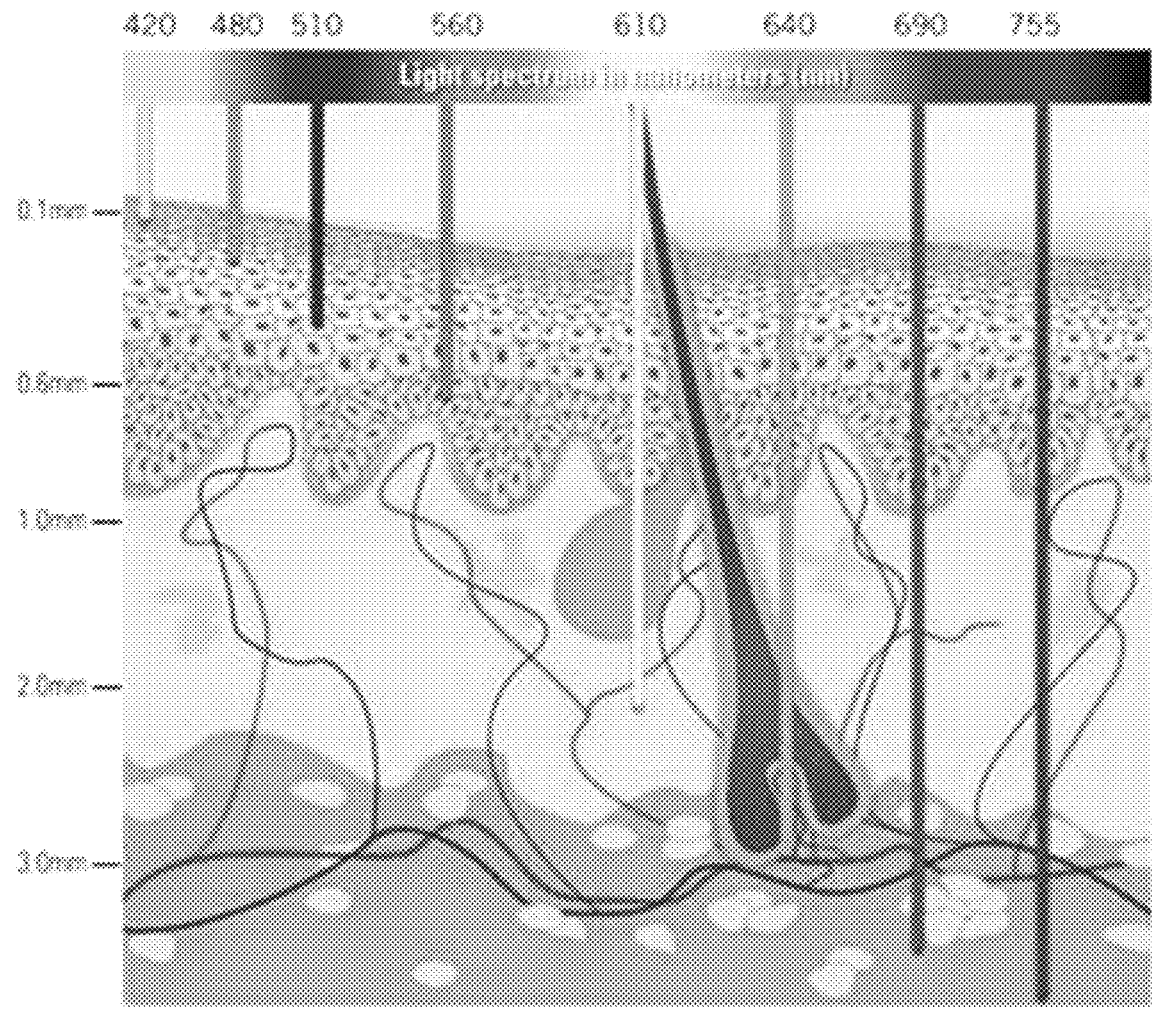
FIG. 66 is a related art cross-sectional illustration of human skin with a superimposed representation of depth penetration of coherent light of eight different wavelengths ranging from 420 nm to 755 nm.

FIG. 66 is a related art cross-sectional illustration of human skin with a superimposed representation of depth penetration of coherent (e.g., laser) light of eight different wavelengths ranging from 420 nm to 755 nm. Such image is sourced from www.spectrumsciencebeauty.com.au/2014/09/16/ipl-hair-removal/#prettyPhoto/0/. FIG. 66 shows a single hair follicle (below the value of "640 nm", at a depth of between 2 and 3 mm). As shown, the conclusion in the art is that blue light (e.g., 420 nm, 480 nm) is incapable of penetrating human skin to a sufficient depth to reach a hair follicle.

Figure 67A:
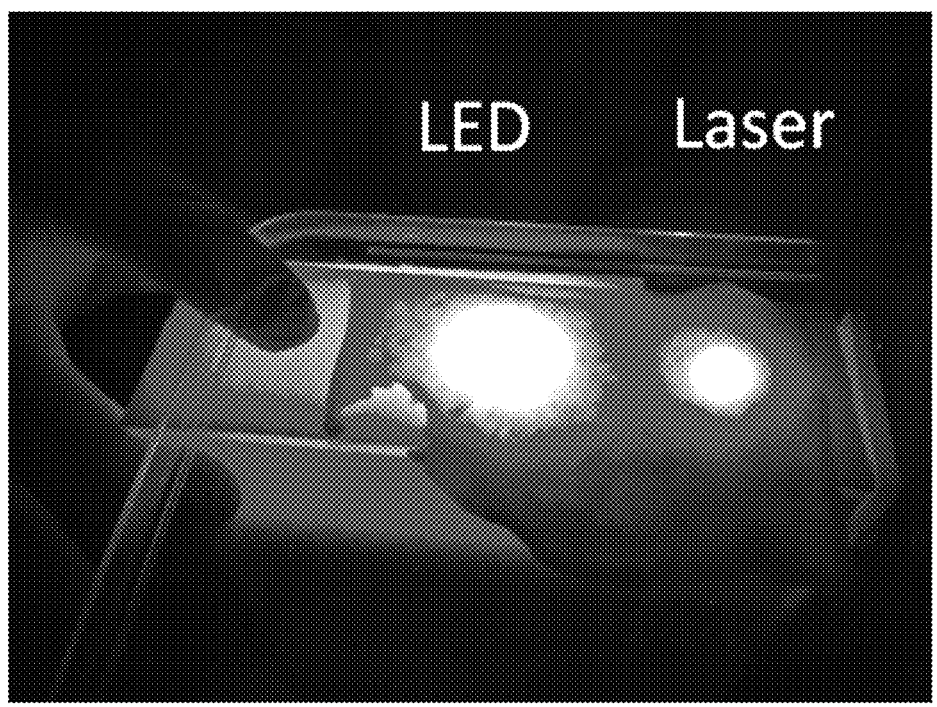
FIG. 67A is an upper perspective view photograph comparing the transmittance of red (660 nm peak wavelength) incoherent (LED) light and a red (660 nm) coherent (laser) light through a human skin sample.
Figure 67B:
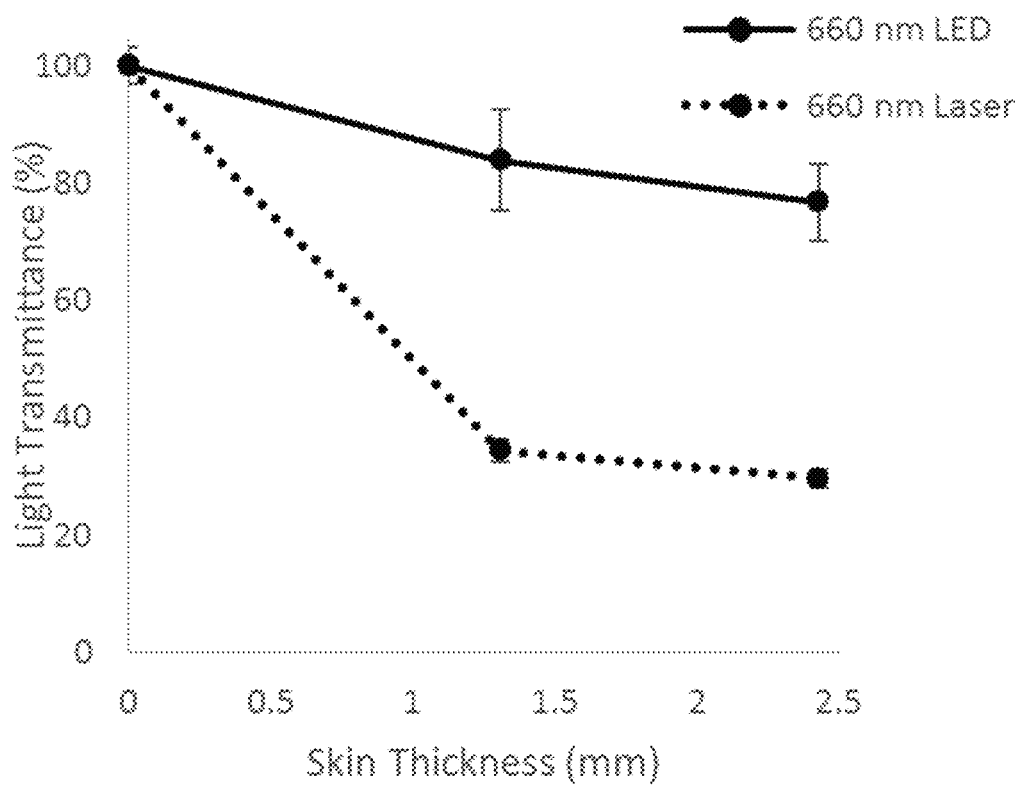
FIG. 67B is a plot of light transmittance percentage as a function of skin thickness (mm) for transmittance of red (660 nm peak wavelength) incoherent (LED) light and a red (660 nm) coherent (laser) light through human skin samples of two different thicknesses at equivalent irradiance.
Figure 68A:
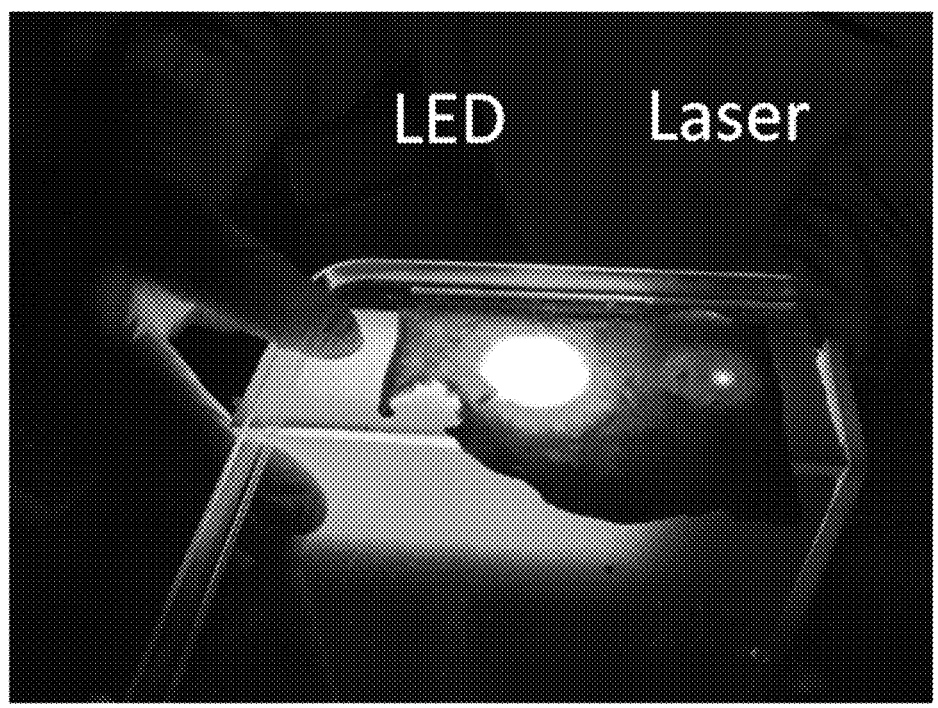
FIG. 68A is an upper perspective view photograph comparing the transmittance of a green (530 nm peak wavelength) incoherent (LED) light and a green (530 nm) coherent (laser) light through a human skin sample.
Figure 68B:
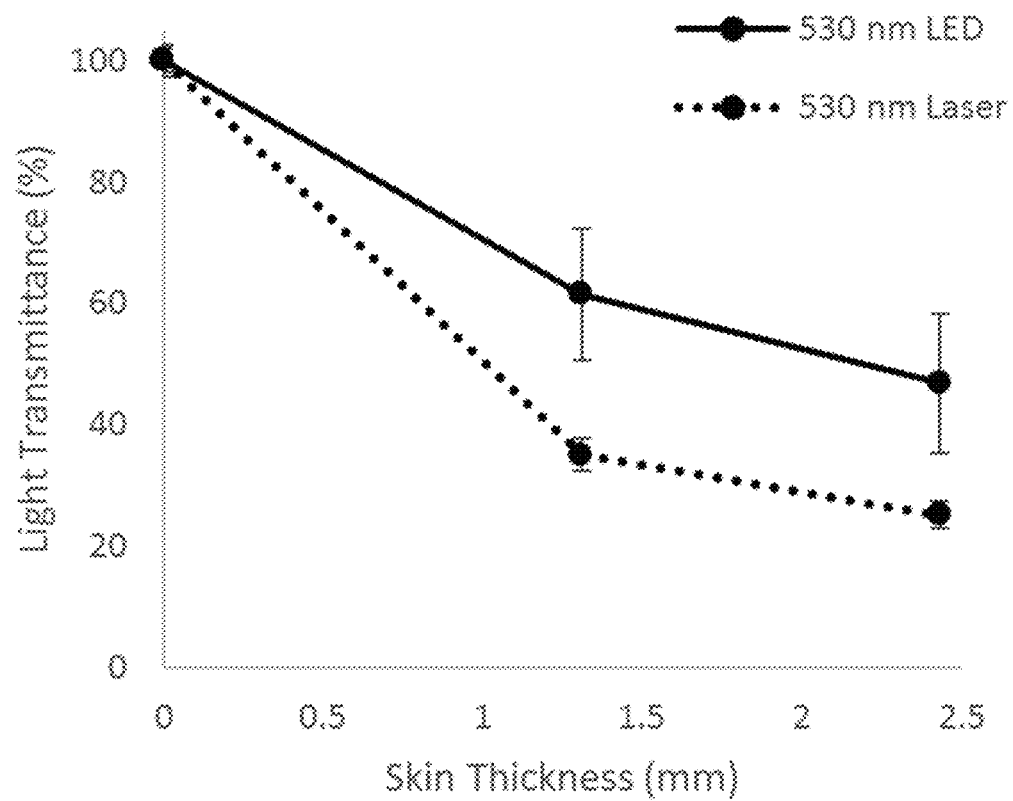
FIG. 68B is a plot of light transmittance percentage as a function of skin thickness (mm) for transmittance of green (530 nm peak wavelength) incoherent (LED) light and a green (530 nm) coherent (laser) light through human skin samples of two different thicknesses at equivalent irradiance.
Figure 69A:
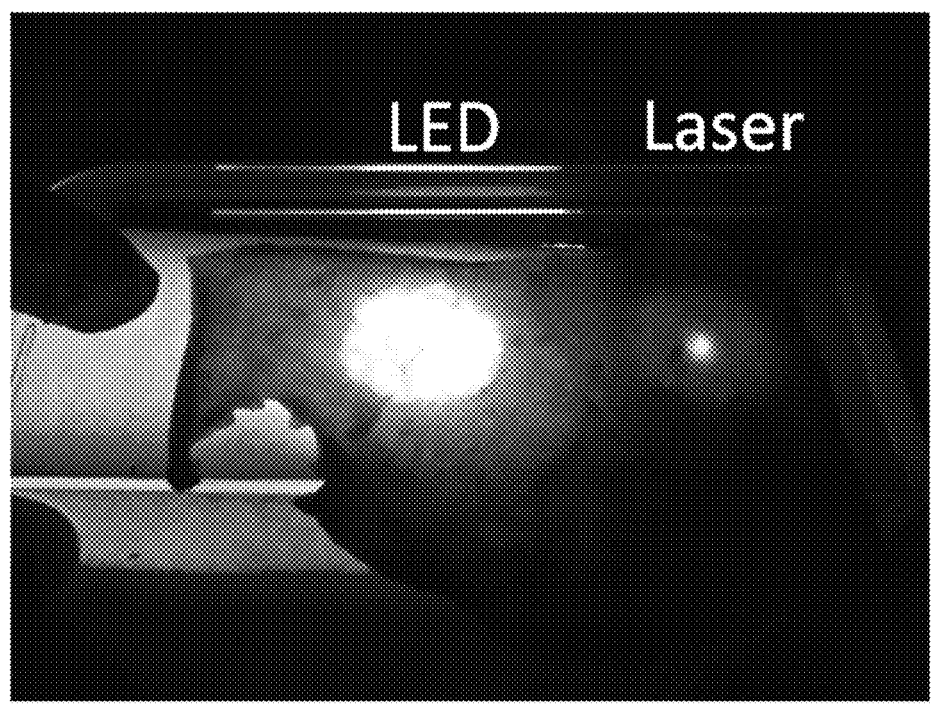
FIG. 69A is an upper perspective view photograph comparing the transmittance of a blue (420 nm peak wavelength) incoherent (LED) light and a blue (420 nm) coherent (laser) light through a human skin sample.
Figure 69B:
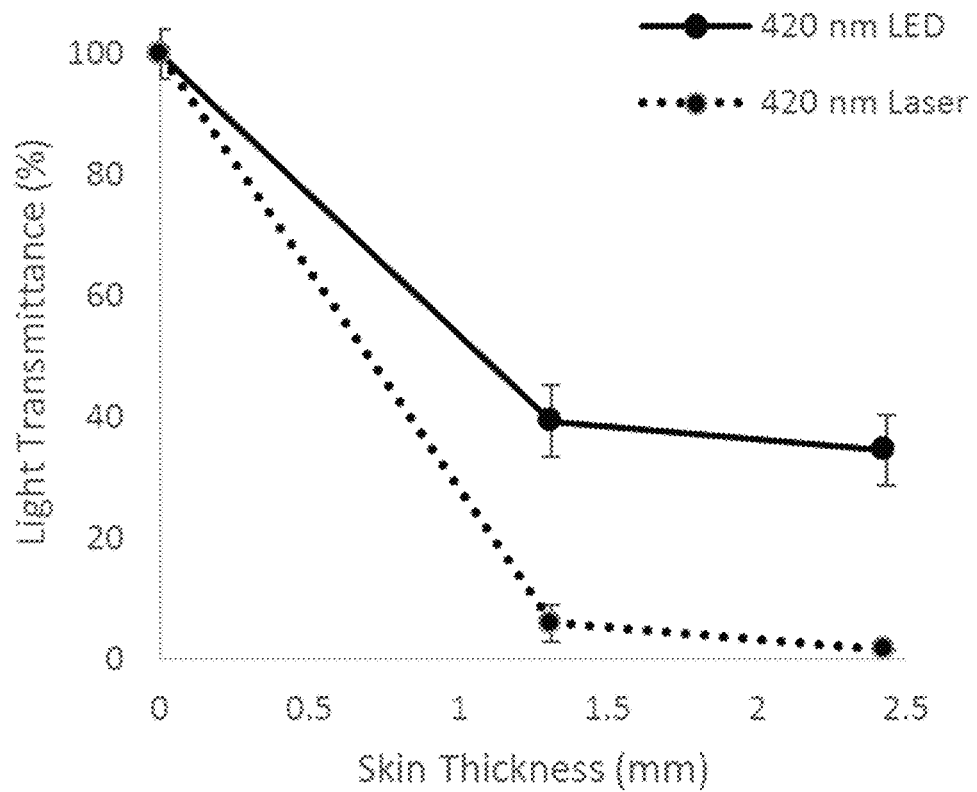
FIG. 69B is a plot of light transmittance percentage as a function of skin thickness (mm) for transmittance of blue (420 nm peak wavelength) incoherent (LED) light and a blue (420 nm) coherent (laser) light through human skin samples of two different thicknesses at equivalent irradiance.

Applicant performed various experiments to contradict this conclusion—instead confirming that coherent blue light is capable of penetrating human skin to a depth sufficient to reach hair follicles. Irradiance transmitted through full thickness skin was measured as a function of wavelength for laser and LED light sources. Light sources were matched to have equivalent irradiance as measured by a common photodiode. Wavelength was also matched between laser and LED light sources. FIGS. 67A, 68A, and 69A embody upper perspective view photographs of transmittance of incoherent (LED) light and coherent (laser) light through Caucasian (Fitzpatrick Skin Type II) human skin samples, with the respective figures separately corresponding to red (660 nm peak wavelength), green (530 nm peak wavelength), and blue (420 nm peak wavelength) sources. Human skin samples of different thicknesses (1.3 mm and 2.5 mm) were used in each instance. FIGS. 67B, 68B, and 69B embody plots of light transmittance percentage as a function of skin thickness (mm) for transmittance of incoherent (LED) light and coherent (laser) light through the human skin samples of two different thicknesses. In each of FIGS. 67B, 68B, and 69B, a significantly greater percentage of incoherent (LED) light was transmitted through skin than coherent (laser) light. Notably, referring to FIG. 69B, nearly 40% of the incoherent (420 nm peak) blue light was transmitted through a Caucasian skin sample having a thickness of 2.5 mm, whereas a low single digit percentage of coherent blue light was transmitted through the same sample.

Figure 70:
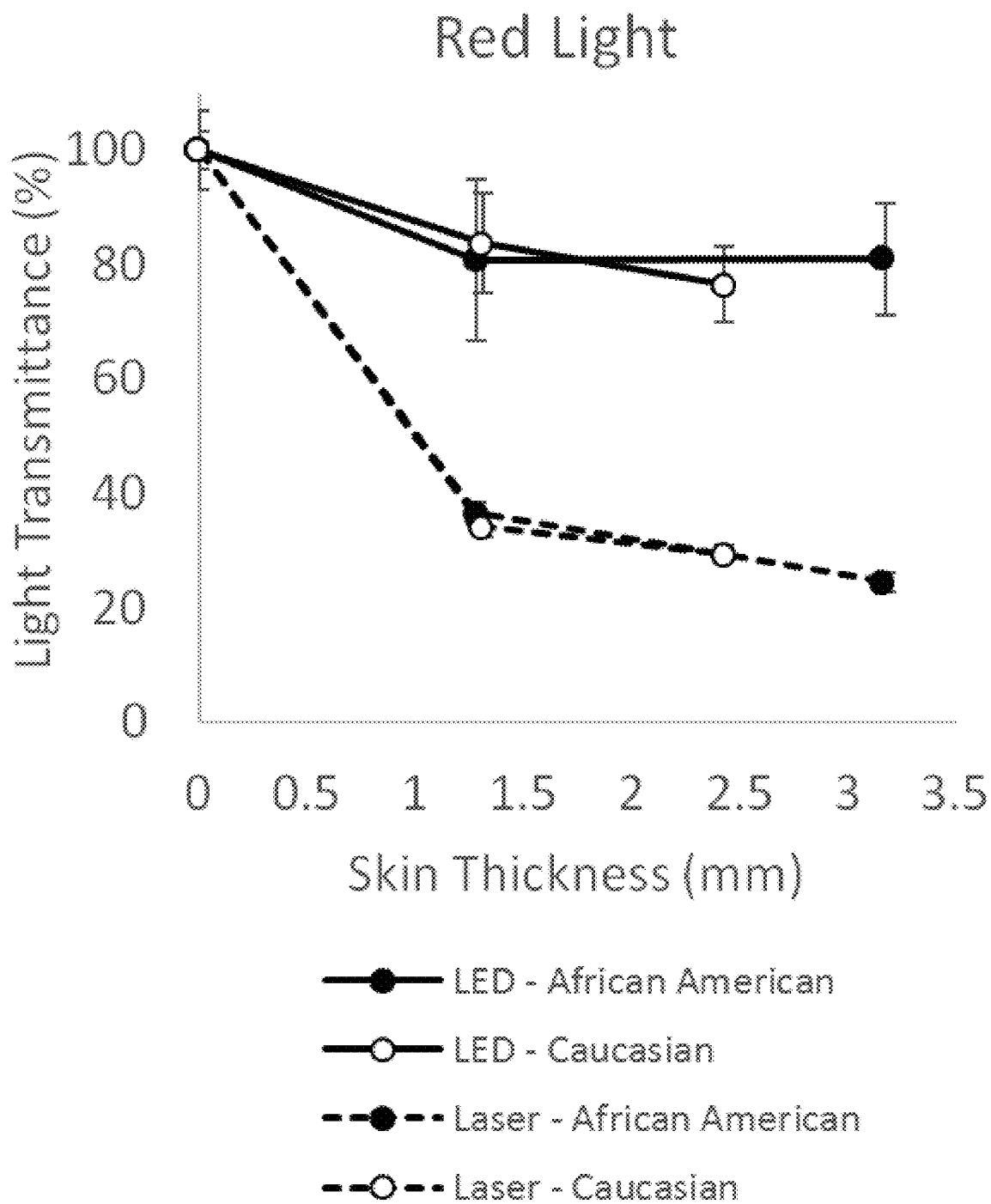
FIG. 70 is a plot of light transmittance percentage as a function of skin thickness (mm) for transmittance of red (660 nm peak wavelength) incoherent (LED) light and red (660 nm) coherent (laser) light through human skin samples of two different pigmentations and three different thicknesses.
Figure 71:
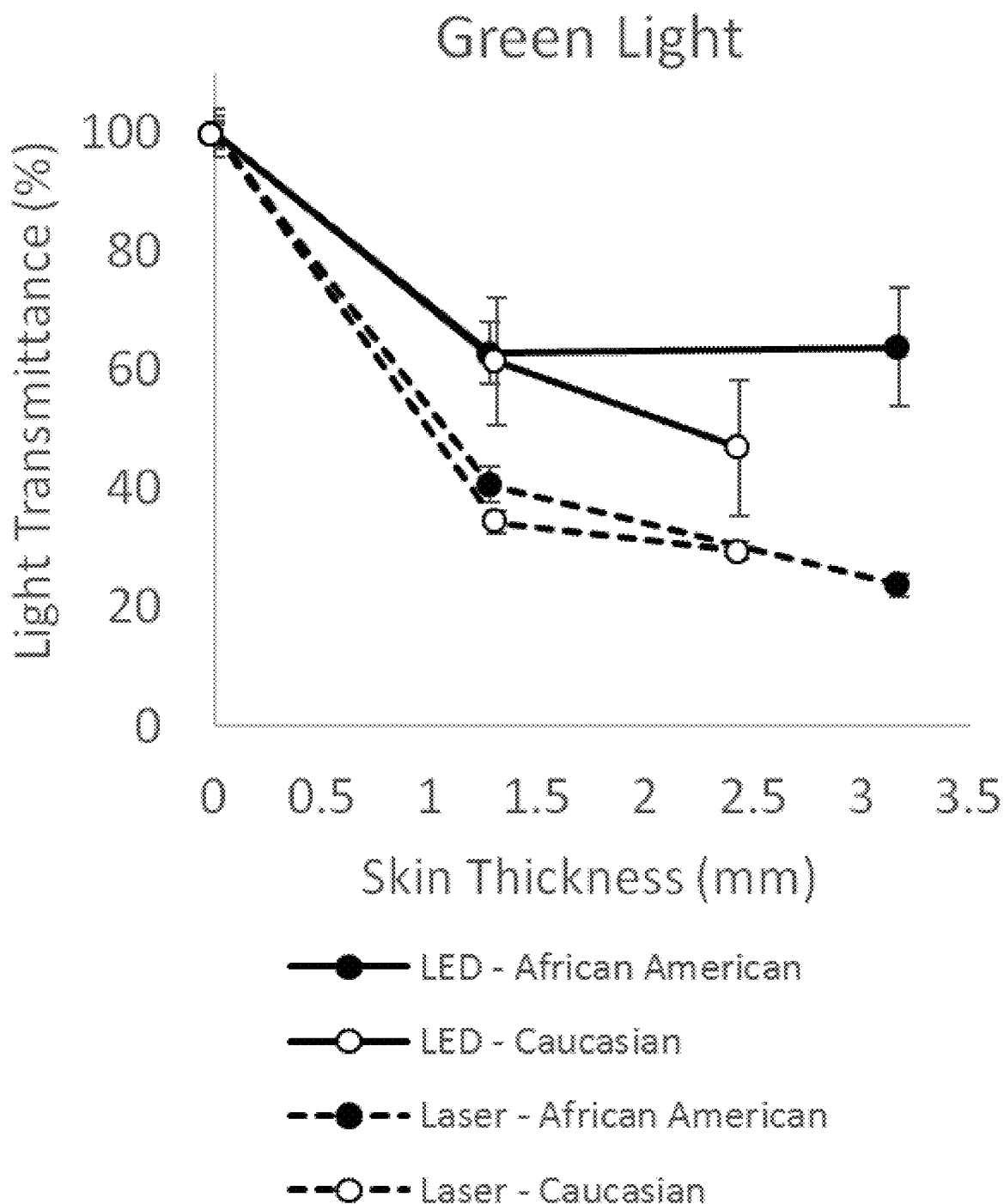
FIG. 71 is a plot of light transmittance percentage as a function of skin thickness (mm) for transmittance of green (530 nm peak wavelength) incoherent (LED) light and green (530 nm) coherent (laser) light through human skin samples of two different pigmentations and three different thicknesses.
Figure 72:
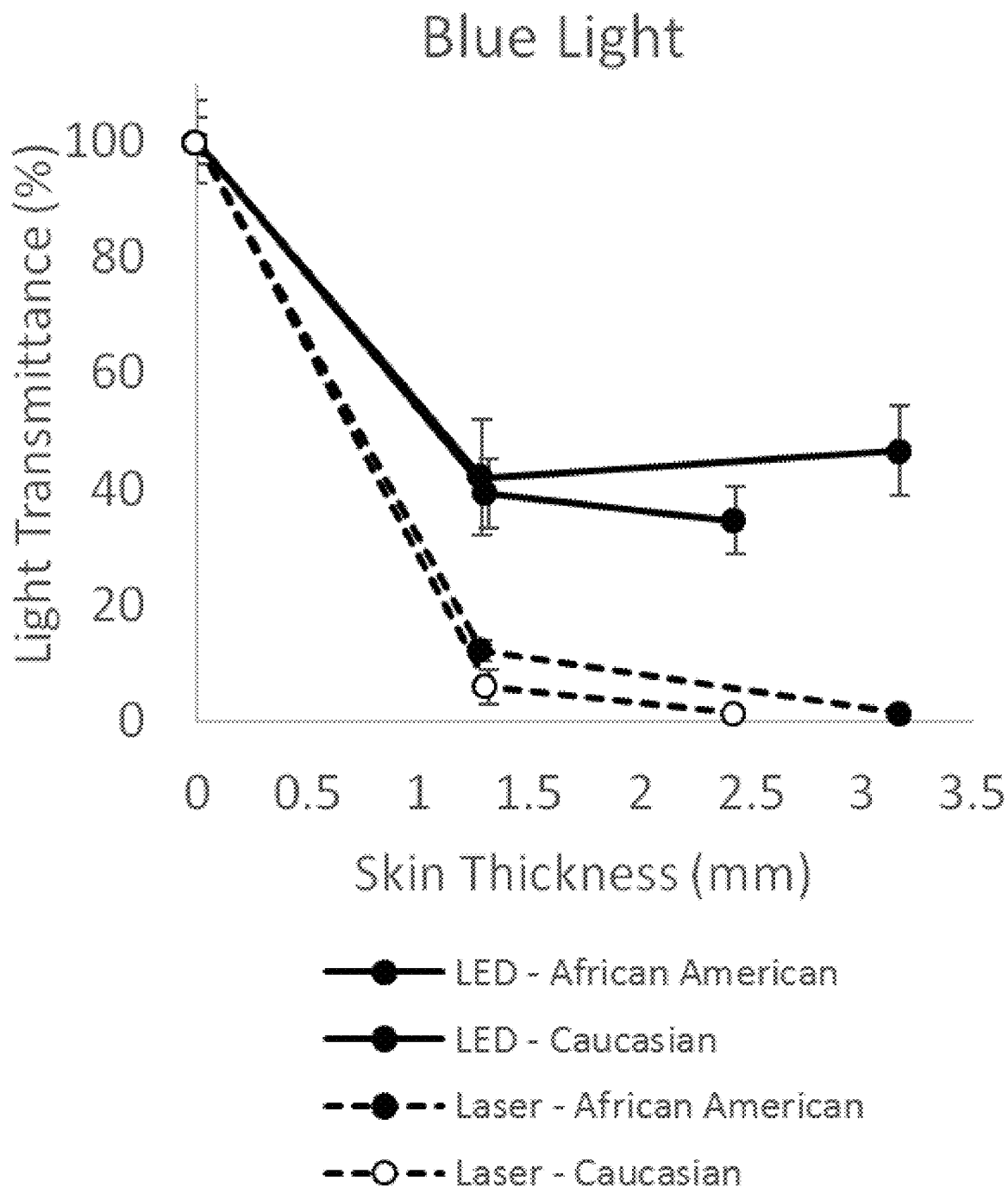
FIG. 72 is a plot of light transmittance percentage as a function of skin thickness (mm) for transmittance of blue (420 nm peak wavelength) incoherent (LED) light and blue (420 nm) coherent (laser) light through human skin samples of two different pigmentations and three different thicknesses.

To determine whether red, green, and blue coherent and incoherent light can penetrate skin of racially diverse types, experiments were performed using the apparatuses of FIGS. 67A, 68A, and 69A using human skin samples of three different thicknesses for each of two different pigmentations (i.e., African American skin of Fitzpatrick Skin Type V, and Caucasian skin of Fitzpatrick Skin Type II). Results of these experiments for red (660 nm peak wavelength), green (530 nm peak wavelength), and blue (420 nm peak wavelength) sources are shown in FIGS. 70 to 72, respectively. As shown, despite the different skin pigmentation, the samples of African American skin of Fitzpatrick Skin Type V and samples of Caucasian skin of Fitzpatrick Skin Type II skin samples performed similarly with respect to light transmittance properties. As shown in FIG. 70, red incoherent (LED) light was transmitted through each sample at more than twice the percentage of red coherent (laser) light. As shown in FIGS. 71 and 72, green and blue incoherent (LED) light were transmitted through each sample at more than twice the percentage of green and blue coherent (laser) light, respectively. Conclusions to be gleaned from the foregoing experiments are that LEDs appear to be at least as effective as lasers (for wavelengths of 420-660 nm) at penetrating skin of different types; and that a high percentage of blue LED light is capable of penetrating Caucasian and African American skin at depths of 2.5 mm or more.

In certain embodiments, methods and devices disclosed herein may be used to enhance nitric oxide production and/or release to provide a hair loss solution (e.g., for treating androgenic alopecia and/or similar conditions). Hair loss is caused by an increase in DHT produced by the enzyme 5α-reductase. In particular, 5α-reductase reacts with testosterone and NADPH to produce dihydrotestosterone (DHT), which leads to shrinkage of hair follicles and hair loss. Applicant performed experiments to determine whether nitric oxide inhibits 5α-reductase, to thereby provide a potential for decreasing DHT concentration in the scalp and inhibit (or reverse) hair loss. S-Nitrosoglutathione (GSNO) was used as a NO donor. Nitric oxide is released from GSNO by NADPH, which is a necessary cofactor for the 5α-reductase enzyme.

Figure 73:
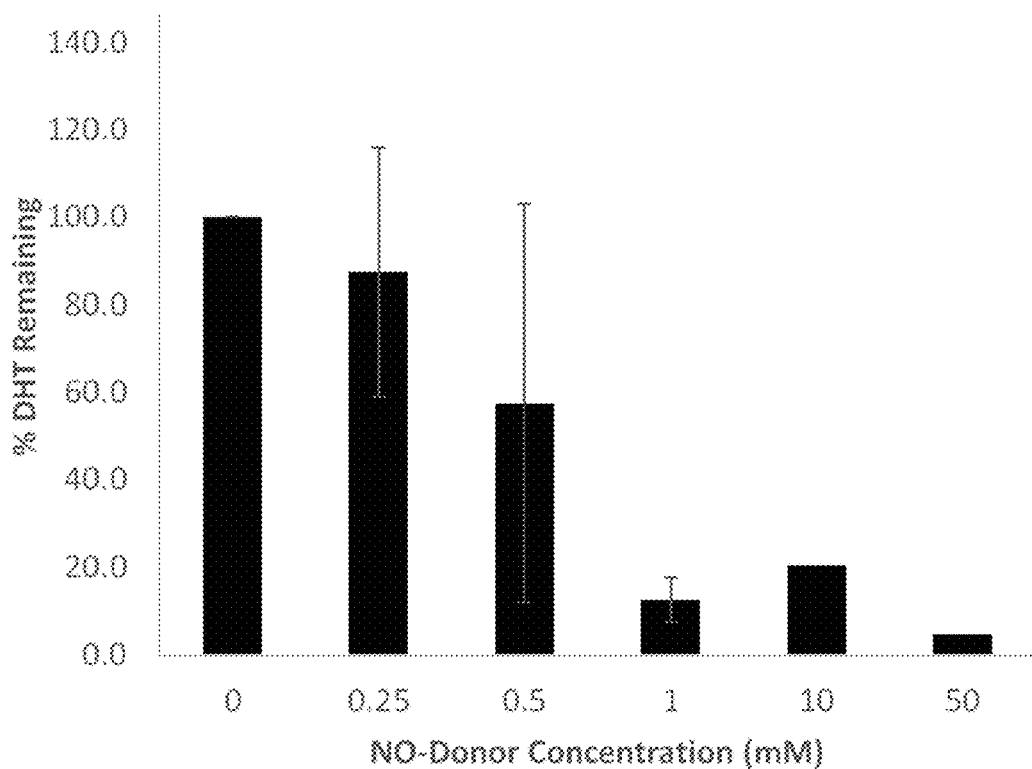
FIG. 73 is a plot of percentage of DHT remaining as a function of NO-donor concentration (mM) for six values ranging from 0 to 50 mM, showing that lower percentages of DHT remaining are correlated with increased NO-donor concentrations.
Figure 74:
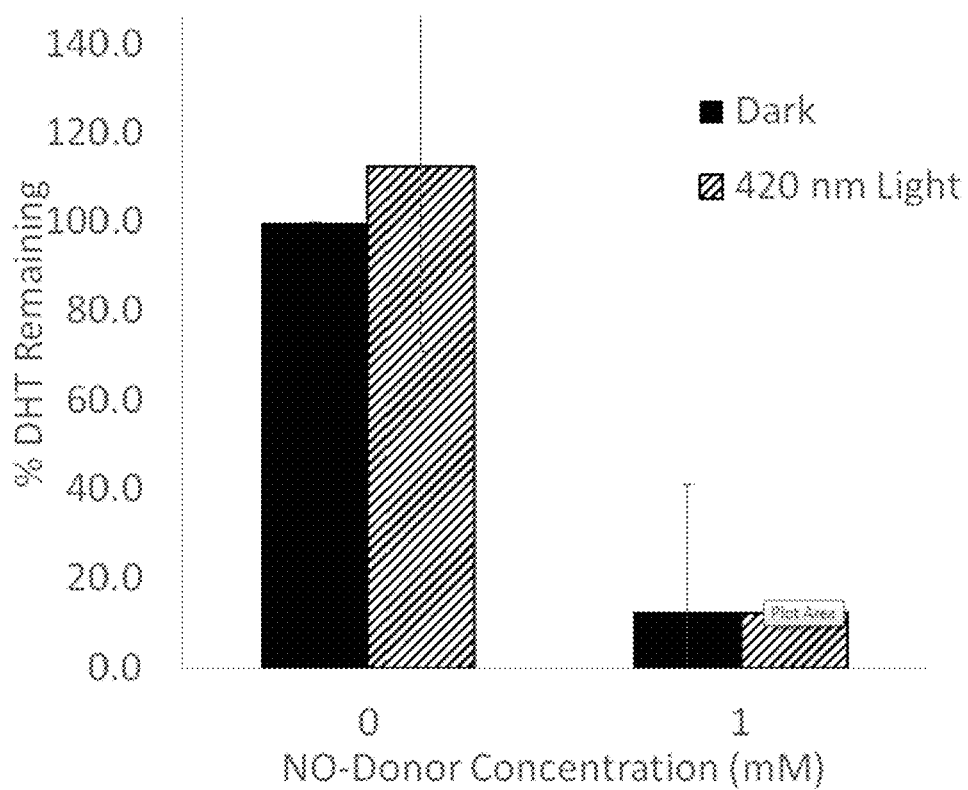
FIG. 74 is a plot of percentage of DHT remaining as a function of NO-donor concentration (mM) for dark conditions and 420 nm light exposure conditions for NO-donor concentrations of 0 and 1 mM.

FIG. 73 is a plot of percentage of DHT remaining as a function of NO-donor concentration (mM) for six values ranging from 0 to 50 mM, showing that lower percentages of DHT remaining are correlated with increased nitric oxide donor (e.g., GSNO) concentrations. FIG. 74 is a plot of percentage of DHT remaining as a function of NO-donor concentration (mM) for dark conditions and 420 nm light exposure conditions for NO-donor concentrations of 0 and 1 mM. Inhibition was still observed in the dark because the nitric oxide donor releases nitric oxide under the conditions of the assay. FIG. 74 shows that light does not have a detrimental effect on NO-induced inhibition. As demonstrated previously herein, modulated light therapy releases nitric oxide, which can then inhibit 5α-reductase and thereby provide a therapeutic benefit in terms of reduced (or reversed) hair loss for suffers of androgenic alopecia and/or similar conditions.

Those skilled in the art will recognize improvements and modifications to the preferred embodiments of the present disclosure. All such improvements and modifications are considered within the scope of the concepts disclosed herein and the claims that follow.

What is claimed is:

1. A method of modulating nitric oxide in living mammalian tissue, the method comprising:
   impinging light on the tissue, including incoherent light having a first peak wavelength and a first radiant flux, and incoherent light having a second peak wavelength and a second radiant flux;
   wherein the first peak wavelength and the first radiant flux are selected to release nitric oxide from endogenous stores of nitric oxide;
   wherein the second peak wavelength and the second radiant flux are selected to stimulate enzymatic generation of nitric oxide to increase endogenous stores of nitric oxide;
   wherein the second peak wavelength differs from the first peak wavelength by at least 25 nm;
   wherein each of the first peak wavelength and the second peak wavelength is in a red wavelength range; and
   wherein the light impinged on the tissue is devoid of coherent light.

2. The method of claim 1, wherein the second peak wavelength differs from the first peak wavelength by at least 50 nm.

3. The method of claim 1, wherein each of the first radiant flux and the second radiant flux is in a range of at least 5 mW/cm$^2$.

4. The method of claim 1, wherein each of the first radiant flux and the second radiant flux is in a range of from 5 mW/cm$^2$ to 60 mW/cm$^2$.

5. The method of claim 1, wherein the enzymatic generation of nitric oxide is mediated by inducible nitric oxide synthase (iNOS), neuronal nitric oxide synthase (nNOS), and/or endothelial nitric oxide synthase NOS (eNOS) in or proximate to the tissue.

6. The method of claim 1, wherein the endogenous stores of nitric oxide comprise nitrosoglutathione, nitrosoalbumin, nitrosohemoglobin, nitrosothiols, nitrosamines, and/or metal nitrosyl complexes in or proximate to the tissue.

7. The method of claim 1, wherein the light having a first peak wavelength is produced by a first array of light emitting devices, and the light having a second peak wavelength is produced by a second array of light emitting devices.

8. The method of claim 1, wherein the impinging of light having a first peak wavelength is performed during a first time window, the impinging of light having a second peak wavelength is performed during a second time window, and the second time window is at least partially non-overlapping with the first time window.

9. The method of claim 1, wherein: (a) the impinging of light having a first peak wavelength on the tissue includes impinging more than one discrete pulse of light having the first peak wavelength on the tissue during a first time window, and/or (b) the impinging of light having a second peak wavelength on the tissue includes impinging more than one discrete pulse of light having the second peak wavelength on the tissue during a second time window.

10. The method of claim 9, wherein one of the light having the first peak wavelength or the light having the second peak wavelength is impinged on the tissue as a plurality of discrete pulses, and the other of the light having the first peak wavelength or the light having the second peak wavelength is impinged on the tissue in a steady-state manner not including a plurality of discrete pulses.

11. The method of claim 1, further comprising impinging light having a third peak wavelength on the tissue, wherein the third peak wavelength differs from each of the first peak wavelength and the second peak wavelength by at least 10 nm.

12. The method of claim 11, wherein the light having the third peak wavelength comprises a third radiant flux, and the third peak wavelength and the third radiant flux are selected to stimulate enzymatic generation of nitric oxide to increase endogenous stores of nitric oxide.

13. The method of claim 1, wherein the tissue comprises at least one of epithelial tissue, mucosal tissue, bone, connective tissue, muscle tissue, cervical tissue, or dermal tissue.

14. The method of claim 1, wherein the tissue is within a body cavity of a patient.

15. The method of claim 1, wherein the second peak wavelength differs from the first peak wavelength by at least 40 nm.

16. The method of claim 1, wherein the first peak wavelength is in a range of from 620 nm to 640 nm, and the second peak wavelength is in a range of from 650 nm to 670 nm.

17. The method of claim 1, wherein each of the first radiant flux and the second radiant flux is in a range of from 5 mW/cm$^2$ to 10 mW/cm$^2$.

* * * * *